(12) United States Patent
Delhomel et al.

(10) Patent No.: US 8,258,182 B2
(45) Date of Patent: Sep. 4, 2012

(54) SUBSTITUTED 1,3-DIPHENYLPROPANE DERIVATIVES, PREPARATIONS AND USES THEREOF

(75) Inventors: Jean-François Delhomel, ACQ (FR); Rémy Hanf, Lille (FR); Karine Caumont-Bertrand, Frelinghien (FR)

(73) Assignee: Genfit, Loos (FR)

( * ) Notice: Subject to any disclaimer, the term of this patent is extended or adjusted under 35 U.S.C. 154(b) by 718 days.

(21) Appl. No.: 12/308,580

(22) PCT Filed: Jun. 21, 2007

(86) PCT No.: PCT/EP2007/056224
§ 371 (c)(1),
(2), (4) Date: Dec. 18, 2008

(87) PCT Pub. No.: WO2007/147879
PCT Pub. Date: Dec. 27, 2007

(65) Prior Publication Data
US 2011/0136888 A1    Jun. 9, 2011

(30) Foreign Application Priority Data

Jun. 21, 2006   (FR) ..................................... 0605540

(51) Int. Cl.
| | |
|---|---|
| *A01N 37/10* | (2006.01) |
| *A61K 31/235* | (2006.01) |
| *A61K 31/19* | (2006.01) |
| *C07C 331/00* | (2006.01) |
| *C07C 323/00* | (2006.01) |
| *C07C 381/00* | (2006.01) |
| *C07C 63/00* | (2006.01) |
| *C07C 65/00* | (2006.01) |
| *C07C 59/90* | (2006.01) |
| *C07C 62/32* | (2006.01) |
| *C07C 65/40* | (2006.01) |

(52) U.S. Cl. .......... 514/543; 514/517; 560/17; 562/405; 562/464

(58) Field of Classification Search ................ 514/543, 514/571; 562/405, 464; 560/17
See application file for complete search history.

(56) References Cited

U.S. PATENT DOCUMENTS

2010/0286276 A1   11/2010   Delhomel et al.

FOREIGN PATENT DOCUMENTS

| | | |
|---|---|---|
| CA | 2169187 A1 * | 2/1995 |
| DE | 2 149 070 | 4/1973 |
| DE | 41 21 849 | 1/1993 |
| DE | 43 27 365 | 2/1995 |

OTHER PUBLICATIONS

Vippagunta et al. Advanced Drug Delivery Reviews, 2001, vol. 48, pp. 3-26.*
Morishita S., et al., "Synthesis and Hypolilidaemic Activity of 2-Substituted Isobutyric Acid Derivatives", Journal of Medicinal Chemistry, vol. 31, No. 6, (Jun. 1988), pp. 1205-1209.
Labaudiniere R. et al., "Omega-[(Omega-Arylalkyl)Aryl]Alkanoic Acids: A New Class of Specific LTA4 Hydrolase Inhibitors", Journal of Medicinal Chemistry, vol. 35, No. 17, (1992), pp. 3156-3169.
Lan, He et al., "Synthesis and Biological Activity of Flavane Derivatives", Database CA [Online], Accession No. 2006:290724, (2006), 1 page.
International Search Report for PCT/EP2007/056224, mailed Oct. 25, 2007.
International Search Report issued in PCT/EP2007/056225, mailed Oct. 29, 2007.

* cited by examiner

*Primary Examiner* — Samira Jean-Louis
(74) *Attorney, Agent, or Firm* — Nixon & Vanderhye P.C.

(57) ABSTRACT

The present invention involves substituted 1,3-diphenylpropane derivatives, pharmaceutical compositions comprising them and the therapeutic uses thereof, in particular in the fields of human and animal health.

9 Claims, 28 Drawing Sheets

SEQUENCE LISTING

```
<160> NUMBER OF SEQ ID NOS: 12

<210> SEQ ID NO 1
<211> LENGTH: 22
<212> TYPE: DNA
<213> ORGANISM: artificial
<220> FEATURE:
<223> OTHER INFORMATION: forward primer PDK4

<400> SEQUENCE: 1
tactccactg ctccaacacc tg                                        22

<210> SEQ ID NO 2
<211> LENGTH: 20
<212> TYPE: DNA
<213> ORGANISM: artificial
<220> FEATURE:
<223> OTHER INFORMATION: reverse primer PDK4

<400> SEQUENCE: 2
gttcttcggt tccctgcttg                                           20

<210> SEQ ID NO 3
<211> LENGTH: 20
<212> TYPE: DNA
<213> ORGANISM: artificial
<220> FEATURE:
<223> OTHER INFORMATION: forward primer ApoCIII

<400> SEQUENCE: 3
ctcttggctc tcctggcatc                                           20

<210> SEQ ID NO 4
<211> LENGTH: 20
<212> TYPE: DNA
<213> ORGANISM: artificial
<220> FEATURE:
<223> OTHER INFORMATION: reverse primer ApoCIII

<400> SEQUENCE: 4
gcatcctgga ccgtcttgga                                           20

<210> SEQ ID NO 5
<211> LENGTH: 20
<212> TYPE: DNA
<213> ORGANISM: artificial
```

```
<220> FEATURE:
<223> OTHER INFORMATION: forward primer ACO

<400> SEQUENCE: 5
gaagccagcg ttacgaggtg                                              20

<210> SEQ ID NO 6
<211> LENGTH: 20
<212> TYPE: DNA
<213> ORGANISM: artificial
<220> FEATURE:
<223> OTHER INFORMATION: reverse primer ACO

<400> SEQUENCE: 6
tggagttctt gggacgggtg                                              20

<210> SEQ ID NO 7
<211> LENGTH: 24
<212> TYPE: DNA
<213> ORGANISM: artificial
<220> FEATURE:
<223> OTHER INFORMATION: forward primer UCP2

<400> SEQUENCE: 7
gtcggagata ccagagcact gtcg                                         24

<210> SEQ ID NO 8
<211> LENGTH: 20
<212> TYPE: DNA
<213> ORGANISM: artificial
<220> FEATURE:
<223> OTHER INFORMATION: reverse primer UCP2

<400> SEQUENCE: 8
cacatcaaca ggggaggcga                                              20

<210> SEQ ID NO 9
<211> LENGTH: 25
<212> TYPE: DNA
<213> ORGANISM: artificial
<220> FEATURE:
<223> OTHER INFORMATION: forward primer 36B4

<400> SEQUENCE: 9
catgctcaac atctcccccT tctcc                                        25

<210> SEQ ID NO 10
<211> LENGTH: 25
<212> TYPE: DNA
<213> ORGANISM: artificial
<220> FEATURE:
<223> OTHER INFORMATION: reverse primer 36B4

<400> SEQUENCE: 10
gggaaggtgt aatccgtctc cacag                                        25

<210> SEQ ID NO 11
<211> LENGTH: 22
<212> TYPE: DNA
<213> ORGANISM: artificial
<220> FEATURE:
<223> OTHER INFORMATION: forward primer 18S

<400> SEQUENCE: 11
cggacacgga caggattgac ag                                           22
```

```
<210> SEQ ID NO 12
<211> LENGTH: 20
<212> TYPE: DNA
<213> ORGANISM: artificial
<220> FEATURE:
<223> OTHER INFORMATION: reverse primer 18S

<400> SEQUENCE: 12
aatctcgggt ggctgaacgc                                            20
```

SUBSTITUTED 1,3-DIPHENYLPROPANE DERIVATIVES, PREPARATIONS AND USES THEREOF

This application is the U.S. national phase of International Application No. PCT/EP2007/056224, filed 21 Jun. 2007, which designated the U.S. and claims priority to France Application No. 0605540, filed 21 Jun. 2006, the entire contents of each of which are hereby incorporated by reference.

The present invention relates to substituted 1,3-diphenylpropane derivatives, pharmaceutical compositions comprising them and to the therapeutic uses thereof, in particular in the fields of human and animal health.

The inventors have shown, surprisingly, that the compounds according to the present invention have intrinsic PPAR agonist properties.

The molecules described in this invention are therefore of particular interest in the treatment of metabolic syndrome complications, insulin resistance, diabetes, dyslipidemias, atherosclerosis, cardiovascular disease, obesity, hypertension, inflammatory diseases (asthma, etc.), neurodegenerative diseases (Alzheimer's disease, etc.), cancer, etc., as well as reducing the global risk. The compounds according to this invention are to be used preferably for treating dyslipidemias.

Diabetes, obesity, and dyslipidemias (high plasma LDL-cholesterol and triglycerides levels, low HDL-cholesterol levels, etc.) are some of the clearly-identified cardiovascular risk factors which may predispose a person to develop cardiovascular diseases (Mensah M, 2004). Also to be considered are lifestyle risk factors such as tobacco use, a sedentary lifestyle, and an unbalanced diet. These factors have a synergetic effect: the simultaneous presence of several of these factors dramatically increases cardiovascular risk. Therefore, a global risk of cardiovascular disease deserves to be addressed. In 2004, the prevalence rate of dyslipidemias reached 43.6% of the population in industrialized countries. The sharp increase of diabetics is currently making diabetes an ever more important factor in the epidemiology of cardiovascular diseases: it is estimated that, by 2010, 7.6% of the population will be diabetic (Fox-Tucker J, 2005).

According to the International Atherosclerosis Society (International Atherosclerosis Society, 2003), cardiovascular disease is the primary cause of death in industrialized countries and is becoming ever more prevalent in developing countries. The principal cardiovascular diseases are heart disease, cerebral ischemia, and peripheral arterial diseases.

These data therefore justify taking vigorous measures to significantly reduce cardiovascular morbidity and mortality rates and reveal the necessity of finding effective treatments, in conjunction with life style modification. Taking into account the risk factors for cardiovascular diseases and their consequences, this is a worldwide emergency.

The compounds according to the invention, because of their PPAR agonist properties, are of particular interest for the treatment of pathologies related to deregulations of lipid and/or glucid metabolism, such as diabetes, obesity, dyslipidemias, or inflammation, as well as for reducing the global cardiovascular risks.

PPARs ($\alpha$, $\gamma$ and $\delta$) are known to be involved in this type of pathologies (Kota B P et al., 2005): ligands and receptors are therefore marketed for treatment of these pathologies (Lefebvre P et al., 2006) and various PPAR modulators, agonist or antagonist, selective or non-selective, are currently in high development. A PPAR modulator having advantageous effects on insulin resistance, obesity, dyslipidemias, hypertension, and/or inflammation could be used in the treatment of metabolic syndrome (or syndrome X) (Liu Y and Miller A, 2005).

The family of PPARs includes three isoforms, known as $\alpha$, $\gamma$ and $\delta$ (also known as $\beta$), each being coded by a different gene. These receptors belong to the nuclear receptor and transcription factor superfamily, which are activated upon contact with certain fatty acids and/or their lipid metabolites. Activated PPARs form heterodimers with 9-cis retinoic acid receptors (RXR or Retinoid X Receptor) and bind to specific response elements (PPRE or Peroxisome Proliferator Response Element) of the promoter of target genes, thus allowing a control of the transcription.

PPAR$\alpha$ controls lipid metabolism (hepatic and muscular) and homeostasis of glucose, influences intracellular metabolism of lipids and glucids by controlling directly the transcription of genes coding for proteins involved in lipid homeostasis, has anti-inflammatory and antiproliferative effects, and prevents pro-atherogenic effects of the accumulation of cholesterol in macrophages by stimulating cholesterol efflux (Lefebvre P, Chinetti G, Fruchart J C and Staels B, 2006). Fibrates (fenofibrate, bezafibrate, ciprofibrate, gemfibrozil), via PPAR$\alpha$, are used in clinical medicine to treat certain dyslipidemias by lowering triglycerides and raising HDL (High Density Lipoprotein) levels.

PPAR$\gamma$ is a key regulator of adipogenesis. Additionally, it is involved in lipid metabolism of mature adipocytes, glucose homeostasis, and especially insulin resistance, inflammation, macrophage cholesterol accumulation, and cellular proliferation (Lehrke M and Lazar M A, 2005). Therefore, PPAR$\gamma$ plays a role in the pathogenesis of obesity, insulin resistance, and diabetes. Thiazolidinediones (Rosiglitazone, Troglitazone, etc.) are PPAR$\gamma$ ligands used in the treatment of type 2 diabetes.

There are PPARδ ligands (L-165041, GW501516 currently in clinical development), but no PPARδ ligand is currently being used as a drug. This receptor is, however, an attractive goal for the development of useable drugs for treatment of dyslipidemias, atherosclerosis, obesity, and insulin resistance: PPARδ is in fact involved in lipid and glucose metabolism control, energy balance, neurodegeneration, obesity, formation of macrophage foam cells, and inflammation (Gross B et al., 2005).

Beyond the direct role PPAR ligands play in the regulation of lipid and glucid metabolism, these molecules have a pleiotropic action spectrum due to the great diversity of PPAR target genes. These multiple properties make PPARs interesting therapeutic targets regarding the treatment of diseases such as atherosclerosis, cerebral ischemia, hypertension, diseases connected to neovascularisation (retinopathy, diabetes, etc.), inflammatory and auto-immune diseases (Crohn's disease, psoriasis, multiple sclerosis, asthma, etc.), neoplastic diseases (carcinogenesis, etc.), neurodegenerative diseases, complications associated with metabolic syndrome, insulin resistance, diabetes, dyslipidemias, cardiovascular disease, obesity, etc., as well as for reducing the global risk.

The compounds according to the invention, because of their PPAR agonist properties, are an advantageous therapeutic tool for improving the treatment of pathologies related to deregulation of lipid and/or glucid metabolism, especially dyslipidemias, as well as reducing the global cardiovascular risk.

More generally, by acting simultaneously on several regulation processes, the compounds according to the invention are an advantageous therapeutic means for the treatment of complications associated with metabolic syndrome (the features of which are obesity, in particular abdominal obesity, an abnormal concentration of blood lipids (high triglyceride level and/or low HDL cholesterol level (dyslipidemy)), elevated glycemia and/or insulin resistance, and hypertension), atherosclerosis, cardiovascular disease, insulin resistance, obesity, hypertension, diabetes, dyslipidemias, cardiovascular disease, inflammatory disease (asthma, etc.), neurodegenerative pathologies (Alzheimer's disease, etc.), cancer, etc., as well as reducing global risk.

The present invention is directed to compounds, derived from 1,3-diphenylpropane derivative compounds, having the following general formula:

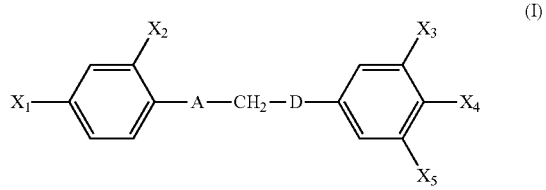

(I)

in which:
X1 represents a R1 or G1-R1 group;
X2 represents a halogen atom, a R2 or G2-R2 group;
X3 represents a R3 or G3-R3 group;
X4 represents a halogen atom, a R4 or G4-R4 group;
X5 represents a R5 or G5-R5 group;
R1 representing a hydrogen atom or a non-halogenated alkyl group;
R2 representing a hydrogen atom or a non-halogenated alkyl group;
R3, R4, and R5, identical or different, representing an atom of hydrogen or an alkyl group substituted or not by one or several group 1 or group 2 substituents;
G1, G2, G3, G4, and G5, identical or different, representing an atom of oxygen or sulfur;
with at least one group among X3, X4, or X5 responding to the R3, G3R3, R4, G4R4, R5, or G5R5, in which:
G3, G4, and G5 as previously described, and
R3, R4, and R5, identical or different, representing an alkyl group substituted by one or several group 1 or group 2 substituents;
A represents:
  (i) a CR6R7 group, in which
    R6 and R7, identical or different, represent a hydrogen atom, a hydroxyl group, an alkyl group, or a OR8 group, R8 being as defined below.
  (ii) a carbonyl group (CO),
  (iii) an oxime group (C=N—O—H) or oxime ether (C=N—O—R8),
    R8 representing an alkyl group, substituted or not by an aryl or cycloalkyl group;
D represents:
  (i) a carbon atom linked to two hydrogen atoms (CH$_2$),
  (ii) a carbon atom linked to both a hydrogen atom and G2 so as to form an oxygenated or sulfured heterocycle;
substituents of group 1 are chosen among —COOR9 and —CONR9R10;
substituents of group 2 are chosen among —SO$_3$H and —SO$_2$NR9R10;
R9, R10, and R5, identical or different, representing an atom of hydrogen or an alkyl radical substituted or not by at least one group 1 or group 2 substituent;
with the exception of compounds of general formula (I) in which A represents a —CR6R7 group, R6 and R7 representing a hydrogen atom, and in which at least three of groups X1, X2, X3, X4 and/or X5 represent hydrogen atoms; their stereoisomers (diastereoisomers, enantiomers), pure or mixed, racemic mixtures, geometrical isomers, tautomers, salts, hydrates, solvates, solid forms as well as their mixtures.

In the context of this invention, the term "alkyl" designates a hydrocarbon radical that is saturated, linear, branched, or cyclic, halogenated or not, having particularly from 1 to 24, and preferably 1, 2, 3, 4, 5, 6, 7, 8, 9, or 10, carbon atoms, such as methyl, trifluoromethyl, ethyl, n-propyl, isopropyl, n-butyl, isobutyl, tertiobutyl, sec-butyl, pentyl, neopentyl, n-hexyl, or cyclohexyl.

The term "cycloalkyl" designates an alkyl group as defined above and forms at least one cycle (e.g. cycloalkyl groups having 3 to 8 carbon atoms: cyclopropyl, cyclobutyl, cyclopentyl, cyclohexyl, cycloheptyl, and cyclooctyl).

The term "alkyloxy" refers to an alkyl chain linked to the molecule by means of an oxygen atom (an ether bond). The alkyl chain corresponds to the previously expressed definition. Methoxy, trifluoromethoxy, ethoxy, n-propyloxy, isopropyloxy, n-butoxy, iso-butoxy, tertio-butoxy, sec-butoxy, or hexyloxy can be given as examples.

The term "aryl" refers to aromatic groups comprising preferably from 5 to 14 carbon atoms, advantageously 6 to 14 carbon atoms, possibly interrupted by one or several heteroatoms selected among N, O, S or P (more specifically call "heteroaryle"). They are generally mono- or bi-cyclical and comprise advantageously from 6 to 14 carbon atoms, such as phenyl, α-naphtyl, β-naphtyl, anthracenyl or fluorenyl.

The term "oxygenated or sulfured heterocycle" designates a cycloalkyl group as defined above interrupted by one or several heteroatoms chosen among O and S. Thiopyrane or pyrane can be cited as examples.

By halogen atom, an atom of bromine, chlorine, fluorine or iodine is understood.

A non-halogenated alkyl radical is an alkyl radical as defined above which presents no halogen atom.

Accordingly, the compounds of general formula (I) which present at least one of groups X3, X4 or X5 corresponding to a R3, G3R3, R4, G4R4, R5 or G5R5 formula, in which:
G3, G4, and G5 are such as previously described, and
R3, R4, and R5, identical or different, represent an alkyl group substituted by one or several group 1 or group 2 substituents;
have therefore at least one of the groups R3, R4 and R5 of X3, X4 or X5 respectively representing an alkyl group substituted by one or several group 1 or group 2 substituent(s).

One particular aspect of the invention concerns compounds of general formula (I) in which A represents a carbonyl group (CO).

Another particular aspect of the invention concerns compounds of general formula (I) in which A represents an oxime group (C=N—O—H) or oxime ether (C=N—O—R8), R8 representing an alkyl group substituted or not by an aryl or cycloalkyl group. Preferably, R8 represents a methyl group.

Another particular aspect of the invention concerns compounds of general formula (I) in which A represents a CH$_2$ group.

Another particular aspect of the invention concerns compounds of general formula (I) in which A does not represent a CH$_2$ group.

Another particular aspect of the invention concerns compounds of general formula (I) in which A represents a —CR6R7 group, R6 representing a hydrogen atom and R7 representing a hydroxyl group, alkyl group, or a —OR8 group, R8 representing an alkyl group, substituted or not by an aryl or cycloalkyl group.

Preferably, the invention concerns compounds of general formula (I) in which A represents a —CR6R7 group, R6 representing a hydrogen atom and R7 representing a hydroxyl group.

Another preferential aspect of the invention concerns compounds of general formula (I) in which A represents a —CR6R7 group, R6 representing a hydrogen atom and R7 representing a —OR8 group, R8 being such as defined above. Preferably, R8 represents an alkyl group comprising preferably 1, 2, 3 or 4 carbon atoms. Even more preferably, R8 represents an alkyl group substituted by an aryl or cycloalkyl group, said aryl or cycloalkyl group comprising specifically 6 carbon atoms.

Another particular aspect of the invention concerns compounds of general formula (I) in which A represents a —CR6R7 group, R6 and R7, identical or different, representing a hydroxyl group, alkyl group, or a —OR8 group, R8 representing an alkyl group, substituted or not by an aryl or cycloalkyl group.

Another specific subject-matter of the invention concerns compounds of general formula (I) in which X3 and X5, identical or different, represent respectively a R3 and R5 group, specifically with R3 and R5 representing a hydrogen atom.

Another specific subject-matter of the invention concerns compounds of general formula (I) in which X3 and X5, identical or different, represent respectively a R3 and R5 group, R3 and R5, identical or different, representing an alkyl group substituted or not by one or several group 1 or group 2 substituent(s), as previously defined.

Preferably, X3 and X5, identical or different, represent respectively a R3 and R5 group, R3 and R5, identical or different, representing a non-substituted alkyl group, comprising preferably 1, 2, 3 or 4 carbon atoms. Even more preferably, X3 and X5, identical or different, represent a methyl group.

Another particular aspect of the invention concerns compounds of general formula (I) in which X3 and X5, identical or different, represent respectively a
G3R3 or G5R5 group,
G3 and G5 being such as previously described, and
R3 and R5, identical or different, representing a hydrogen atom.

Another particular aspect of the invention concerns compounds of general formula (I) in which X3 and X5, identical or different, represent respectively a G3R3 or G5R5 group,
G3 and G5 being such as previously described, and
R3 and R5, identical or different, representing an alkyl group substituted or not by one or several group 1 or group 2 substituents, as previously defined.

Another particular aspect of the invention concerns compounds of general formula (I) in which X3 and X5, identical or different, represent respectively a G3R3 or G5R5 group,
G3 and G5 being such as previously described, and
R3 and R5, identical or different, representing an alkyl group substituted by one or several group 1 or group 2 substituents, as previously defined.

Another particular aspect of the invention concerns compounds of general formula (I) in which X4 represents a halogen atom (bromine, chlorine, fluorine, iodine).

Another particular aspect of the invention concerns compounds of general formula (I) in which X4 represents a R4 or G4-R4 group,
G4 being such as previously defined, and
R4 representing a hydrogen atom.

Another particular aspect of the invention concerns compounds of general formula (I) in which X4 represents a R4 or G4-R4 group,
G4 being such as previously defined, and
R4 representing an alkyl group substituted or not by one or several group 1 or group 2 substituents, as previously defined.

Another particular aspect of the invention concerns compounds of general formula (I) in which X4 represents a R4 or G4-R4 group,
G4 being such as previously defined, and
R4 representing an alkyl group substituted by one or several group 1 or group 2 substituents, such as previously defined. Preferably, G4 represents an oxygen atom and/or R4 represents an alkyl group substituted by a group 1 substituent, in particular —COOH. Even more preferably, X4 represents a —OC(CH$_3$)$_2$COOH, —OCH$_2$COOH or —SC(CH$_3$)$_2$COOH group.

Another particular subject-matter of the invention concerns compounds of general formula (I) in which only one of the X3, X4 and X5 groups represents a R3, R4, R5, G3R3, G4R4 or G5R5 group,
G3, G4, and G5 being such as previously described, and
R3, R4 or R5, identical or different, representing an alkyl group substituted by one or several group 1 or group 2 substituent(s), as previously defined.

Another particular subject-matter of the invention concerns compounds of general formula (I) in which only X4 of the X3, X4, and X5 groups represents a R4 or G4R4,
G4 being such as previously defined, and
R4 representing an alkyl group substituted by one or several group 1 or group 2 substituents, as previously defined.

Another particular subject-matter of the invention concerns compounds of general formula (I) in which two or three of the X3, X4 and X5 groups represent a R3, R4, R5, G3R3, G4R4 or G5R5 group,
G3, G4, and G5 being such as previously described, and
R3, R4, and R5, identical or different, representing an alkyl group substituted by one or several group 1 or group 2 substituent(s), as previously defined.

Another particular aspect of the invention concerns compounds of general formula (I) in which G3, G4 and/or G5 represent(s) an oxygen atom.

Preferably, the invention concerns compounds of general formula (I) in which only one of the X3, X4 or X5 groups corresponds to the G3R3, G4R4 or G5R5 formula,
G3, G4, and G5 representing an oxygen atom, and
R3, R4 or R5, identical or different, representing an alkyl group substituted by one or several group 1 or group 2 substituent(s), as previously defined.

Even more preferably, the invention concerns compounds of general formula (I) in which only X4, among X3, X4, and X5, corresponds to the G4R4 formula,
G4 representing a hydrogen atom, and
R4 representing an alkyl group substituted by one or several group 1 or group 2 substituents, as previously defined.

Another preferential aspect of the invention concerns compounds of general formula (I) in which two or three of the X3, X4 or X5 groups correspond to the G3R3, G4R4 or G5R5 formula,
G3, G4, and G5 representing an oxygen atom, and
R3, R4, and R5 representing an alkyl group substituted by one or several group 1 or group 2 substituent(s), as previously defined.

A particular aspect of the invention concerns compounds of general formula (I) in which the substituent is chosen from among group 1 substituents. Preferably, the group 1 substituent is a —COOR9 type, R9 being such as previously defined and representing preferably a hydrogen atom or an alkyl group comprising 1, 2, 3, 4, 5 or 6 carbon atoms.

A particular aspect of the invention concerns compounds of general formula (I) in which only one of the X3, X4 or X5 groups corresponds to the formula —OC(CH₃)₂COOR9, R9 being such as previously defined and representing preferably a hydrogen atom or an alkyl group comprising 1, 2, 3, 4, 5 or 6 carbon atoms.

Even more preferably, X4 represents a —OC(CH₃)₂COOR9 group, R9 being such as previously defined and representing preferably a hydrogen atom or an alkyl group comprising 1, 2, 3, 4, 5 or 6 carbon atoms.

One particular aspect of the invention concerns compounds of general formula (I) in which X1 represents a R1 or G1 R1 carbonyl group, G1 being such as previously defined, and R1 representing a non-halogenated alkyl group.

For example, X1 represents a —OCH₂CH₂CH₃, —SCH₂CH₂CH₃ group or an alkyl group presenting 7 carbon atoms.

Preferably, R1 represents a non-halogenated alkyl group comprising 1, 2 or 3 carbon atoms.

Even more preferably, X1 represents a —CH₃, —SCH₃, —OCH₃ group.

One particular aspect of the invention concerns compounds of general formula (I) in which X1 represents a hydrogen atom. Preferably, when X1 represents a hydrogen atom, X2 is different from a hydrogen atom.

One particular aspect of the invention concerns compounds of general formula (I) in which X2 represents a hydrogen atom. Preferably, when X2 represents a hydrogen atom, X1 is different from a hydrogen atom.

A particular aspect of the invention concerns compounds of general formula (I) in which X2 represents a halogen atom (bromine, chlorine, fluorine, iodine).

A particular subject-matter of the invention concerns compounds of general formula (I) in which X2 represents a R2 or G2R2 group, R2 and G2 being such as previously described. Preferably, R2 represents a hydrogen atom, a CF₃ group or an alkyl group comprising 1, 2, 3, 4, 5, 6, 7 or 8 carbon atoms. Even more preferably, X2 represents a —OR group, R representing an alkyl group, —CF₃, —OCF₃, —OH.

A particular aspect of the invention concerns compounds of general formula (I) in which D represents a CH₂ group.

Another particular subject-matter of the invention concerns compounds of general formula (I) in which G2 and D form an oxygenated or sulfured heterocycle so as to form the following formula compound:

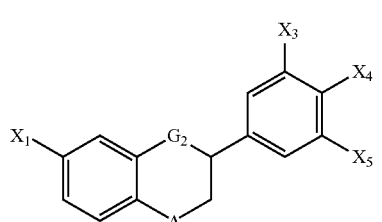

(II)

Preferably, G2 represents a sulfur atom in general formula (II).

In accordance with particular embodiment of the invention, the preferred compounds are indicated below:

Compound 2: 2-[2,6-dimethyl-4-[3-[4-(methylthio)phenyl]-3-oxo-propyl]phenoxy]-2-methylpropanoic acid

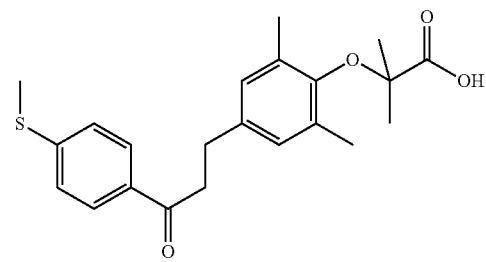

Compound 2: 2-[2,6-dimethyl-4-[3-[2-(hexyloxy)phenyl]-3-oxo-propyl]phenoxy]-2-methylpropanoic acid

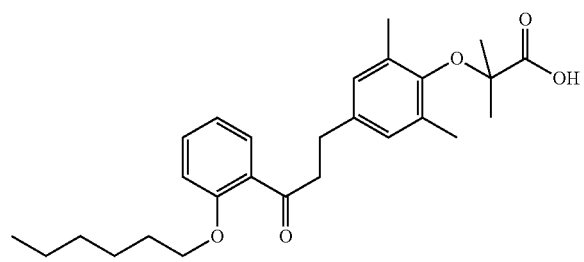

Compound 3: 2-[2,6-dimethyl-4-[3-[4-(methylthio)phenyl]-3-benzyloxypropyl]phenoxy]-2-methylpropanoic acid

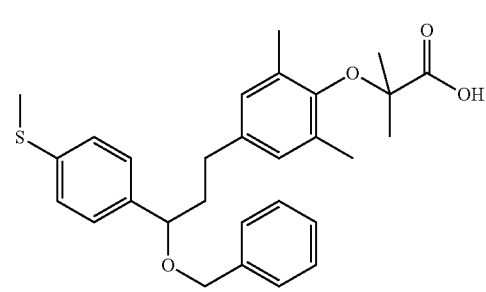

Compound 4: 2-[2,6-dimethyl-4-[3-[4-(methylthio) phenyl]-3-hydroxypropyl]phenoxy]-2-methylpropanoic acid

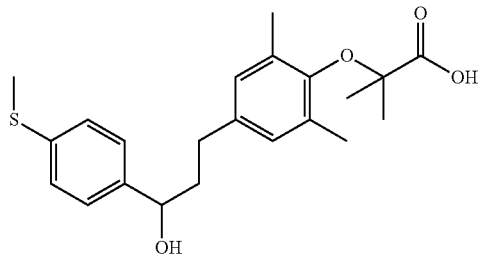

Compound 5: 2-[2,6-dimethyl-4-[3-[4-(methylthio) phenyl]-3-methoxyimino-propyl]phenoxy]-2-methylpropanoic acid

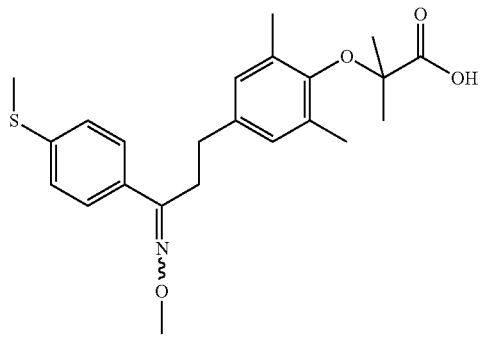

Compound 6: 2-[2,6-dimethyl-4-[3-[4-(methoxy) phenyl]-3-oxo-propyl]phenoxy]-2-methylpropanoic acid

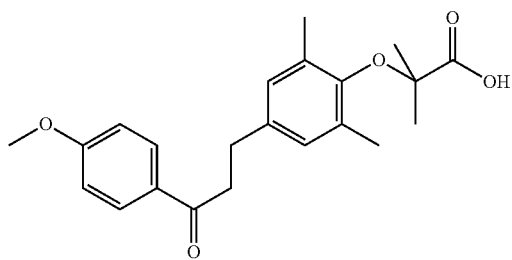

Compound 7: 2-[2,6-dimethyl-4-[3-[4-(methylthio) phenyl]-3-oxo-propyl]phenoxy]-2-methylethanoic acid

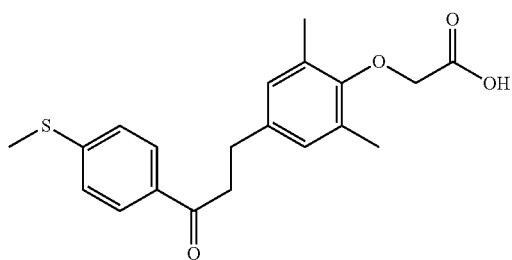

Compound 8: 2-[2,6-dimethyl-4-[3-[4-(propyloxy) phenyl]-3-oxo-propyl]phenoxy]-2-methylpropanoic acid

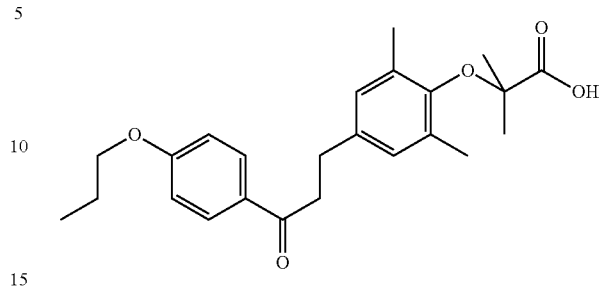

Compound 9: 2-[2-methyl-4-[3-[4-(heptyl)phenyl]-3-oxo-propyl]phenoxy]-2-methylpropanoic acid

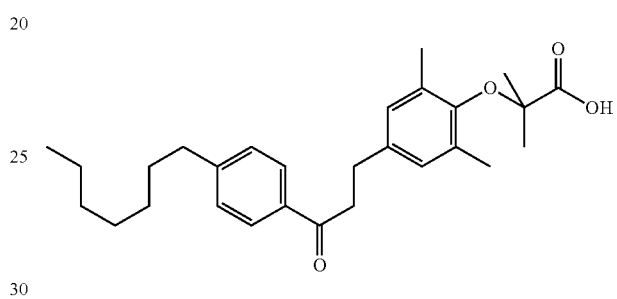

Compound 10: 2-[2,6-dimethyl-4-[3-[4-(methylthio) phenyl]-3-ethyloxypropyl]phenoxy]-2-methylpropanoic acid

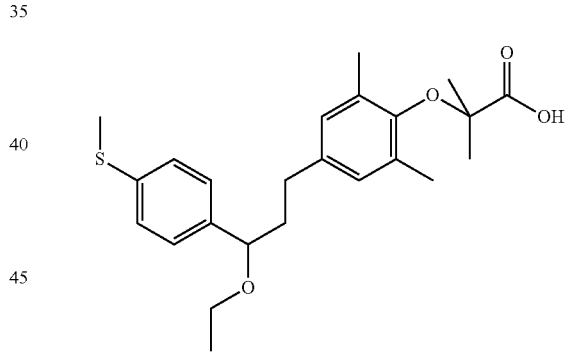

Compound 11: 2-[2,6-dimethyl-4-[3-[2-(trifluoromethyl)phenyl]-3-oxo-propyl]phenoxy]-2-methylpropanoic acid

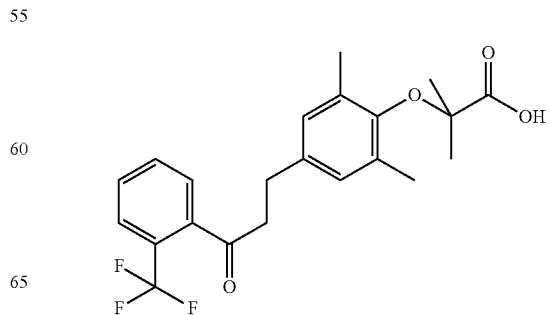

Compound 12: 2-[2,6-dimethyl-4-[3-[4-(methylthio) phenyl]propyl]phenoxy]-2-methylpropanoic acid

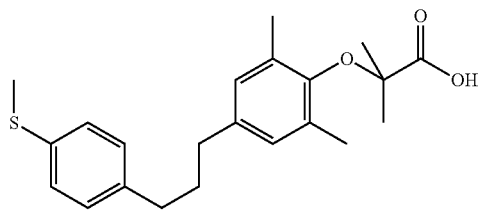

Compound 13: 2-[2,6-dimethyl-4-[3-[4-(methylthio) phenyl]-3-oxo-propyl]phenoxy]-2-methyl propanoic acid isopropyl ester

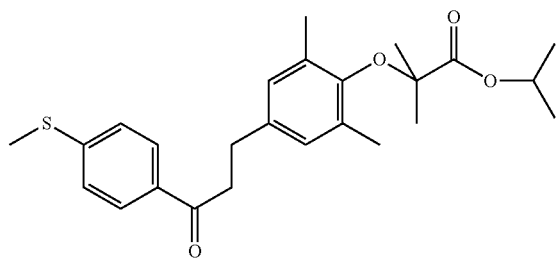

Compound 14: 2-[2,6-dimethyl-4-[3-[4-(methylthio)phenyl]-3-hydroxyimino-propyl]phenoxy]-2-methylpropanoic acid

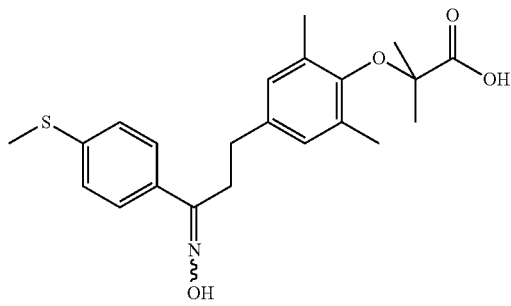

Compound 15: 2-[2,6-dimethyl-4-[3-[4-(propyloxy) phenyl]-3-hydroxypropyl]phenoxy]-2-methylpropanoic acid

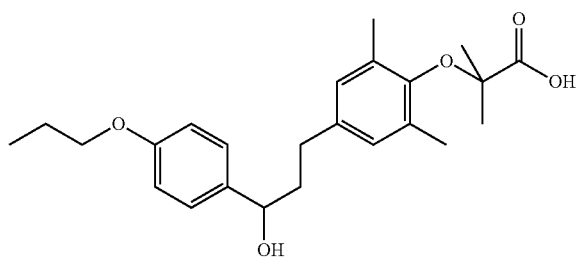

Compound 16: 2-[2,6-dimethyl-4-[3-[2-(trifluoromethoxy)phenyl]-3-oxo-propyl]phenoxy]-2-methylpropanoic acid

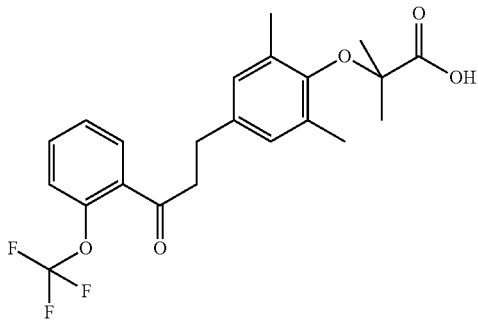

Compound 17: 2-[2,6-dimethyl-4-[3-[4-(methylthio) phenyl]-3-methoxypropyl]phenoxy]-2-methylpropanoic acid

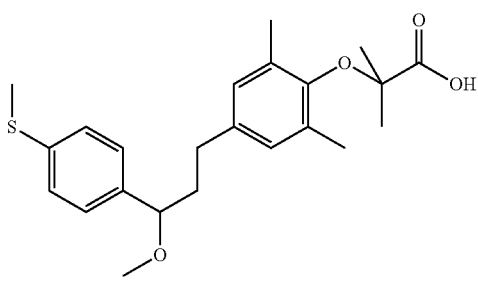

Compound 18: 2-[2,6-dimethyl-4-[2,3-dihydro-4H-1-benzothiopyran-4-one-2-yl]phenoxy]-2-methylpropanoic acid

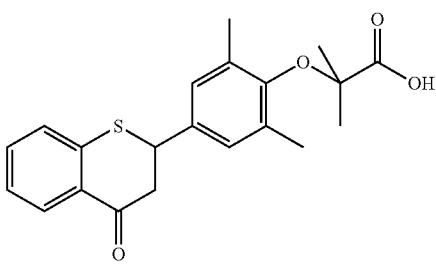

Compound 19: 2-[2-methyl-4-[3-[4-(propylthio)phenyl]-3-oxo-propyl]phenoxy]-2-methylpropanoic acid

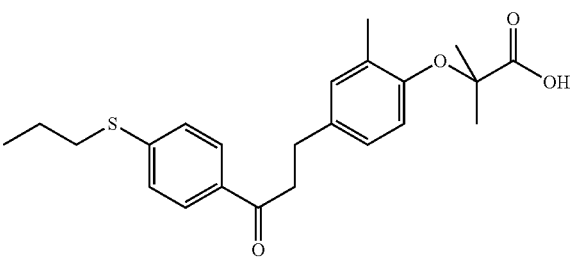

Compound 20: 2-[3-[3-[4-(methylthio)phenyl]-3-oxo-propyl]phenoxy]-2-methylpropanoic acid

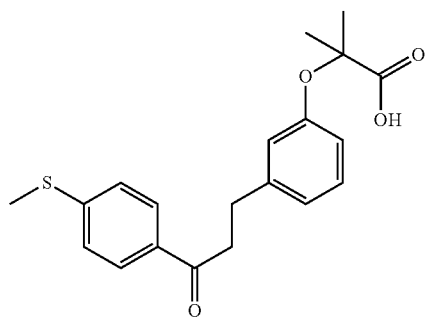

Compound 21: 2-[4-[3-[4-(methylphenyl]-3-oxo-propyl]phenoxy]-2-methylpropanoic acid

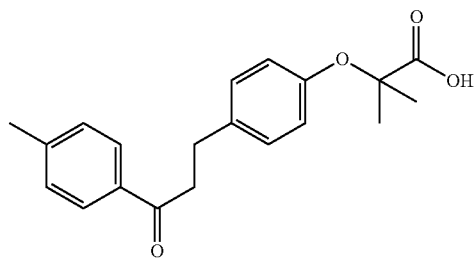

Compound 22: 2-[2,6-dimethyl-4-[3-[4-(methylthio)pheny]-3-cyclohexylmethoxypropyl]phenoxy]-2-methylpropanoic acid

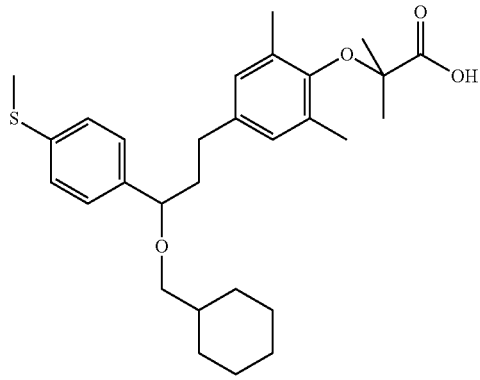

Compound 23: 2-[2,6-dimethyl-4-[3-[4-(methylthio)phenyl]-3-butyloxypropyl]phenoxy]-2-methylpropanoic acid

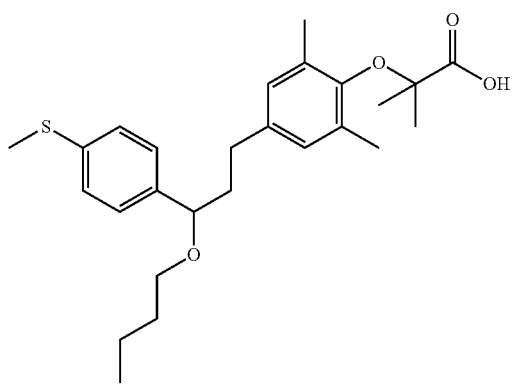

Compound 24: 2-[2,6-dimethyl-4-[3-[4-(methylthio)phenyl]-3-isopropyloxypropyl]phenoxy]-2-methylpropanoic acid

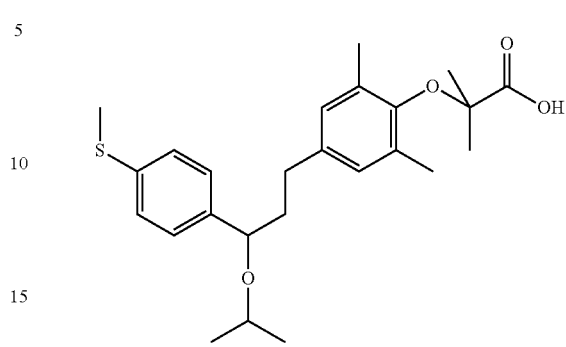

Compound 25: 2-[2,6-dimethyl-4-[3-[4-(methylthio)phenyl]-3-cyclohexylethyloxypropyl]phenoxy]-2-methylpropanoic acid

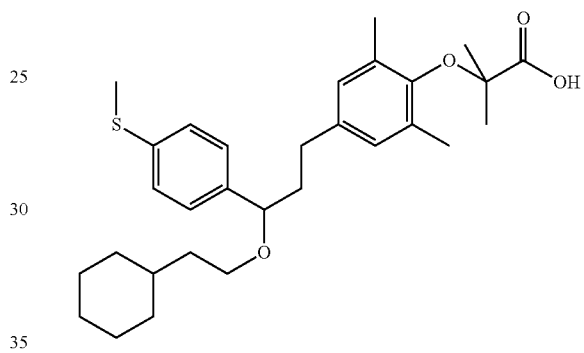

Even more preferably, the invention concerns the following compounds:
Compound 1: 2-[2,6-dimethyl-4-[3-[4-(methylthio)phenyl]-3-oxo-propyl]phenoxy]-2-methylpropanoic acid;
Compound 2: 2-[2,6-dimethyl-4-[3-[2-(hexyloxy)phenyl]-3-oxo-propyl]phenoxy]-2-methylpropanoic acid;
Compound 8: 2-[2,6-dimethyl-4-[3-[4-(propyloxy)phenyl]-3-oxo-propyl]phenoxy]-2-methylpropanoic acid;
Compound 13: 2-[2,6-dimethyl-4-[3-[4-(methylthio)phenyl]-3-oxo-propyl]phenoxy]-2-methylpropanoic acid isopropyl ester;
Compound 16: 2-[2,6-dimethyl-4-[3-[2-(trifluoromethoxy)phenyl]-3-oxo-propyl]phenoxy]-2-methylpropanoic acid.

The compounds according to the invention include their stereoisomers (diastereoisomers, enantiomers), pure or mixed, their racemic mixtures, their geometrical isomers, their tautomers, their salts, their hydrates, their solvates, their solid forms, and mixtures thereof.

The compounds according to the invention can contain one or several asymmetrical centers. This invention includes stereoisomers (diastereoisomers, enantiomers), pure or mixed, as well as racemic mixtures and geometrical isomers. When an enantiomerically pure (or enriched) product is desired, it can be obtained either by purification of the final product or chiral intermediates, or by asymmetrical synthesis following the typical methods known by one of ordinary skill in the art (for example, by using reactives and chiral catalysts). Some compounds according to the invention can have different stable tautomeric forms and all these forms as well as their mixtures are included in the invention.

The present invention also concerns "pharmaceutically acceptable" salts of compounds according to the invention.

Generally, this term designates slightly- or non-toxic salts obtained from organic or inorganic bases or acids. These salts can be obtained during the final purification step of the compound according to the invention or by incorporating the salt into the previously purified compound.

Some compounds according to the invention and their salts could be stable in several solid forms. The present invention includes all the solid forms of the compounds according to the invention which includes amorphous, polymorphous, mono- and poly-crystalline forms.

The compounds according to the invention can exist in free form or in solvated form, for example with pharmaceutically acceptable solvents such as water (hydrates) or ethanol.

Compounds according to the invention labelled with one or more isotopes are also included in the invention: these compounds are structurally identical but different by the fact that at least one atom of the structure is replaced by an isotope (radioactive or not). Examples of isotopes that can be included in the structure of the compounds according to the invention can be chosen from hydrogen, carbon, oxygen, and sulfur such as $^2H$, $^3H$, $^{13}C$, $^{14}C$, $^{18}O$, $^{17}O$, $^{35}S$ respectively. Radioactive isotopes are particularly preferable since they are easy to prepare and detect within the scope of in vivo bioavailability studies of the substances. Heavy isotopes (such as $^2H$) are particularly preferred because of their use as internal standards in analytical studies.

The present invention also concerns a process of synthesis of compounds of general formula (I) as previously defined.

The process according to the invention comprises:
a step of mix (i) in a basic or acidic medium of at least a compound of formula (A) with at least a compound of formula (B):

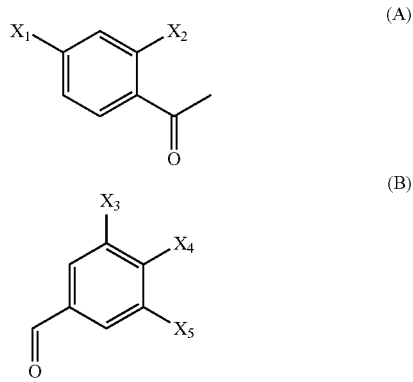

In which X1, X2, X3, X4, and X5 have the previously given definitions,
then (ii) a reduction step of the resulting compounds,
and eventually (iii) an introduction step allowing the linking of functional groups. The experimental conditions for step (i) in an acidic or basic medium and for step (ii) are easy to implement for the person skilled in the art and may vary greatly. The procedures of the syntheses can be particularly those described under "examples" in this invention.

The mix of the two compounds is advantageously performed stoichiometrically. This is preferably done at room temperature (between about 18° C. and 25° C.) and at normal atmospheric pressure.

In a basic medium, the reaction takes place preferably in the presence of a strong base, such as an alkali metal hydroxide, like sodium hydroxide or an alkali metal alcoholate like sodium ethylate.

In an acidic medium, the reaction takes place preferably in the presence of a strong acid, such as hydrochloric acid.

The resulting compounds can be isolated by classic methods of one of ordinary skill in the art. They could then be used, for example, as medicines or cosmetic products.

Another subject-matter of the present invention concerns compounds such as above described as medicines.

Another subject-matter of this invention concerns a pharmaceutical composition comprising, in a pharmaceutically acceptable support, at least one compound as above-described, possibly in association with one or several other therapeutic and/or cosmetic active ingredients. It is preferably a pharmaceutical composition for the treatment of complications associated with metabolic syndrome, insulin resistance, diabetes, dyslipidemias, atherosclerosis, cardiovascular diseases, obesity, hypertension, inflammatory diseases (asthma, etc.), neurodegenerative pathologies (Alzheimer's disease, etc.), or cancer, etc. The pharmaceutical composition according to the invention is preferably used for treating dyslipidemias.

It is preferably a pharmaceutical composition for treating cardiovascular risk factors related to a deregulation of lipid and/or glucids metabolism (hyperlipidemias, type II diabetes, obesity, etc.) by reducing the global risk.

Another subject-matter of the invention concerns a nutritional composition including at least one compound as above described.

Another subject-matter of the invention concerns the use of at least one compound as previously described for the preparation of pharmaceutical compositions intended for treating multiple pathologies, particularly the ones related to metabolism disorders (e.g. dyslipidemias). More generally, the subject-matter of the invention concerns the use of at least one compound previously described for the preparation of pharmaceutical compositions intended for treating the cardiovascular disease risk factors related to deregulations of lipid and/or carbohydrate metabolism and thus, in order to reduce the global risk.

For example (but not limitatively), the compounds according to the invention can be advantageously administered in combination with other therapeutic and/or cosmetic agents, currently available in the market or in development, such as:
anti-diabetics: secretagogues (sulfonylurea (glibenclamide, glimepiride, gliclazide, etc.) and glinides (repaglinide, nateglinide, etc.)), alpha-glucosidase inhibitors, PPARγ agonists (thiazolidinediones such as rosiglitazone, pioglitazone), mixed PPARα/γ agonists (tesaglitazar, muraglitazar), pan-PPARs (compounds that simultaneously activate the 3 PPAR isoforms), biguanides (metformin), Dipeptidyl Peptidase IV inhibitors (MK-431, vildagliptin), Glucagon-Like Peptide-1 (GLP-1) agonists (exenatide), etc.
insulin.
lipid-lowering and/or cholesterol-lowering molecules: fibrates (fenofibrate, gemfibrozil), HMG CoA reductase or hydroxylmethylglutaryl Coenzyme A reductase inhibitors (statins such as atorvastatin, simvastatin, fluvastatin), cholesterol absorption inhibitors (ezetimibe, phytosterols), CETP or Cholesterol Ester Transfer Protein inhibitors (torcetrapib), ACAT or acyl-coenzyme A cholesterol acyltransferase inhibitors (avasimibe, eflucimibe), MTP (Microsomal Triglyceride Transfer Protein) inhibitors, sequestering agents of biliary acids (cholestyramine), vitamin E, polyunsaturated fatty acids, omega-3 fatty acids, nicotinic acid derivatives (niacin), etc.

anti-hypertensive agents and hypotensive agents: ACE (Angiotensin-Converting Enzyme) inhibitors (captopril, enalapril, ramipril or quinapril), angiotensin II receptor antagonists (losartan, valsartan, telmisartan, eposartan, irbesartan, etc.), beta blockers (atenolol, metoprolol, labetalol, propranolol), thiazide and non-thiazide diuretics (furosemide, indapamide, hydrochlorthiazide, anti-aldosterone), vasodilators, calcium channel blockers (nifedipine, felodipine or amlodipine, diltiazem or verapamil), etc.

anti-platelet agents: Aspirin, Ticlopidine, Dipyridamole, Clopidogrel, Flurbiprofen, etc.

anti-obesity agents: Sibutramine, lipase inhibitors (orlistat), PPARδ, cannabinoid CB1 receptor antagonists (rimonabant), etc.

anti-inflammatory agents: for example, corticoids (prednisone, betamethasone, dexamethasone, prednisolone, methylprednisolone, hydrocortisone, etc.), NSAIDs or non-steroidal anti-inflammatory drugs derived from indole (indomethacin, sulindac), NSAIDs (non-steroidal anti-inflammatory drugs) of the arylcarboxylic group (tiaprofenic acid, diclofenac, etodolac, flurbiprofen, ibuprofen, ketoprofen, naproxen, nabumetone, alminoprofen), NSAIDs (non-steroidal anti-inflammatory drugs) derived from oxicam (meloxicam, piroxicam, tenoxicam), NSAIDs (non-steroidal anti-inflammatory drugs) from the fenamate group, COX2 selective inhibitors (celecoxib, rofecoxib), etc.

antioxydant agents: for example probucol, etc.

agents used in the treatment of cardiac insufficiency: thiazidic and non-thiazidic diuretics (furosemide, indapamide, hydrochlorthiazide, antialdosterone), ACE inhibitors (captopril, enalapril, ramipril or quinapril), digitalis drugs (digoxin, digitoxin), beta blockers (atenolol, metoprolol, labetalol, propranolol), phosphodiesterase inhibitors (enoximone, milrinone), etc.

agents used in the treatment of coronary insufficiency: beta blockers (atenolol, metoprolol, labetalol, propranolol), calcium channel blockers (nifedipine, felodipine or amlodipine, bepridil, diltiazem or verapamil), NO (nitric oxide) donors (trinitrine, isosorbide dinitrate, molsidomine), amiodarone, etc.

anti-cancer drugs: cytotoxic agents (agents interacting with DNA (DesoxyriboNucleic Acid), alkylating agents, cisplatin, and derivatives), cytostatic agents (GnRH (Gonatropin-Releasing Hormone) analogues, somatostatin analogues, progestin, antioestrogen drugs, aromatase inhibitors, etc.), immune response modulators (interferons, IL2, etc.), etc.

antiasthmatic drugs such as bronchodilators (beta 2 receptor agonists), corticoids, cromoglycate, leucotriene receptor antagonists (montelukast), etc.

corticoids used in the treatment of skin pathologies such as psoriasis and dermatitis vasodilators and/or anti-ischemic agents (buflomedil, Ginkgo Biloba extract, naftidrofuryl, pentoxifylline, piribedil), etc.

The invention also concerns a method for treating pathologies related to lipid and/or glucid metabolism comprising the administration to a subject, in particular a human, of an effective quantity of a compound or a pharmaceutical composition as above-defined. Within the context of the invention, the term "an effective quantity" refers to an amount of the compound sufficient to produce the desired biological result. Within the context of the invention, the term "subject" means a mammal and more particularly a human.

The term "treatment" designates curative, symptomatic, or preventative treatment. The compounds of this invention can thus be used upon subjects (such as mammals, in particular humans) having a declared disease. The compounds of this invention can also be used to delay or slow down the progress or prevent the further progress of the disease, thus improving the condition of patients. The compounds of the invention can finally be administered to healthy patients that might normally develop the disease or have a significant risk of developing the disease.

Pharmaceutical compositions according to the invention advantageously comprise one or several excipients or vehicles, acceptable within a pharmaceutical context (e.g. saline solutions, physiological solutions, isotonic solutions, etc., compatible with pharmaceutical usage and well-known by one of ordinary skill in the art). The compositions can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc. The compositions can be formulated in the form of injectable suspensions, gels, oils, pills, suppositories, powders, gelcaps, capsules, aerosols, etc., eventually by means of galenic forms or devices assuring a prolonged and/or slow release. For this kind of formulation, agents such as cellulose, carbonates or starches can advantageously be used.

The compounds or compositions according to the invention can be administered in different ways and in different forms. Thus, for example, they can be administered in a systematic way, per os, parenterally, by inhalation, or by injection, such as for example intravenously, by intra-muscular route, by subcutaneous route, by transdermal route, by intra-arterial route, etc. For the injections, the compounds are generally conditioned in the form of liquid suspensions which can be injected usingue syringes or perfusions, for example. It is understood that the speed and/or dose relative to the injection can be adapted by one of ordinary skill in the art, in function of the patient, the pathology, the form of administration, etc. Typically, the compounds administered at doses varying between 1 μg and 2 g per administration, preferentially from 0.1 mg to 1 g per administration. Administration can be daily or even several times per day, if necessary. Additionally, the compositions according to the invention can include other agents or active constituents.

BRIEF DESCRIPTION OF DRAWINGS

Abbreviation Used in These Figures:
Cpd=compounds;
Ctrl=control;
mpk=mg/kg/day;
LDL-cholesterol=Low Density Lipoprotein cholesterol;
HDL-cholesterol=High Density Lipoprotein cholesterol;
VLDL-cholesterol=Very Low Density Lipoprotein cholesterol.

The compounds are tested in doses of between $10^{-7}$ and 100 μM on Gal4-PPARα, γ, and δ chimeras. The induction factor, i.e. the ratio between the luminescence induced by the compound and the luminescence induced by the control, is measured for each condition. The higher the induction factor is, the more the compound has PPAR activating properties.

Figure 1:
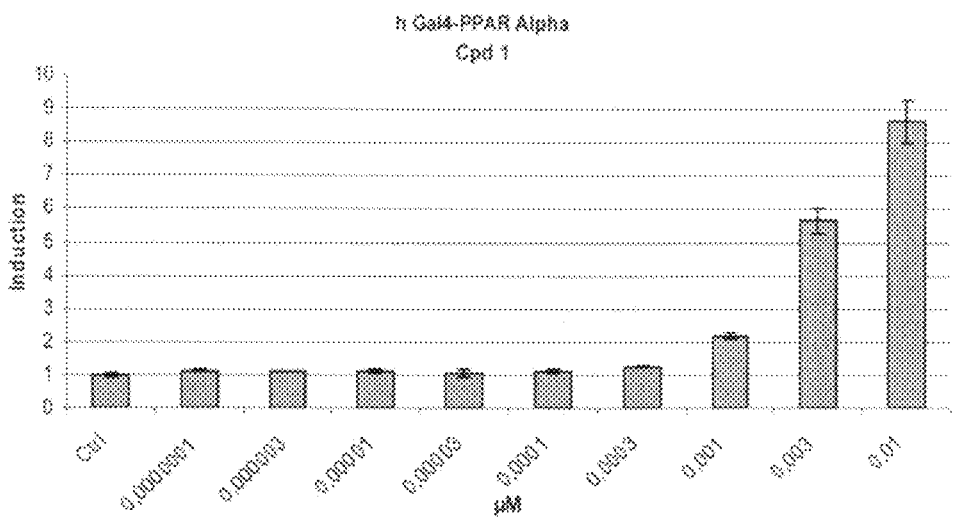
FIGS. 1-1 to 1-66: In vitro Evaluation of the PPAR Activated Properties of the Compounds of the Invention According to the Dose The activation of PPARs is evaluated in vitro using a monkey kidney fibroblast line (COS-7) by measuring the transcriptional activity of chimeras made up of the DNA binding domain of the Gal4 transcription factor of yeast and of the binding domain to the ligand of the different PPARs.
Figures 1, 2:
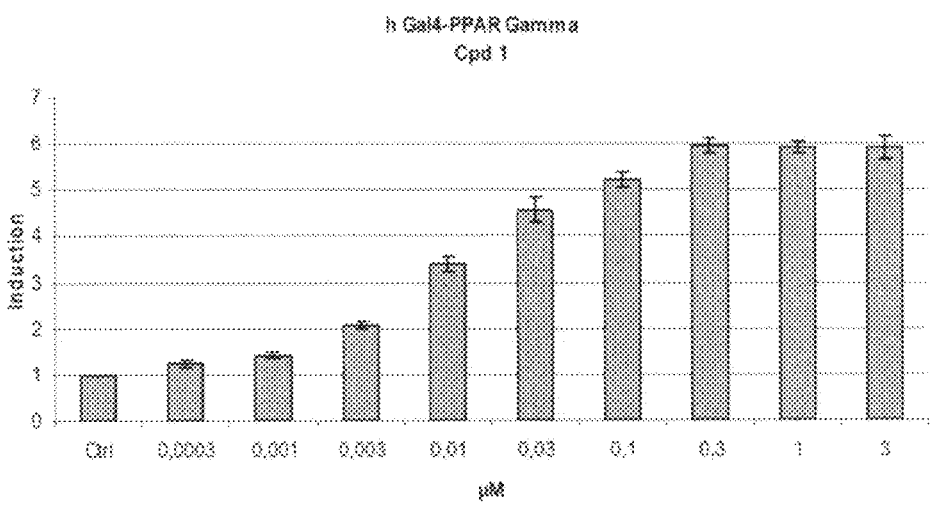
Figures 1, 2, 3:
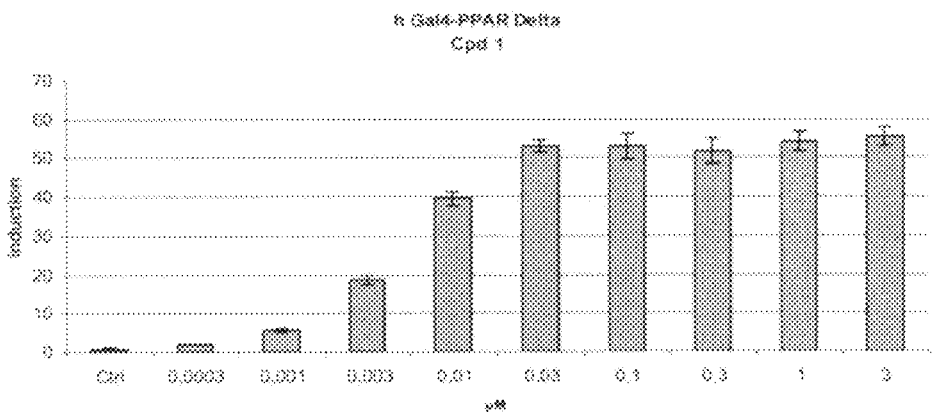

FIGS. 1-1, 1-2, 1-3: In vitro evaluation of the PPARα, γ, δ activating properties of compound 1;
FIGS. 1-4, 1-5, 1-6: In vitro evaluation of the PPARα, γ, δ activating properties of compound 2;
FIGS. 1-7, 1-8, 1-9: In vitro evaluation of the PPARα, γ, δ activating properties of compound 3;
FIGS. 1-10, 1-11, 1-12: In vitro evaluation of the PPARα, γ, δ activating properties of compound 4;
FIGS. 1-13, 1-14, 1-15: In vitro evaluation of the PPARα, γ, δ activating properties of compound 5;
FIGS. 1-16, 1-17, 1-18: In vitro evaluation of the PPARα, γ, δ activating properties of compound 6;
FIGS. 1-19, 1-20, 1-21: In vitro evaluation of the PPARα, γ, δ activating properties of compound 7;
FIGS. 1-22, 1-23, 1-24: In vitro evaluation of the PPARα, γ, δ activating properties of compound 8;
FIGS. 1-25, 1-26, 1-27: In vitro evaluation of the PPARα, γ, δ activating properties of compound 9;
FIGS. 1-28, 1-29, 1-30: In vitro evaluation of the PPARα, γ, δ activating properties of compound 10;
FIGS. 1-31, 1-32, 1-33: In vitro evaluation of the PPARα, γ, δ activating properties of compound 11;
FIGS. 1-34, 1-35, 1-36: In vitro evaluation of the PPARα, γ, δ activating properties of compound 12;
FIGS. 1-37, 1-38, 1-39: In vitro evaluation of the PPARα, γ, δ activating properties of compound 14;
FIGS. 1-40, 1-41, 1-42: In vitro evaluation of the PPARα, γ, δ activating properties of compound 17;
FIGS. 1-43, 1-44, 1-45: In vitro evaluation of the PPARα, γ, δ activating properties of compound 18;
FIGS. 1-46, 1-47, 1-48: In vitro evaluation of the PPARα, γ, δ activating properties of compound 19;
FIGS. 1-49, 1-50, 1-51: In vitro evaluation of the PPARα, γ, δ activating properties of compound 20;
FIGS. 1-52, 1-53, 1-54: In vitro evaluation of the PPARα, γ, δ activating properties of compound 21;
FIGS. 1-55, 1-56, 1-57: In vitro evaluation of the PPARα, γ, δ activating properties of compound 22;
FIGS. 1-58, 1-59, 1-60: In vitro evaluation of the PPARα, γ, δ activating properties of compound 23;
FIGS. 1-61, 1-62, 1-63: In vitro evaluation of the PPARα, γ, δ activating properties of compound 24;
FIGS. 1-64, 1-65, 1-66: In vitro evaluation of the PPARα, γ, δ activating properties of compound 25;
FIGS. 2-1 to 2-9: In vivo Evaluation, on ApoE2/E2 Mice, of Hypolipidemic Properties and Stimulative Properties of the Synthesis of HDL-cholesterol of the Compounds According to the Invention The effect of the compounds according to the invention is evaluated in vivo on mice humanized by the E2 isoform apolipoprotein E (E2/E2).

The dyslipidemic E2/E2 mouse's rates of total cholesterol, of triglycerides, and plasma free fatty acids are measured after 8 or 14 days of a per os treatment with the compounds according to the invention. These parameters are compared to those obtained from the control animals (animals not treated with the compounds according to the invention): the measured difference shows the hypolipidemic effect of the compounds according to the invention.

FIG. 2-1: Plasma cholesterol levels after 8 days of treatment with compound 1, administered at 50 mpk;
FIG. 2-2: Plasma triglyceride levels after 8 days of treatment with compound 1, administered at 50 mpk;
FIG. 2-3: Plasma cholesterol levels after 14 days of treatment with compound 8, administered at 3 to 10 mpk.

The effectiveness of the compounds according to the invention is also evaluated by measuring, in the hepatic tissue, the expression of genes involved in lipid and/or glucids metabolism and in energy dissipation. Each level of genes expression is normalised regarding the expression level of the reference gene 36B4's. The induction factor, i.e. the ratio between the relative signal (induced by the compound according to the invention) and the average of the relative values relating to the control group is then calculated. The higher the induction factor is, the more the compound promotes hepatic gene expression. The final result is expressed as an average of the induction values obtained with each experimental group.

Figures 1, 2, 3, 4:
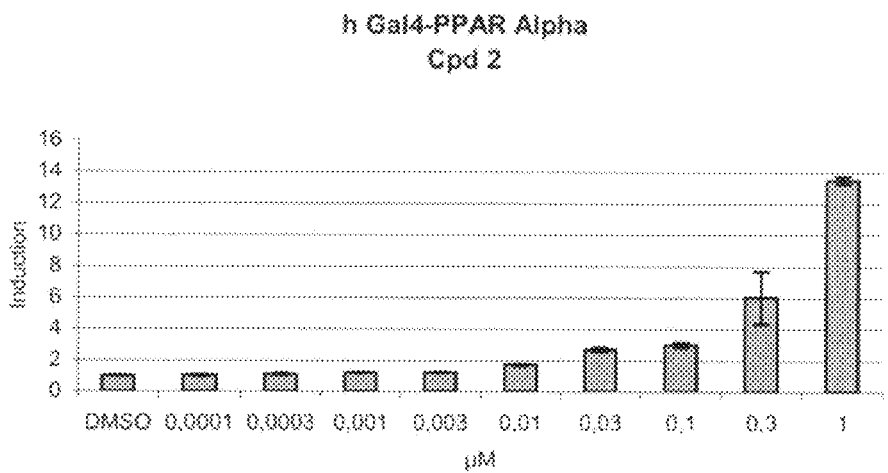
Figures 1, 2, 3, 4, 5:
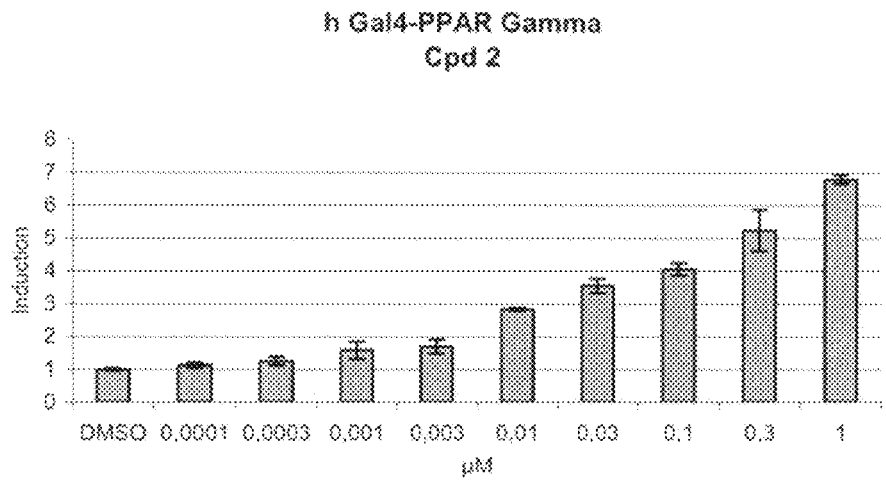
Figures 1, 2, 3, 4, 5, 6:
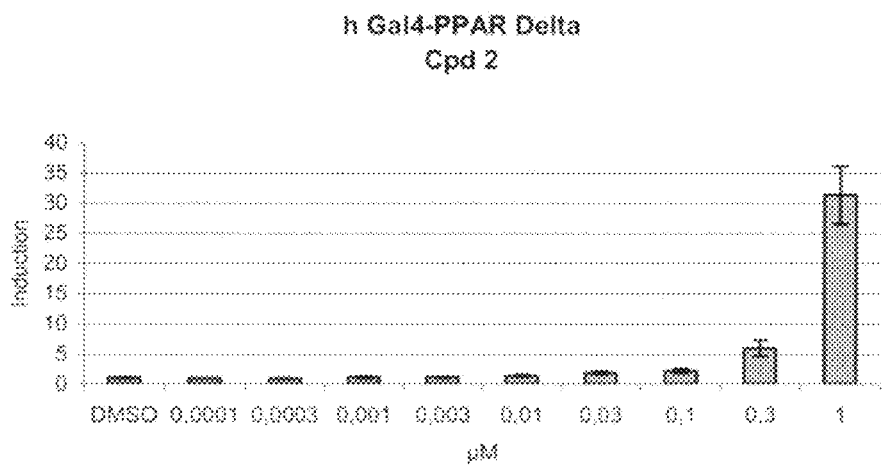
Figures 1, 2, 3, 4, 5, 6, 7:
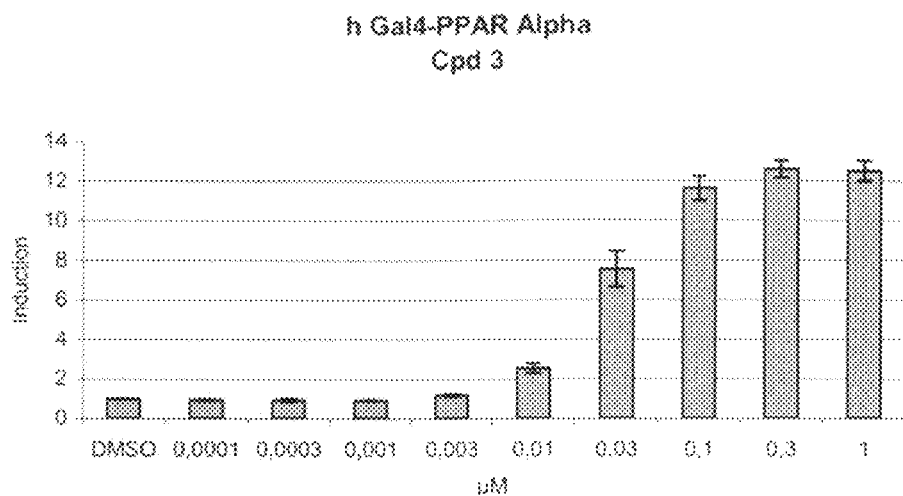
Figures 1, 2, 3, 4, 5, 6, 7, 8:
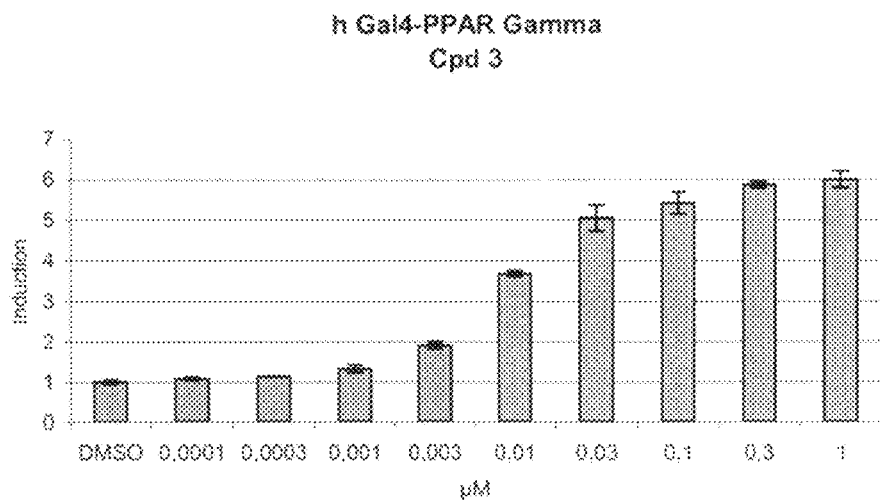
Figures 1, 2, 3, 4, 5, 6, 7, 8, 9:
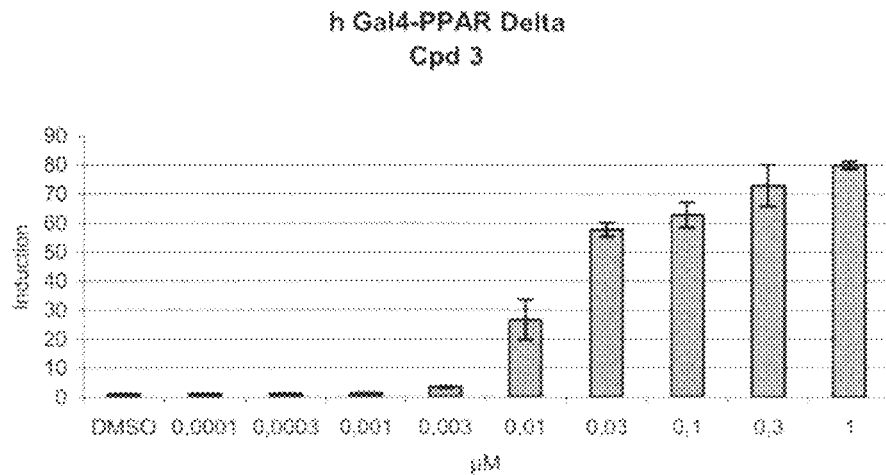
Figures 1, 2, 3, 4, 5, 6, 7, 8, 9, 10:
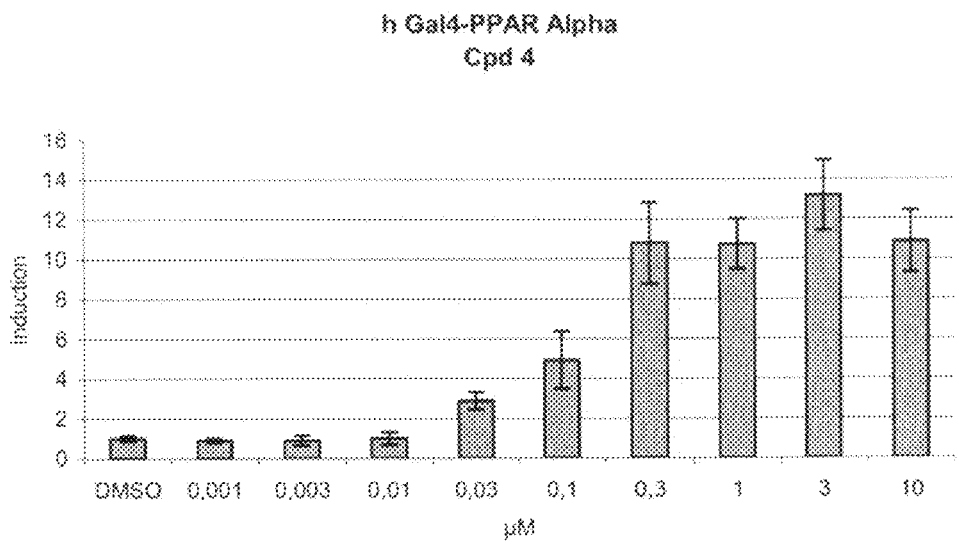
Figures 1, 2, 3, 4, 5, 6, 7, 8, 9, 10, 11:
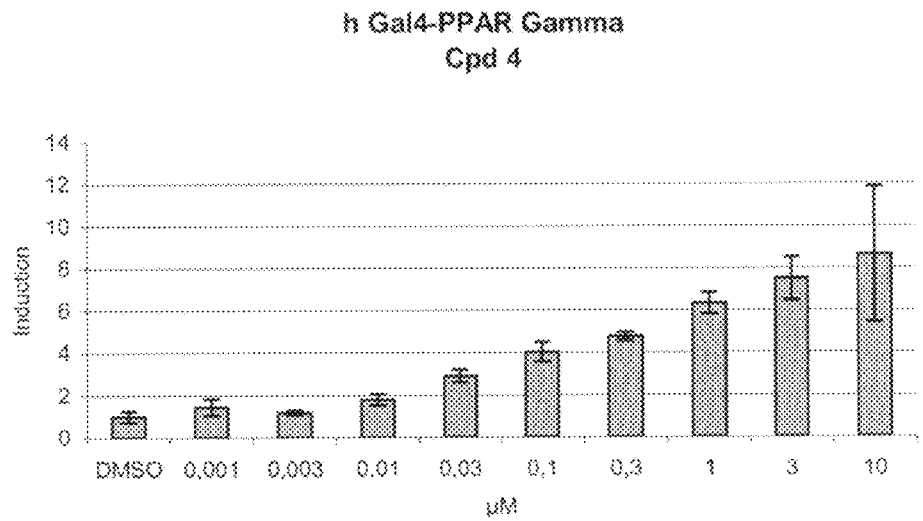
Figures 1, 2, 3, 4, 5, 6, 7, 8, 9, 10, 11, 12:
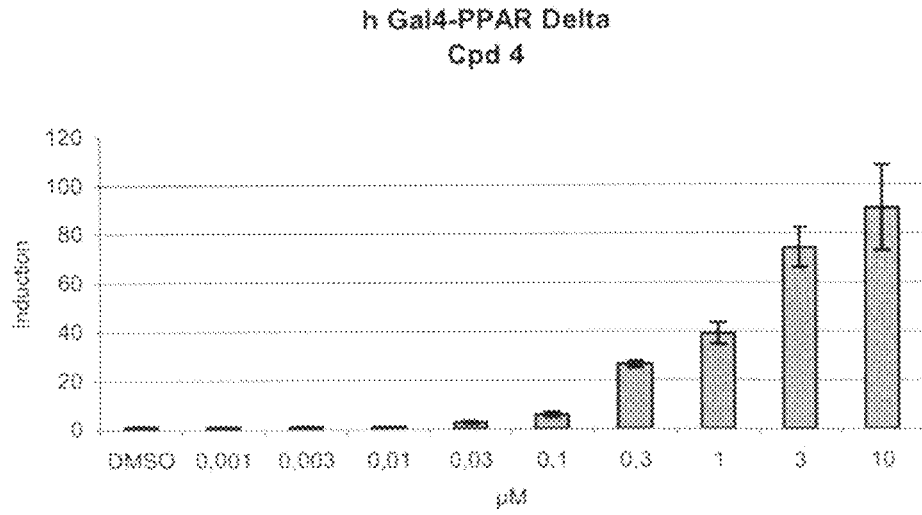
Figures 1, 2, 3, 4, 5, 6, 7, 8, 9, 10, 11, 12, 13:
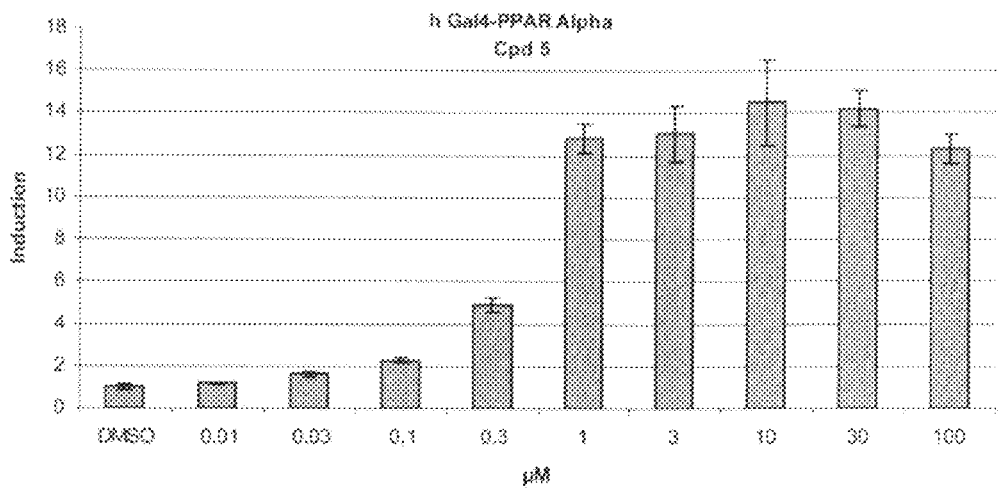
Figures 1, 2, 3, 4, 5, 6, 7, 8, 9, 10, 11, 12, 13, 14:
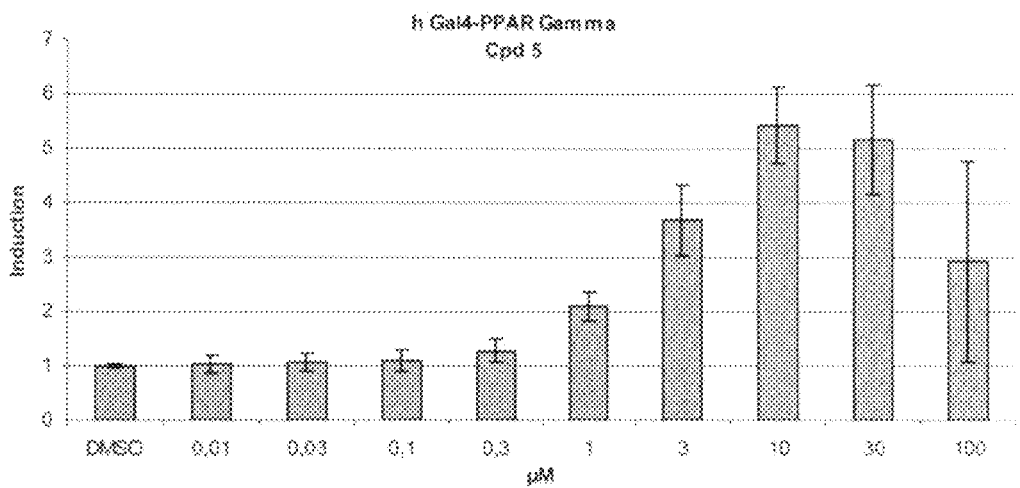
Figures 1, 2, 3, 4, 5, 6, 7, 8, 9, 10, 11, 12, 13, 14, 15:
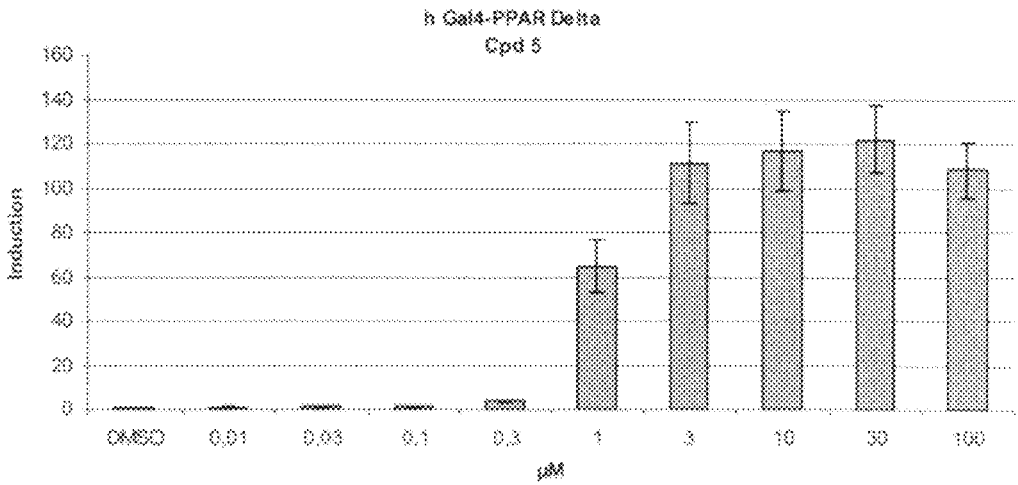
Figures 1, 2, 3, 4, 5, 6, 7, 8, 9, 10, 11, 12, 13, 14, 15, 16:
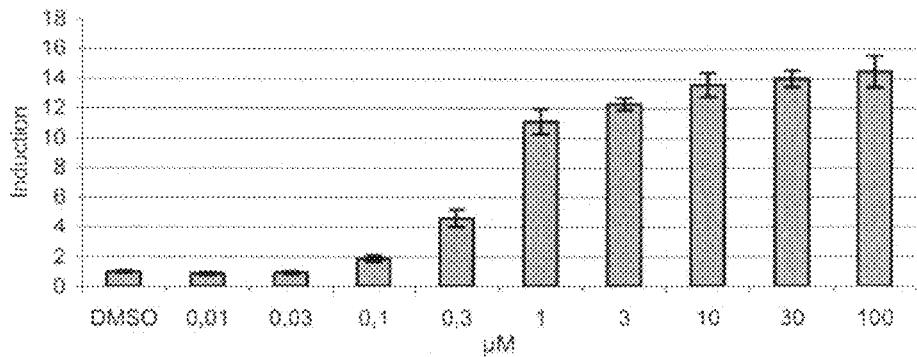
Figures 1, 2, 3, 4, 5, 6, 7, 8, 9, 10, 11, 12, 13, 14, 15, 16, 17:
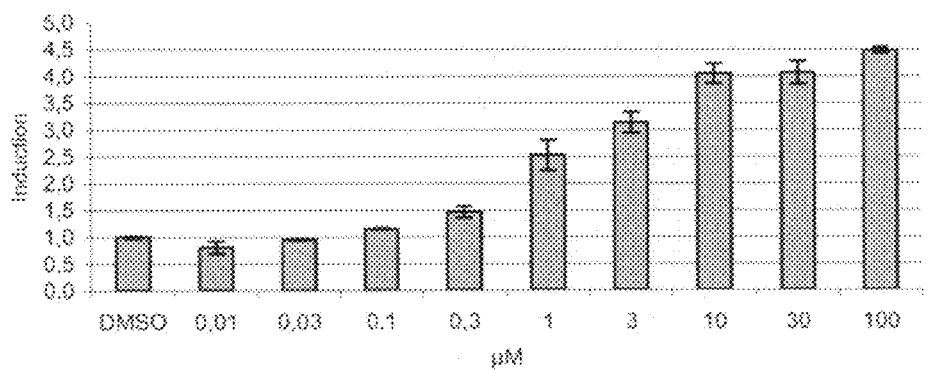
Figures 1, 2, 3, 4, 5, 6, 7, 8, 9, 10, 11, 12, 13, 14, 15, 16, 17, 18:
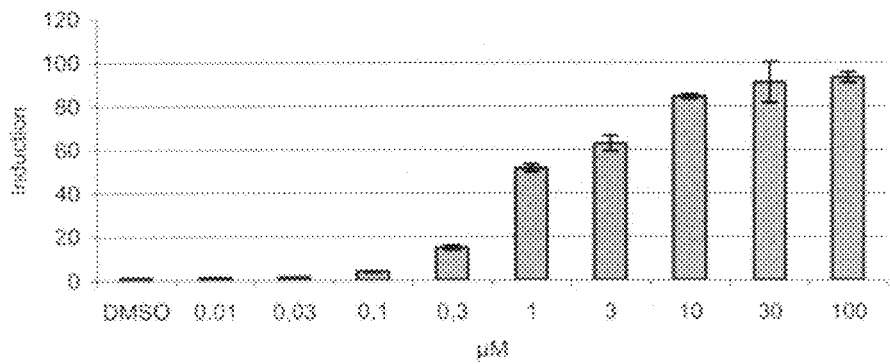
Figures 1, 2, 3, 4, 5, 6, 7, 8, 9, 10, 11, 12, 13, 14, 15, 16, 17, 18, 19:
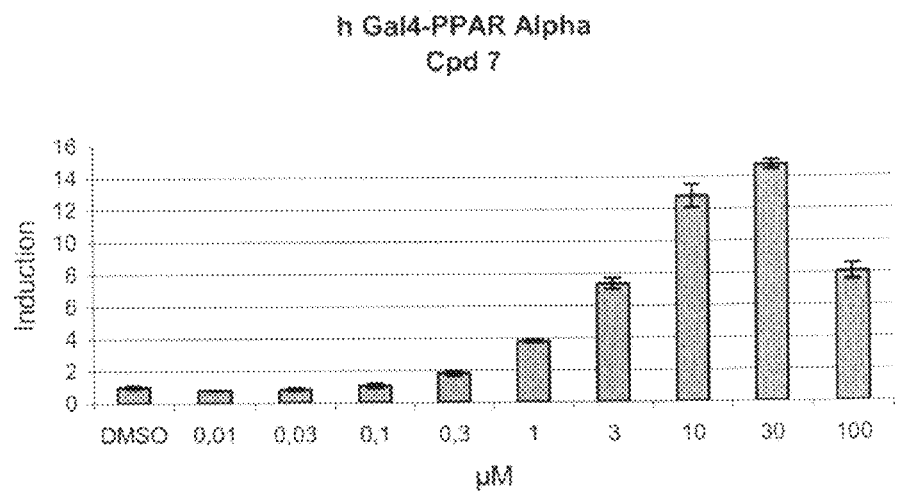
Figures 1, 2, 3, 4, 5, 6, 7, 8, 9, 10, 11, 12, 13, 14, 15, 16, 17, 18, 19, 20:
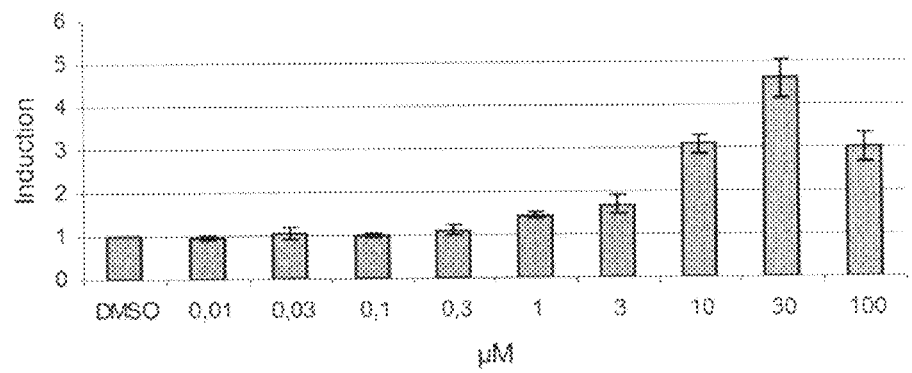
Figures 1, 2, 3, 4, 5, 6, 7, 8, 9, 10, 11, 12, 13, 14, 15, 16, 17, 18, 19, 20, 21:
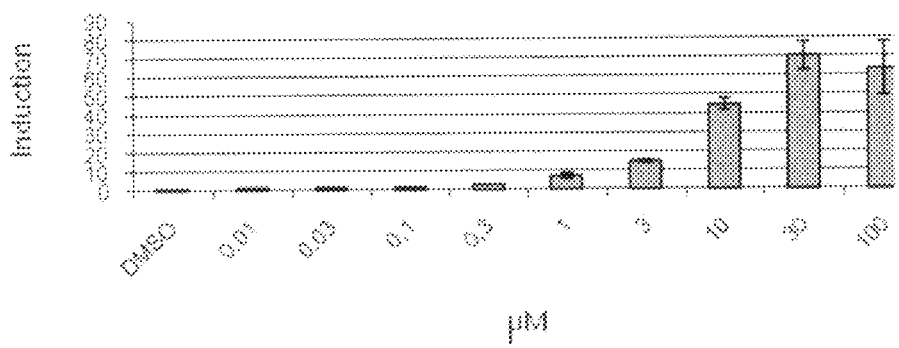
Figures 1, 2, 3, 4, 5, 6, 7, 8, 9, 10, 11, 12, 13, 14, 15, 16, 17, 18, 19, 20, 21, 22:
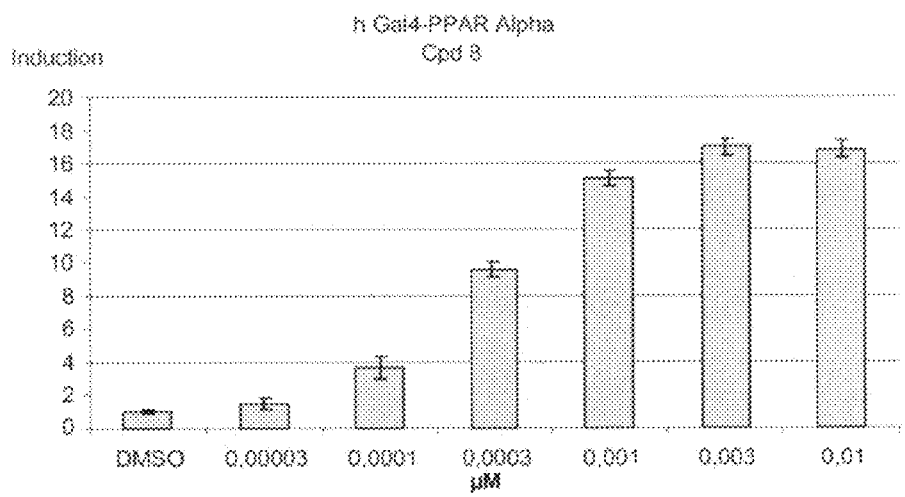
Figures 1, 2, 3, 4, 5, 6, 7, 8, 9, 10, 11, 12, 13, 14, 15, 16, 17, 18, 19, 20, 21, 22, 23:
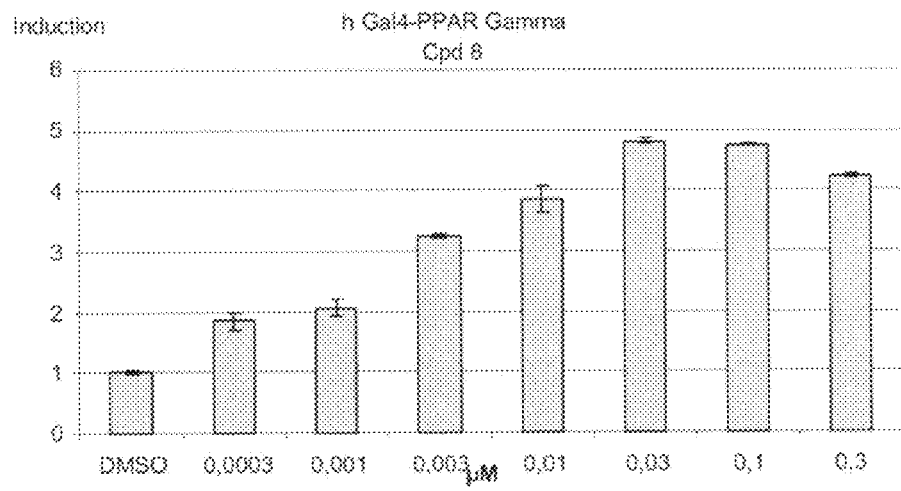
Figures 1, 2, 3, 4, 5, 6, 7, 8, 9, 10, 11, 12, 13, 14, 15, 16, 17, 18, 19, 20, 21, 22, 23, 24:
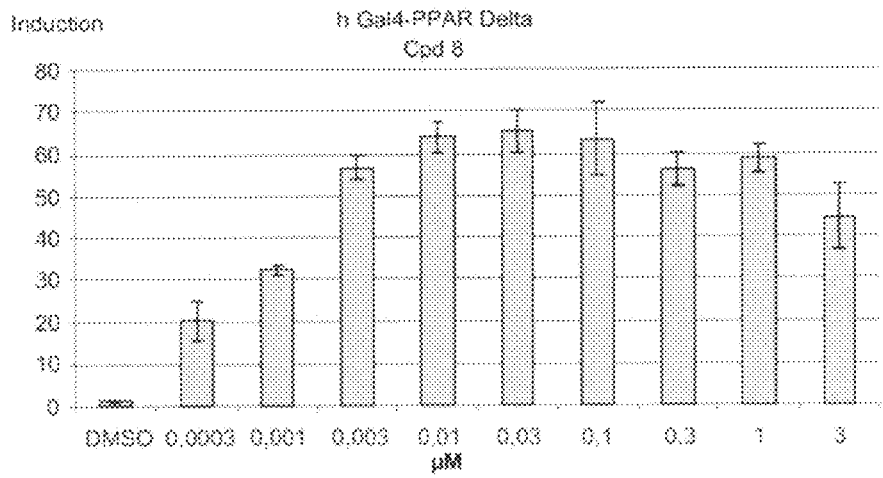
Figures 1, 2, 3, 4, 5, 6, 7, 8, 9, 10, 11, 12, 13, 14, 15, 16, 17, 18, 19, 20, 21, 22, 23, 24, 25:
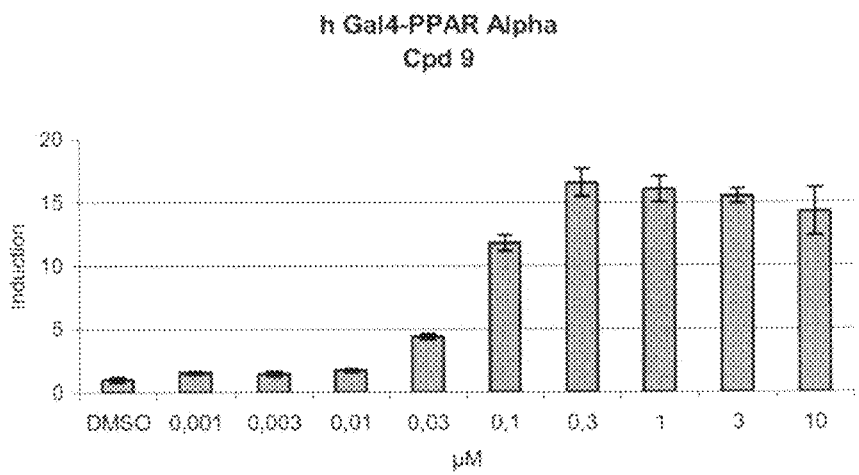
Figures 1, 2, 3, 4, 5, 6, 7, 8, 9, 10, 11, 12, 13, 14, 15, 16, 17, 18, 19, 20, 21, 22, 23, 24, 25, 26:
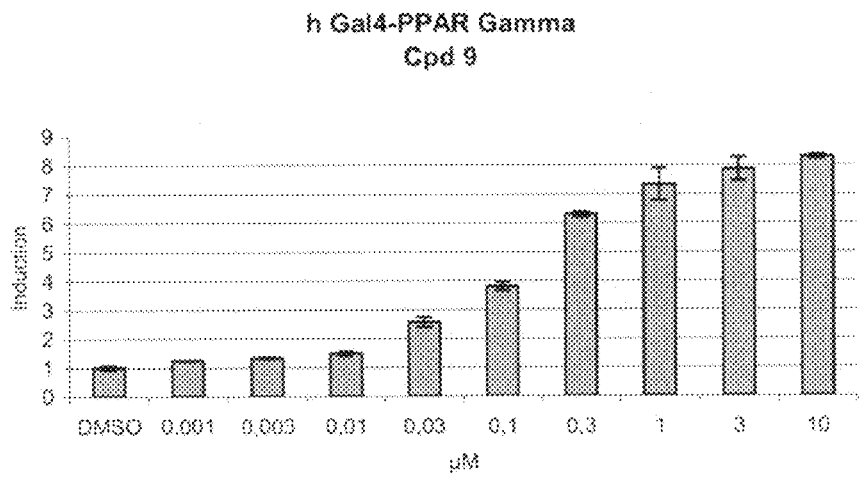
Figures 1, 2, 3, 4, 5, 6, 7, 8, 9, 10, 11, 12, 13, 14, 15, 16, 17, 18, 19, 20, 21, 22, 23, 24, 25, 26, 27:
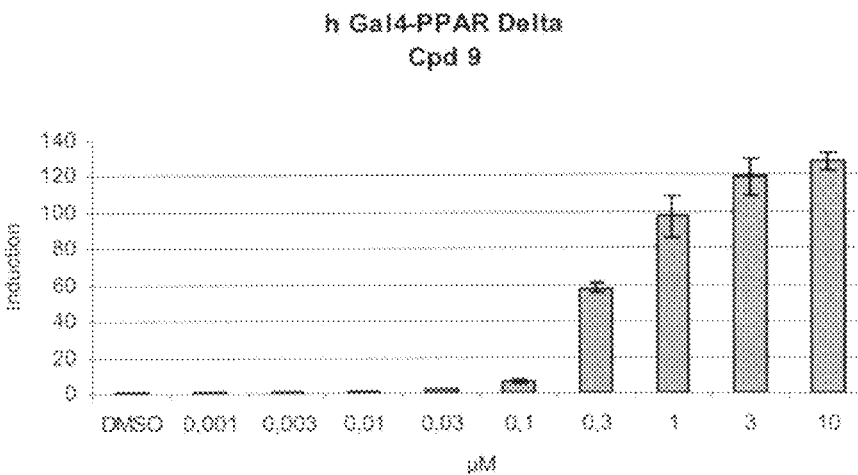
Figures 1, 2, 3, 4, 5, 6, 7, 8, 9, 10, 11, 12, 13, 14, 15, 16, 17, 18, 19, 20, 21, 22, 23, 24, 25, 26, 27, 28:
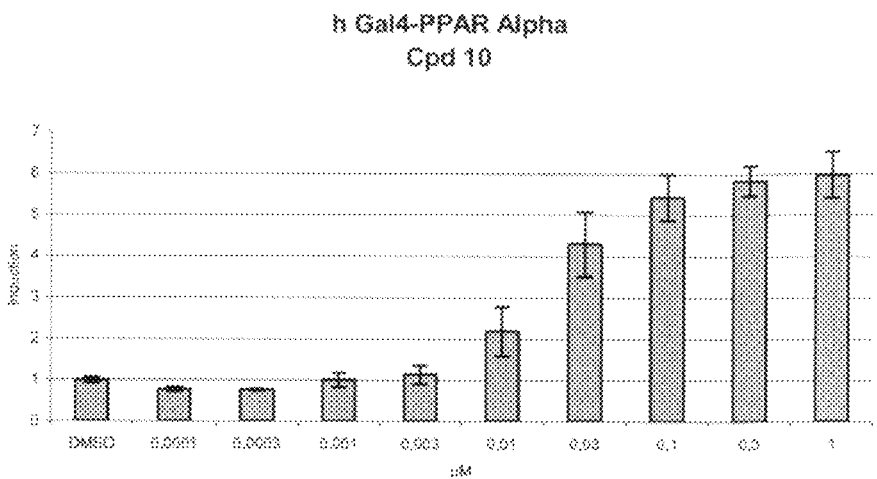
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29:
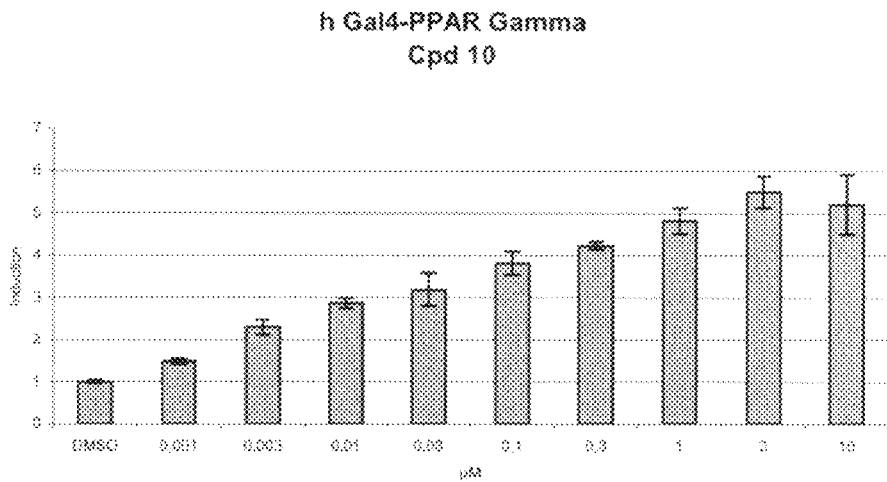
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30:
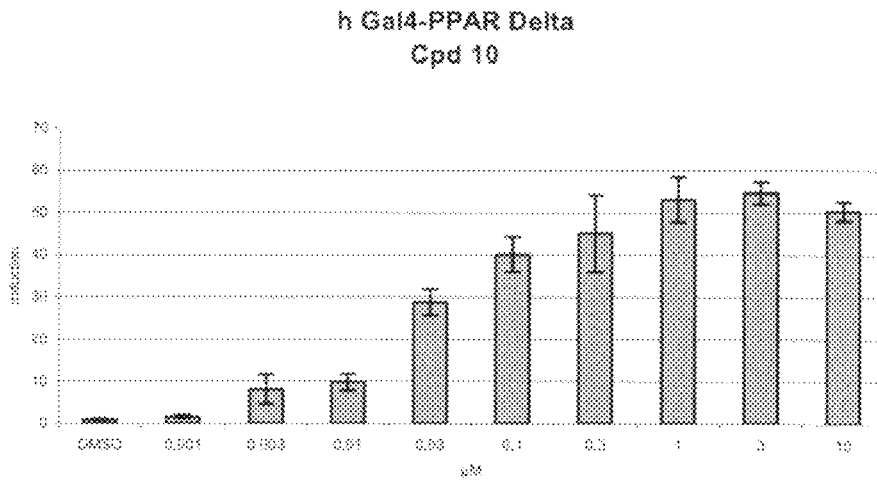
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31:
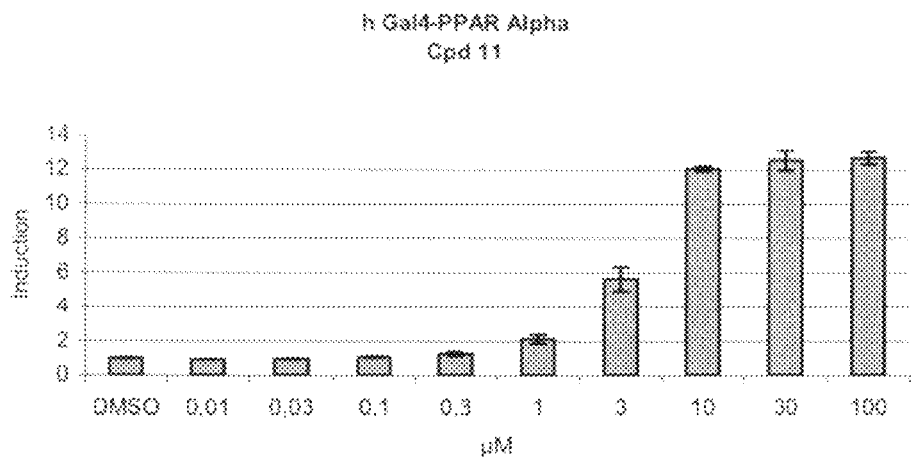
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
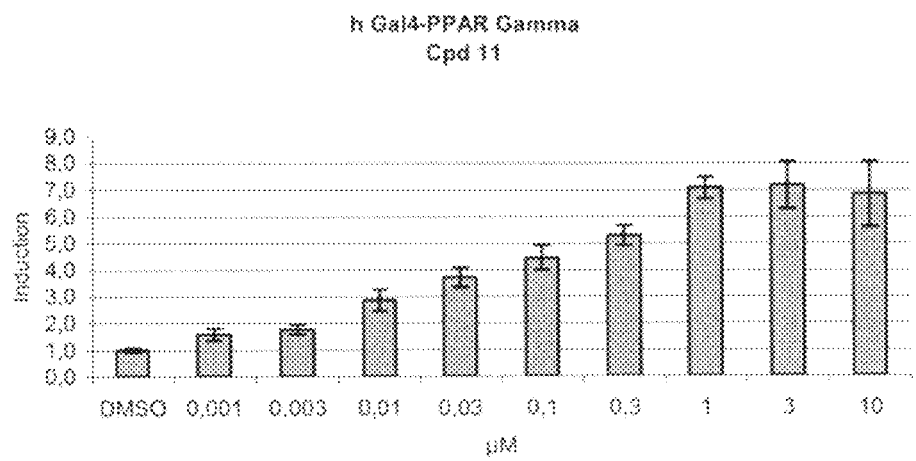
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
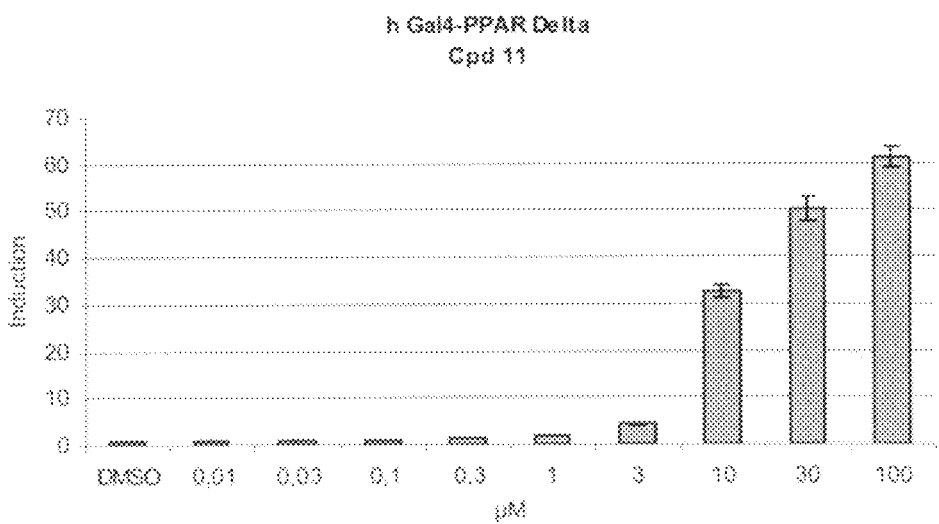
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
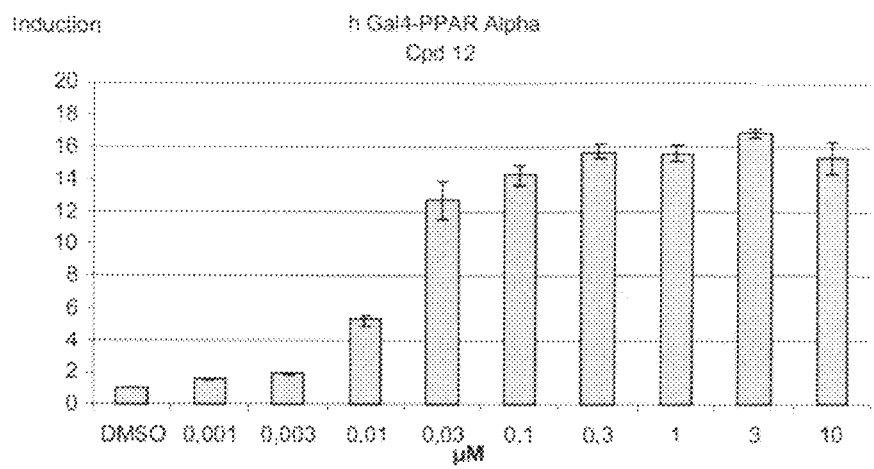
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
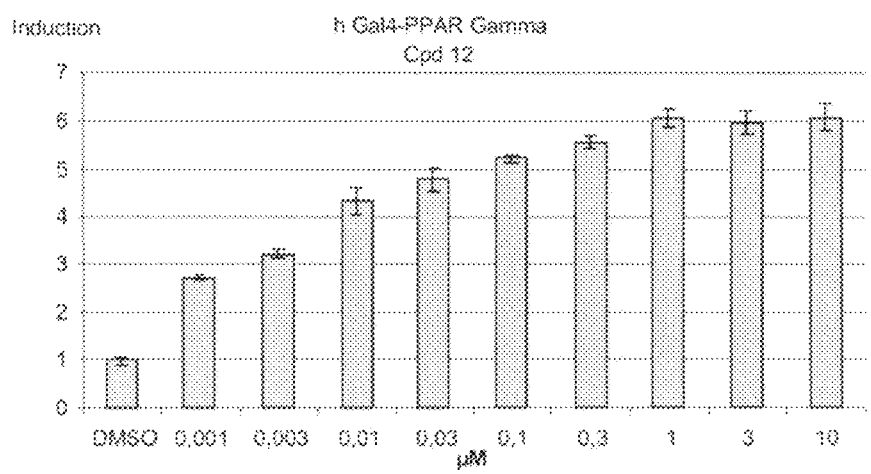
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
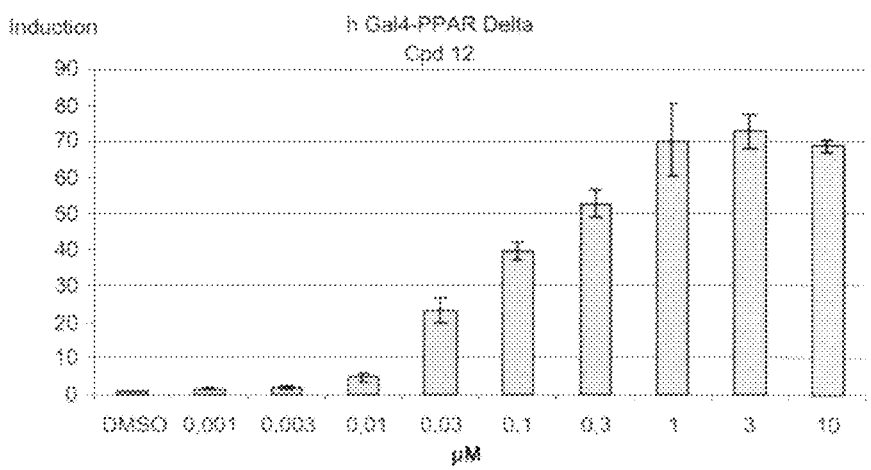
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
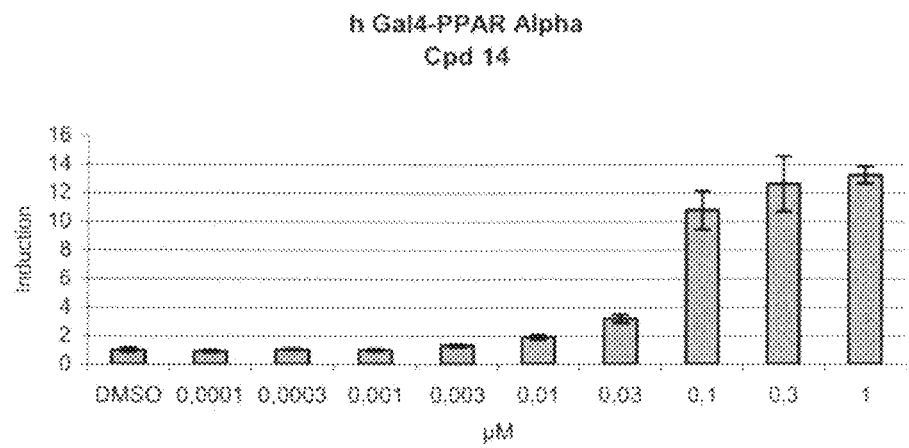
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
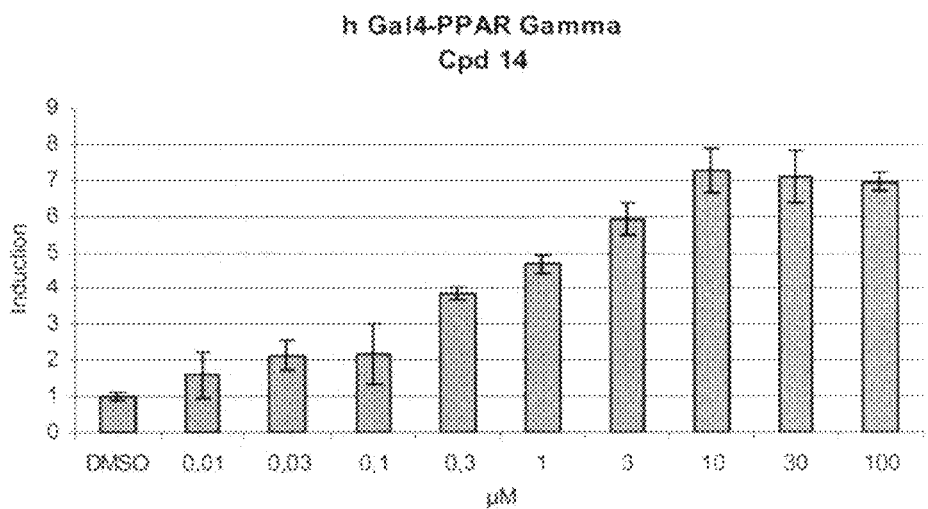
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
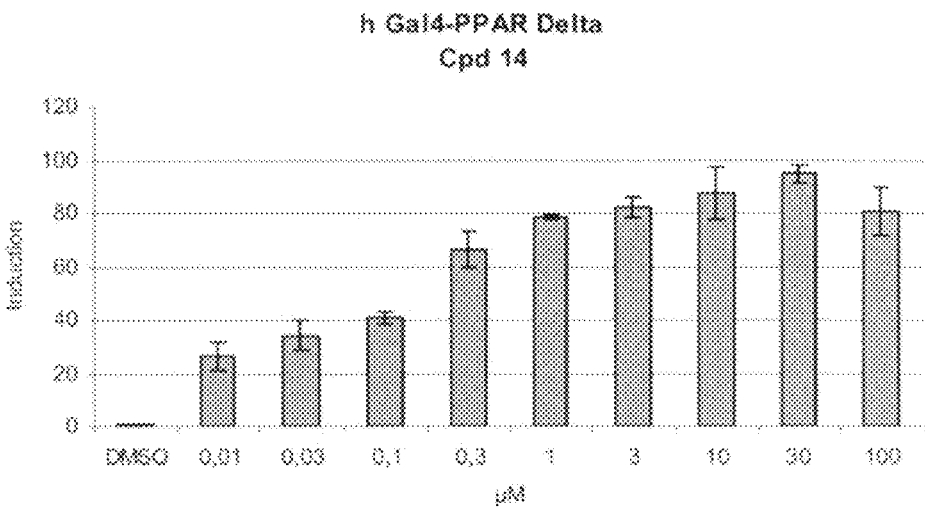
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
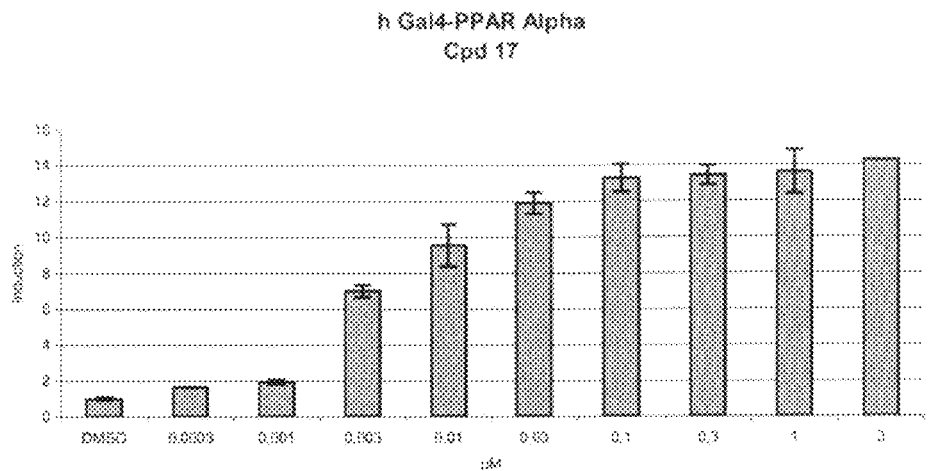
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
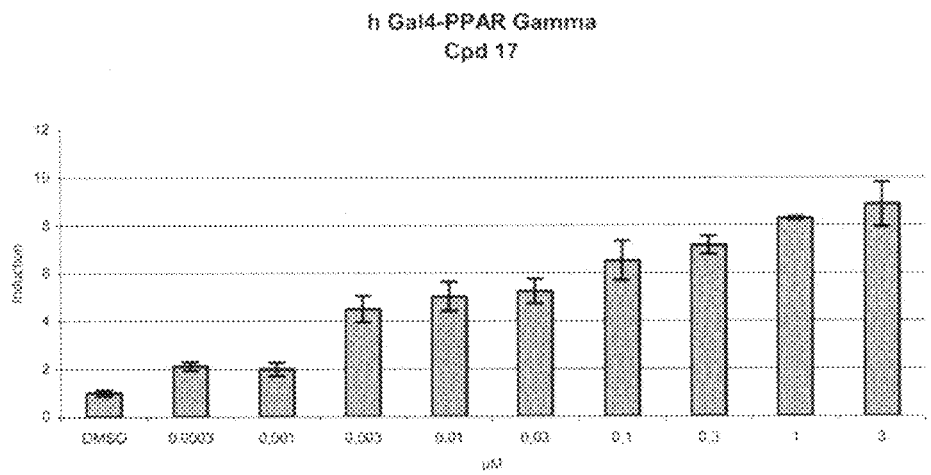
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
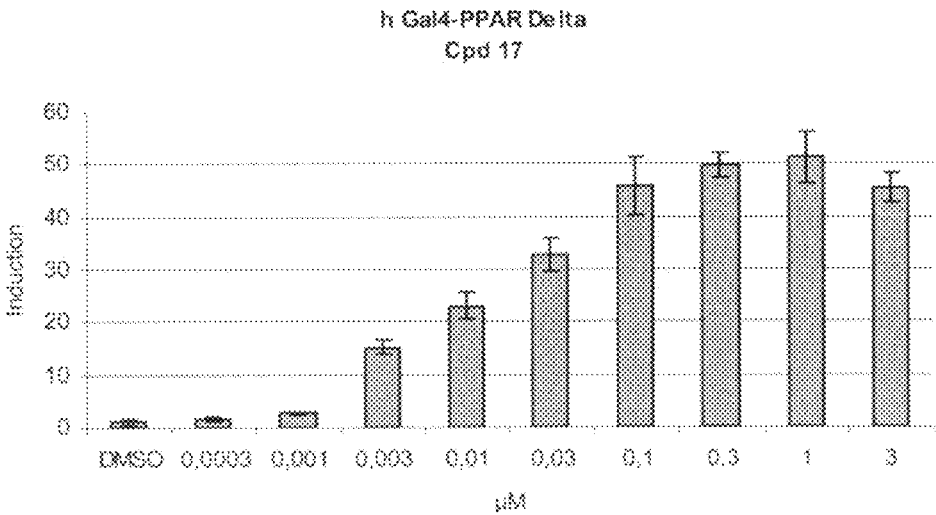
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
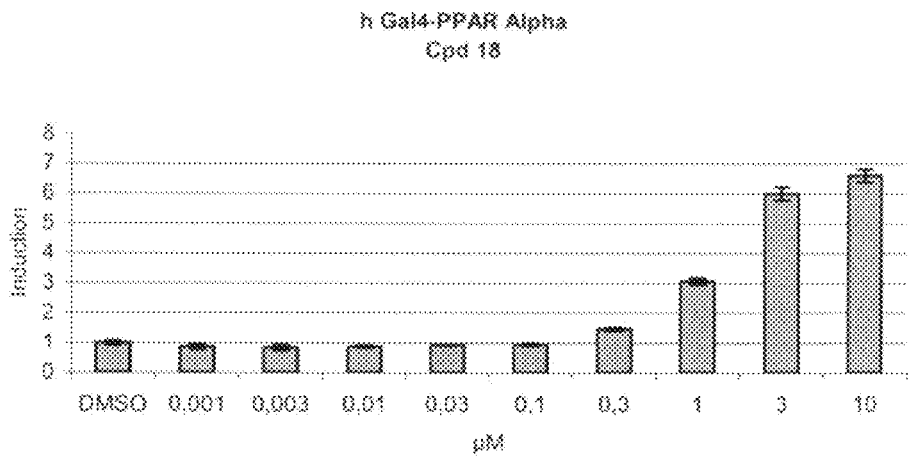
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
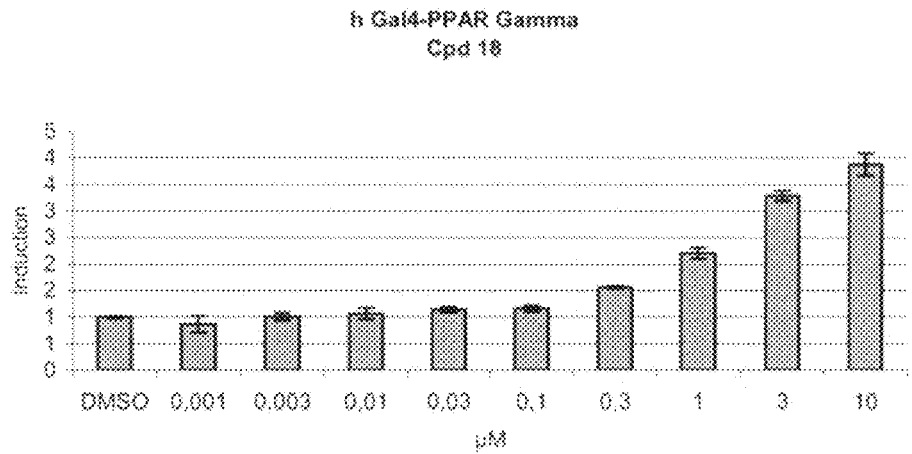
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
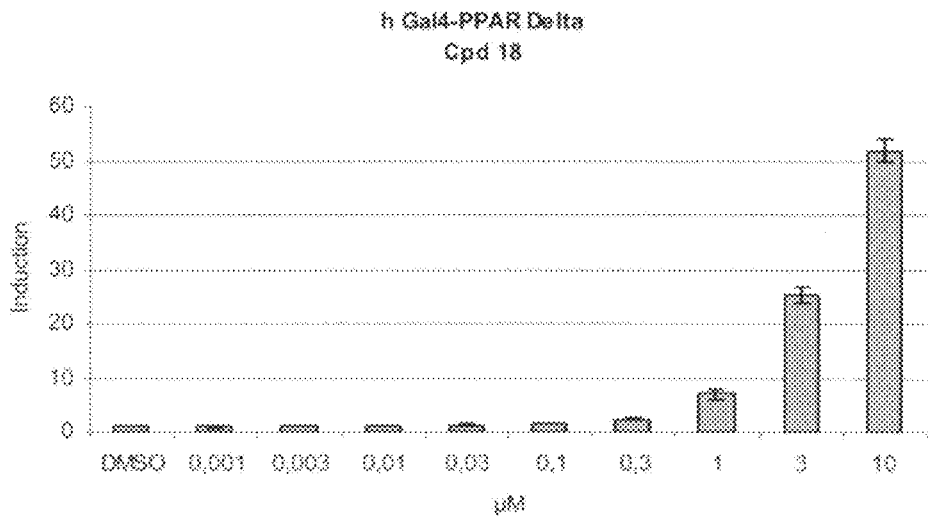
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
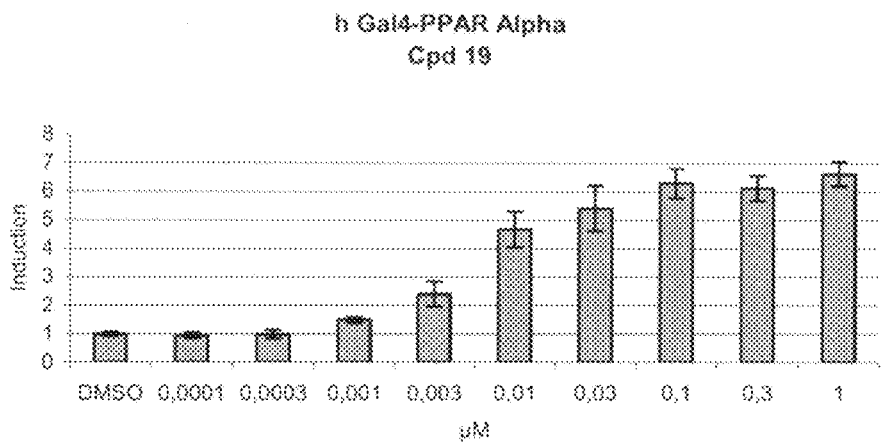
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
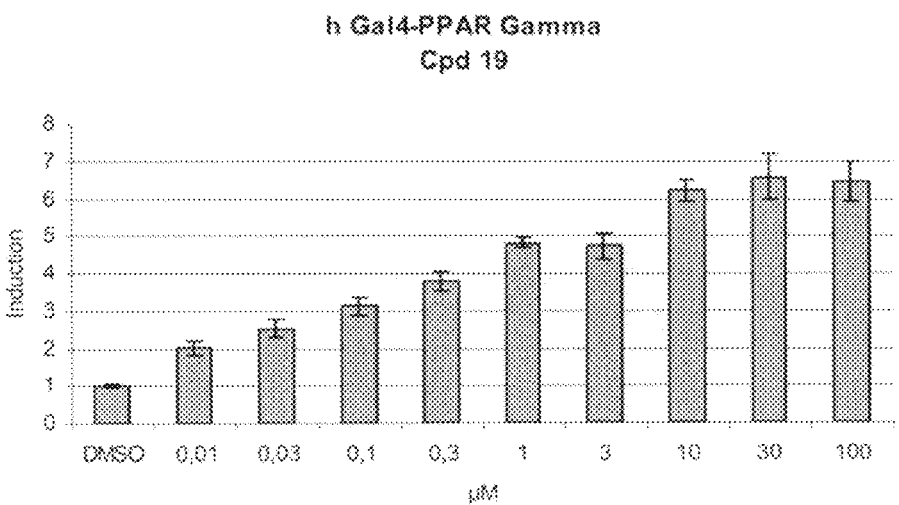
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
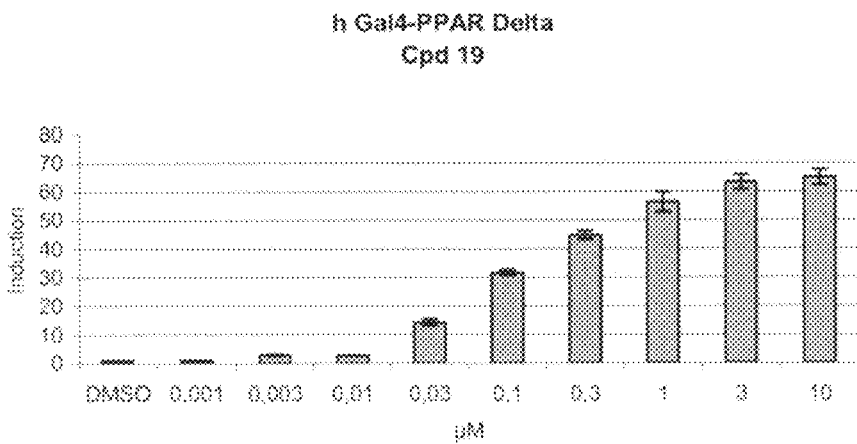
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
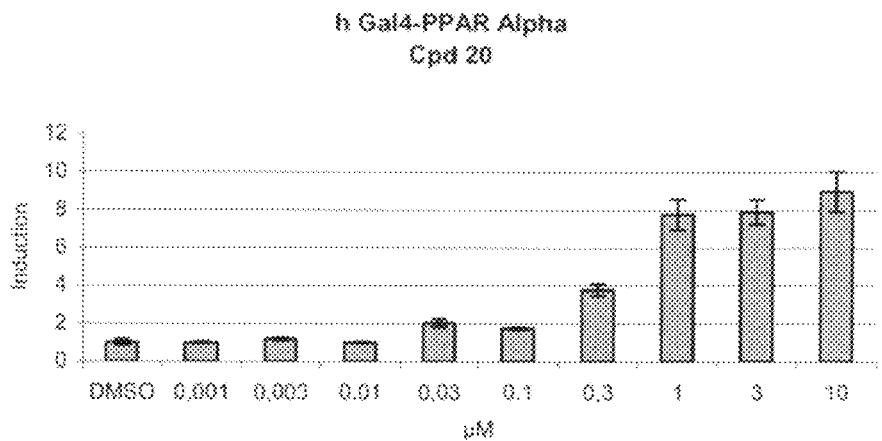
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
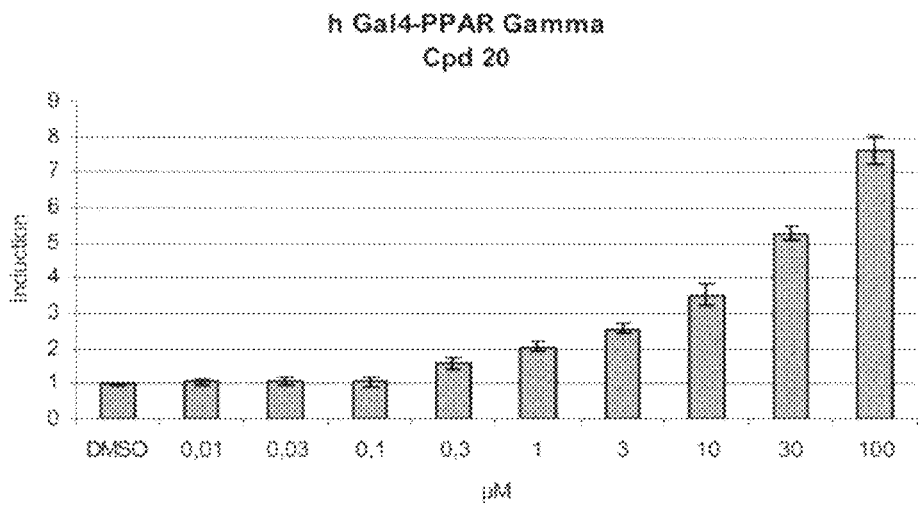
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
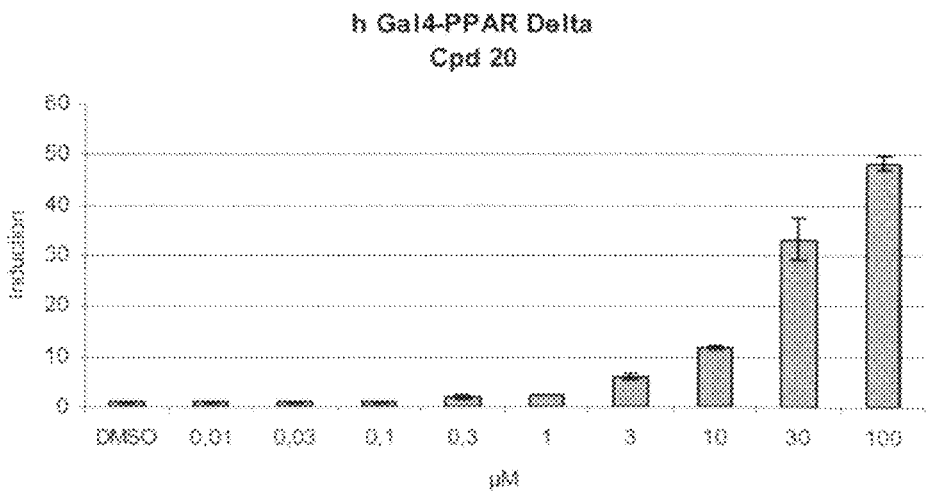
Figures 1, 52:
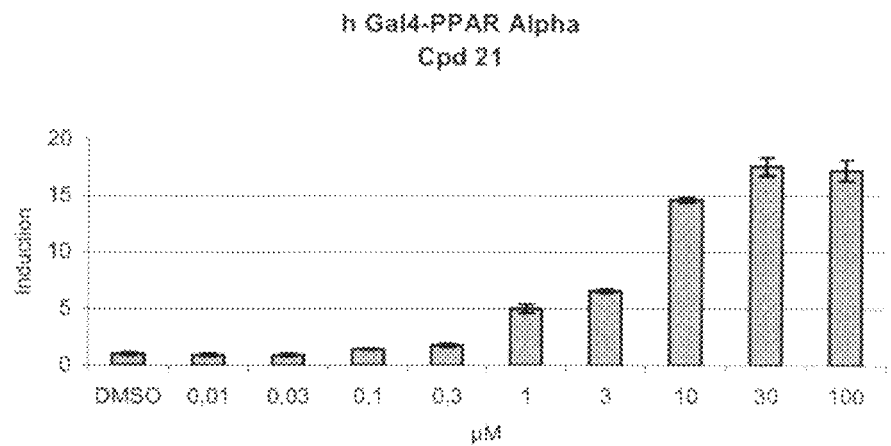
Figures 1, 53:
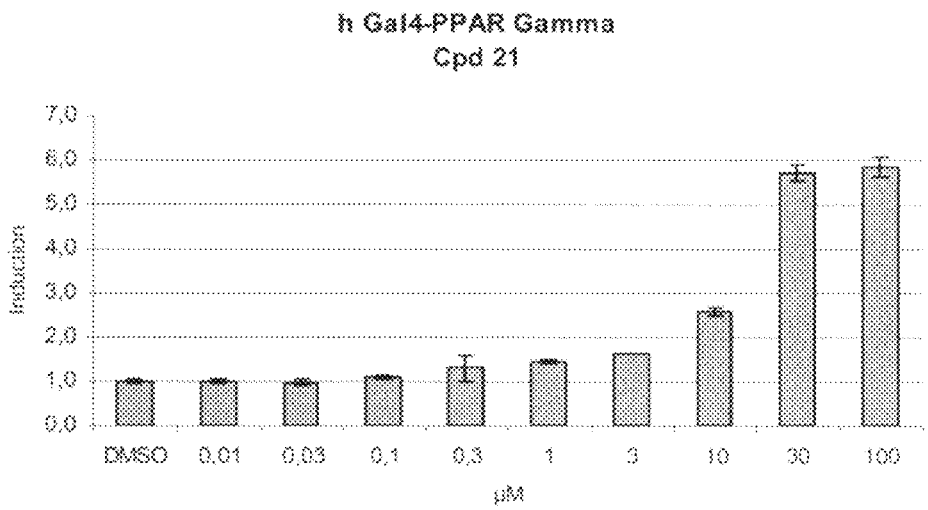
Figures 1, 54:
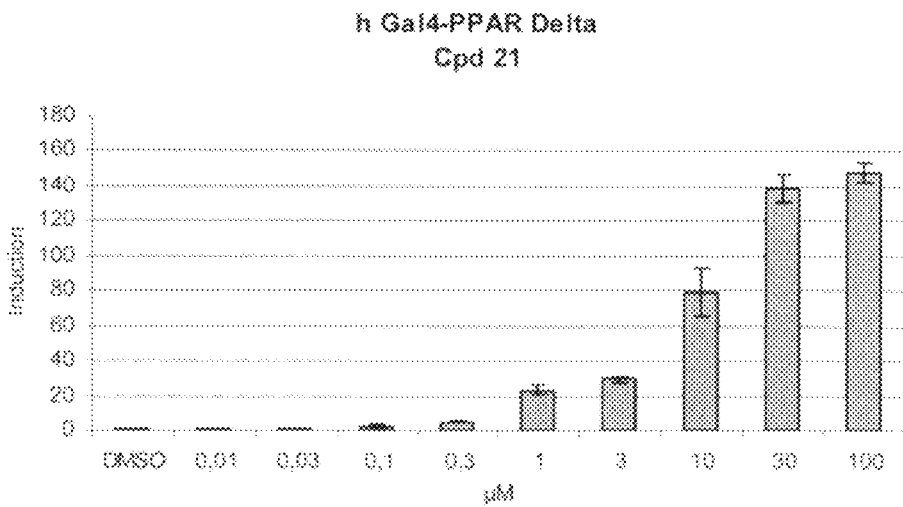
Figures 1, 55:
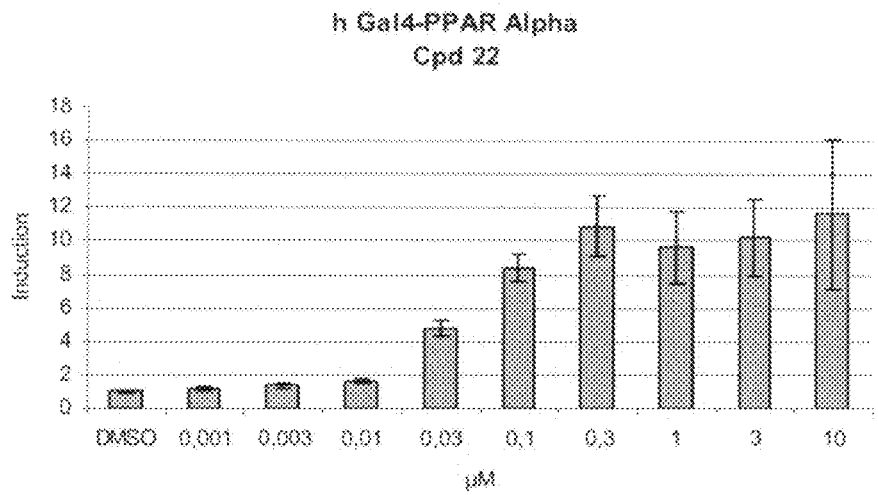
Figures 1, 56:
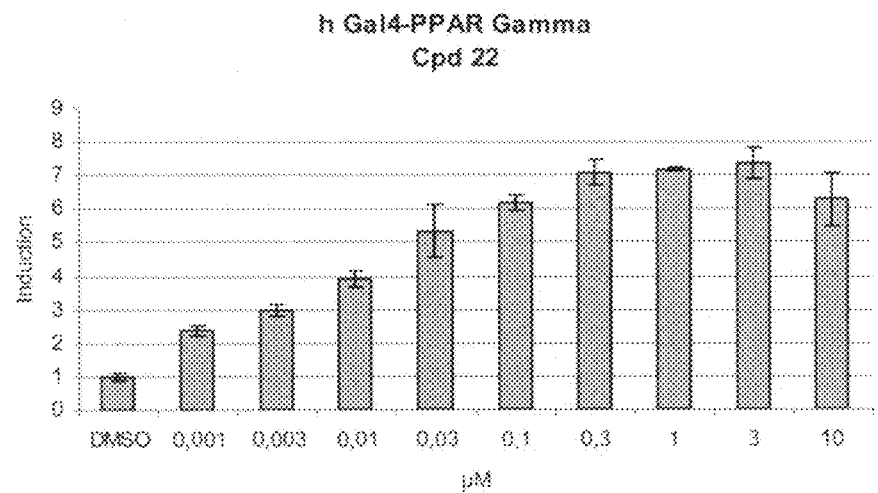
Figures 1, 57:
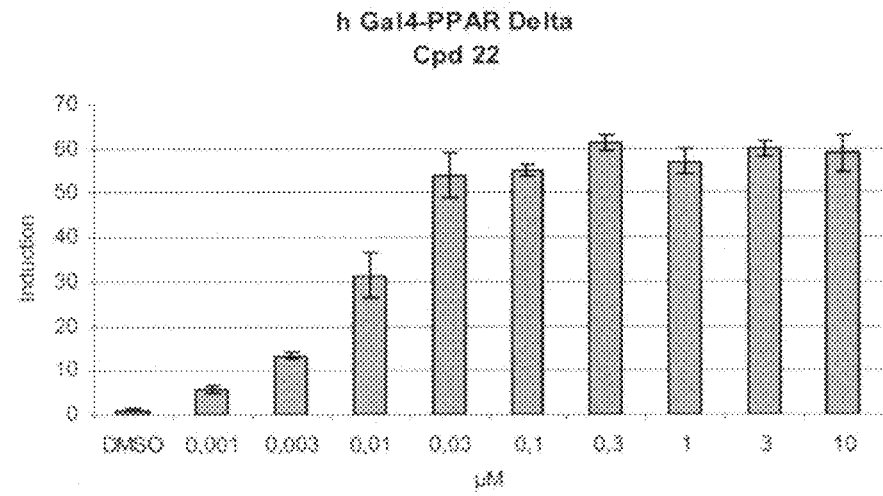
Figures 1, 58:
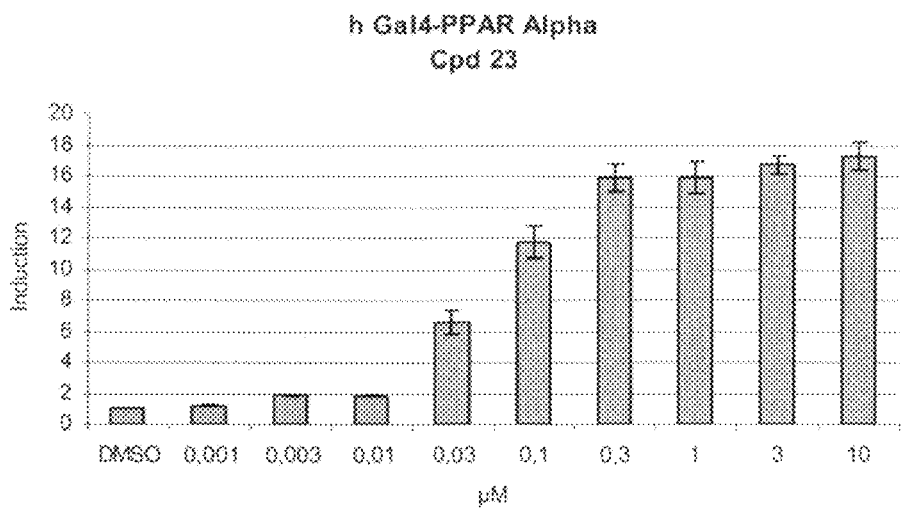
Figures 1, 59:
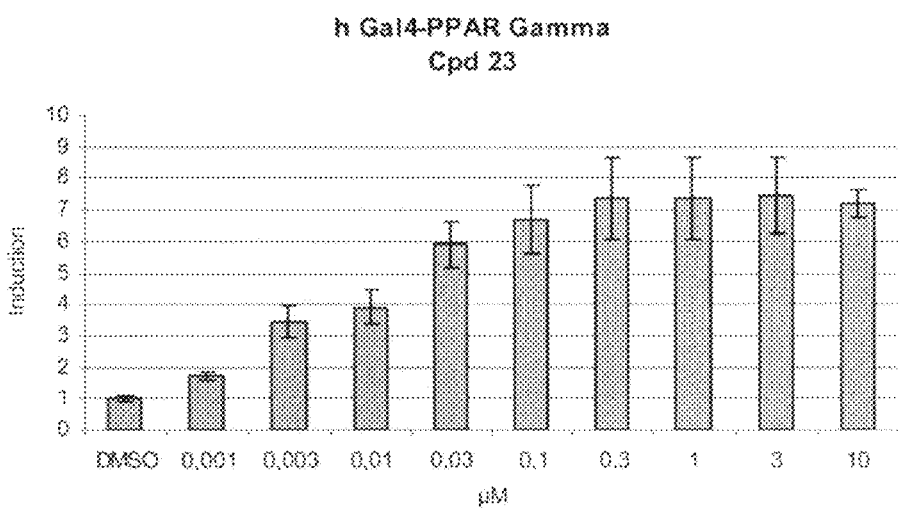
Figures 1, 60:
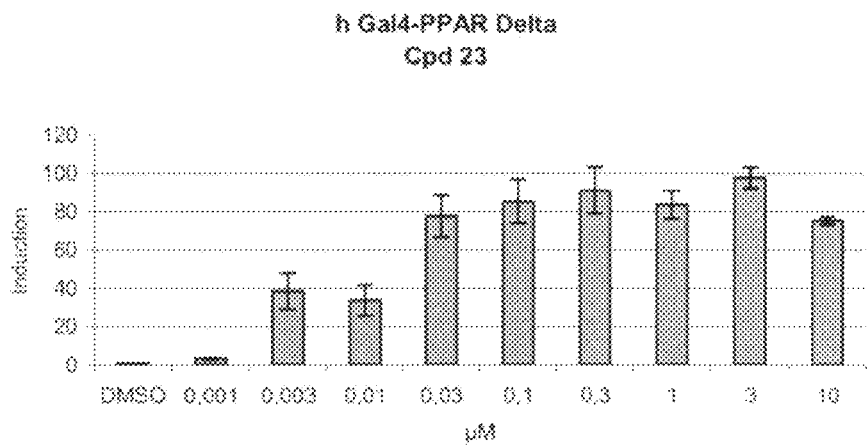
Figures 1, 61:
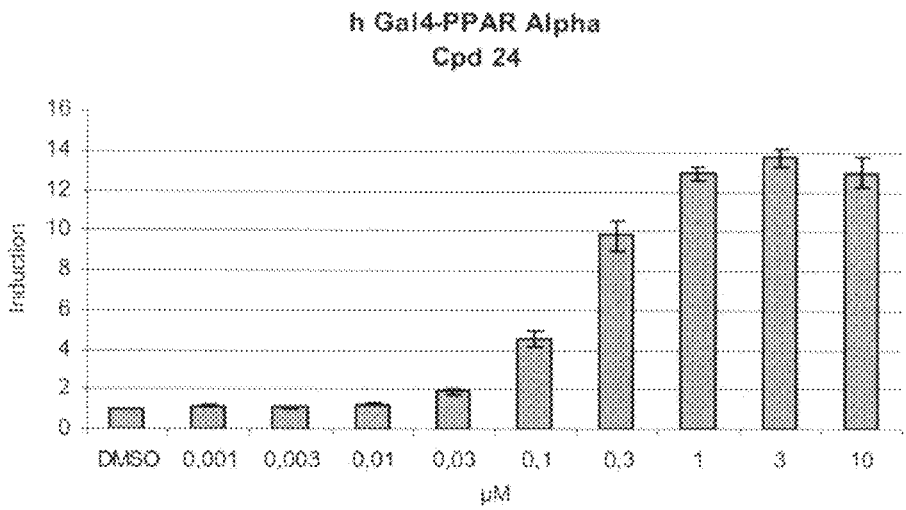
Figures 1, 62:
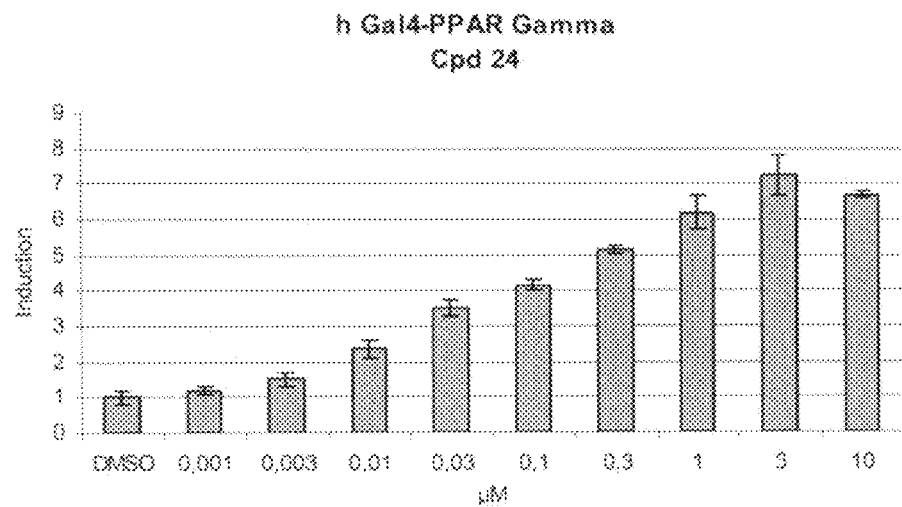
Figures 1, 63:
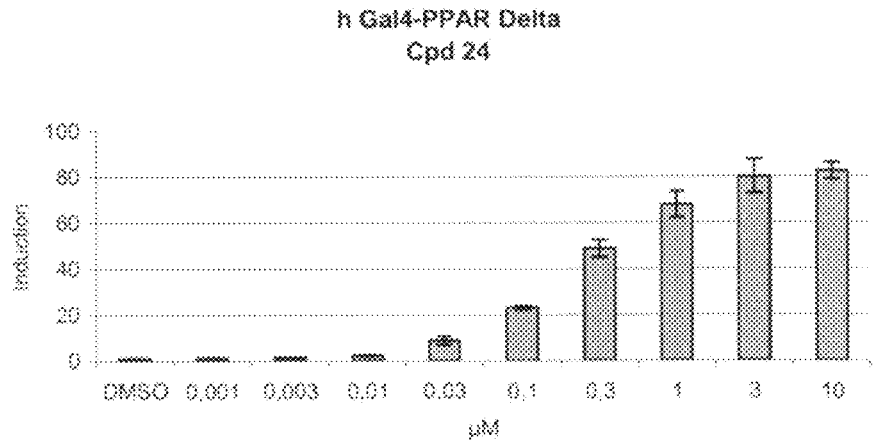
Figures 1, 64:
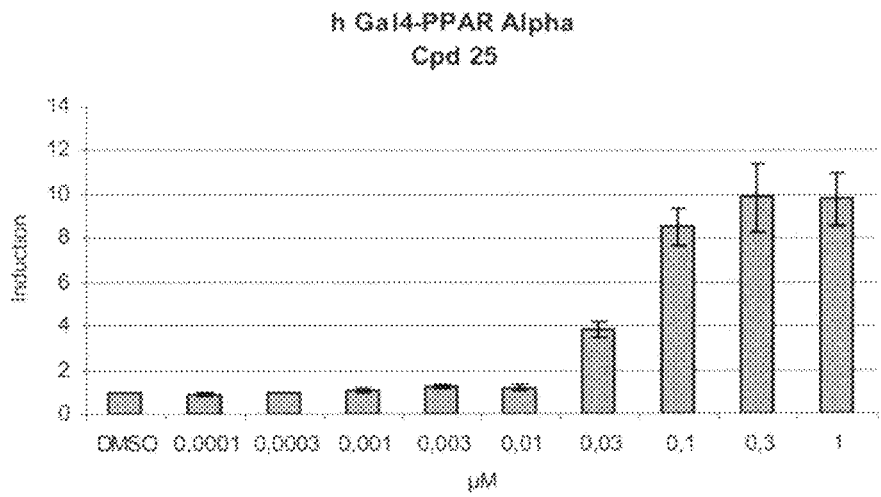
Figures 1, 65:
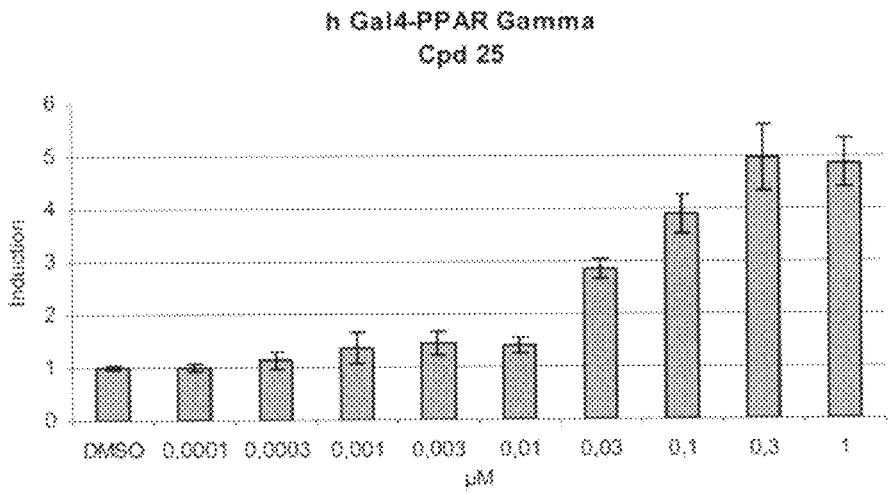
Figures 1, 66:
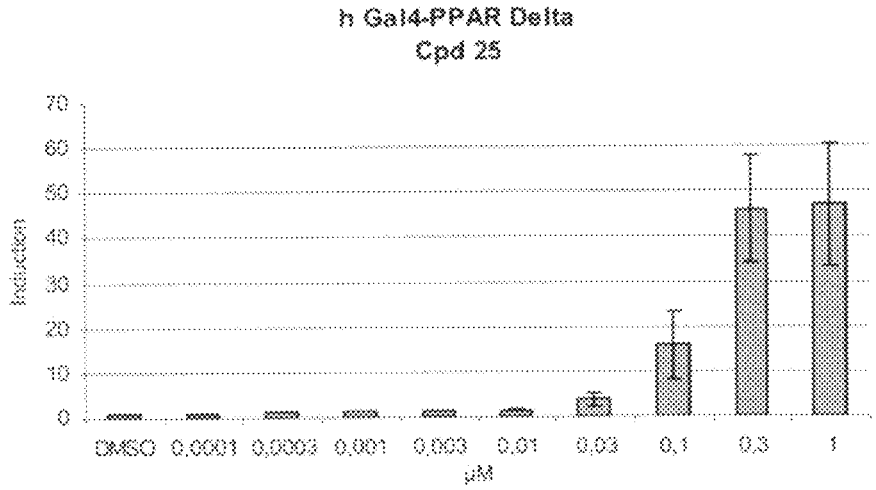
Figures 1, 2:
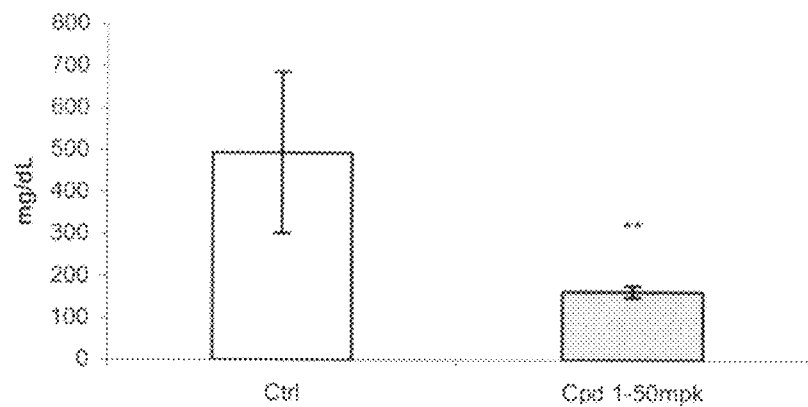
Figure 2:
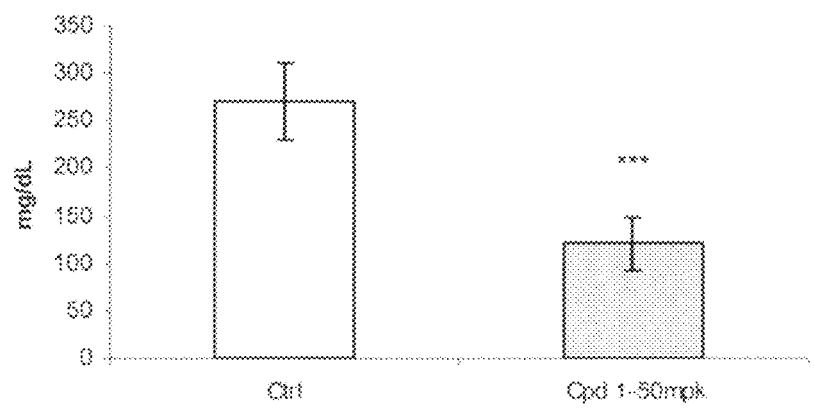
Figures 2, 3:
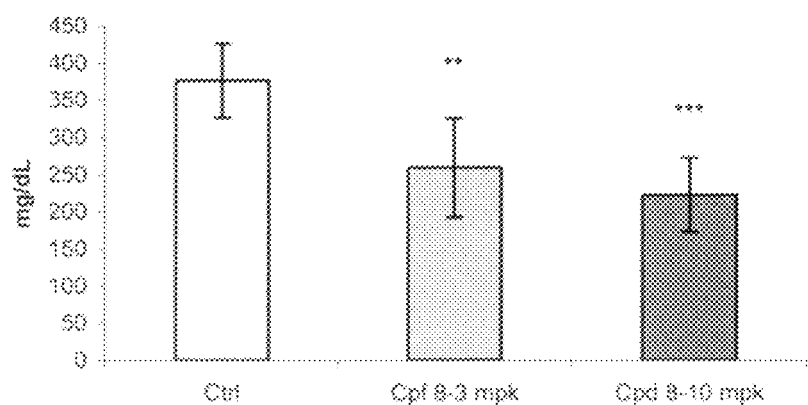
Figures 2, 3, 4:
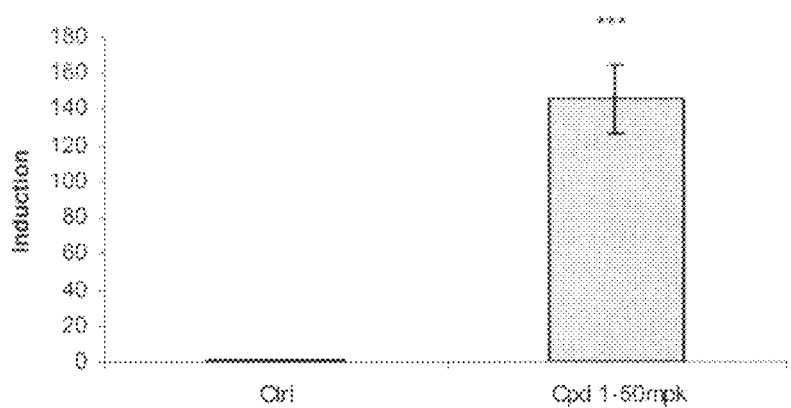
Figures 2, 3, 4, 5:
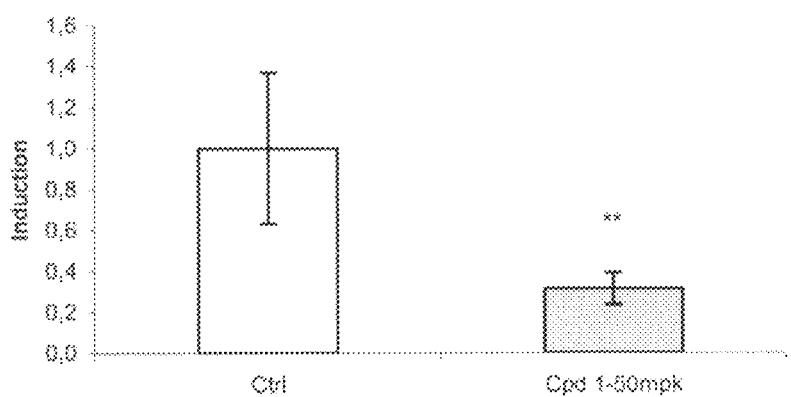
Figures 2, 3, 4, 5, 6:
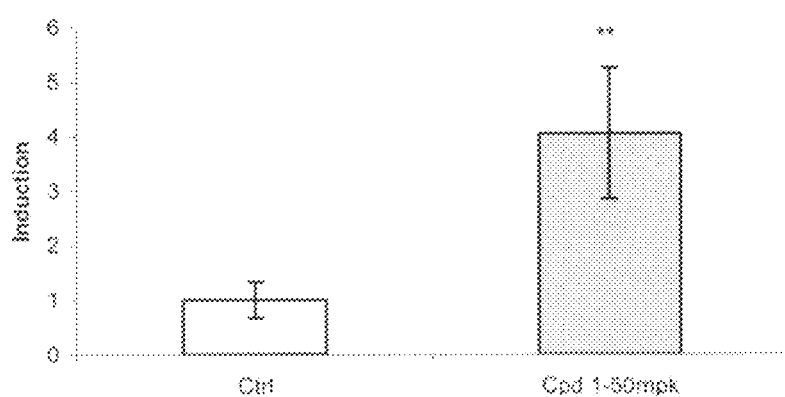
Figures 2, 3, 4, 5, 6, 7:
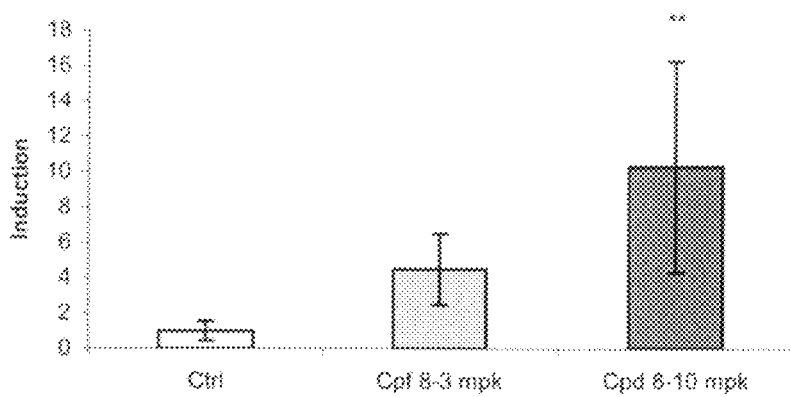
Figures 2, 3, 4, 5, 6, 7, 8:
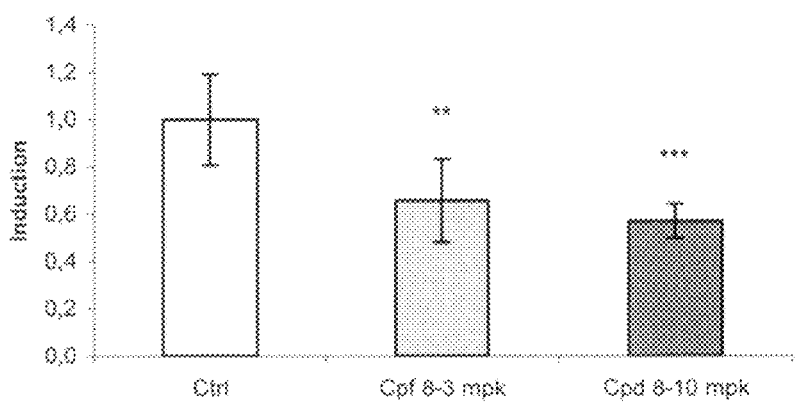
Figures 2, 3, 4, 5, 6, 7, 8, 9:
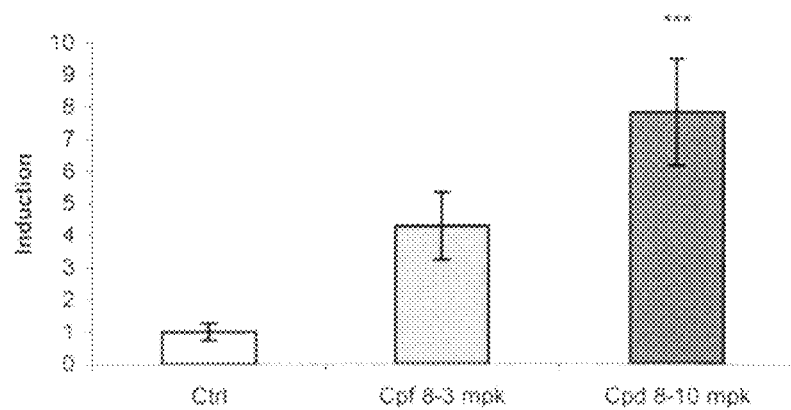
Figures 1, 3:
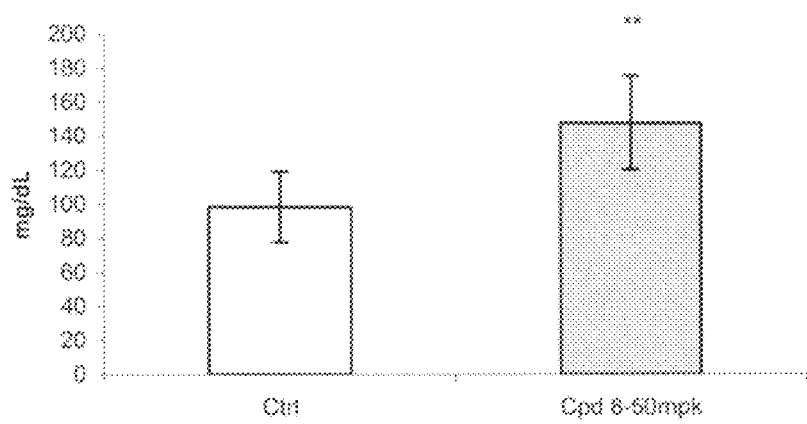
Figures 2, 3:
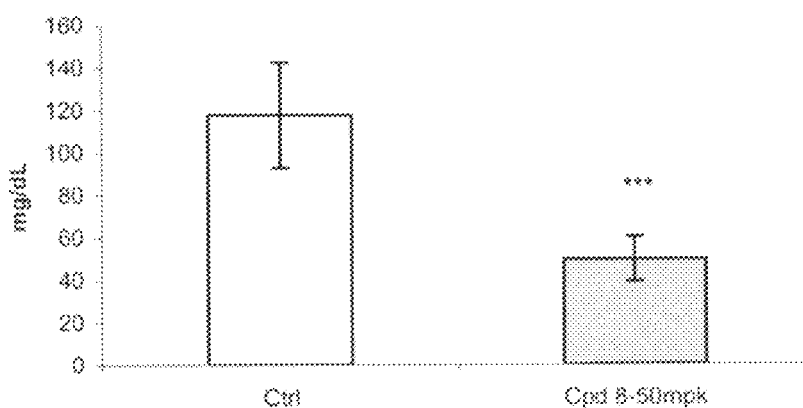
Figure 3:
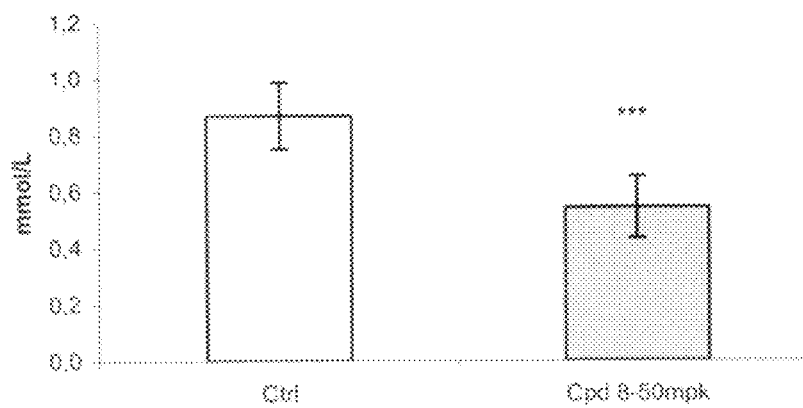
Figures 3, 4:
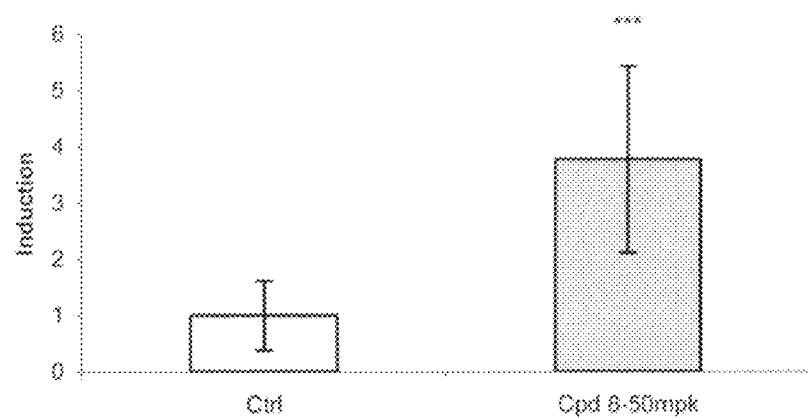
Figures 3, 4, 5:
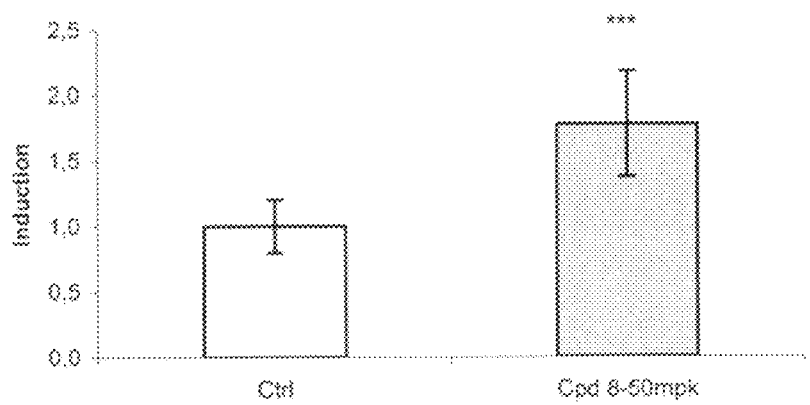
Figures 3, 4, 5, 6:
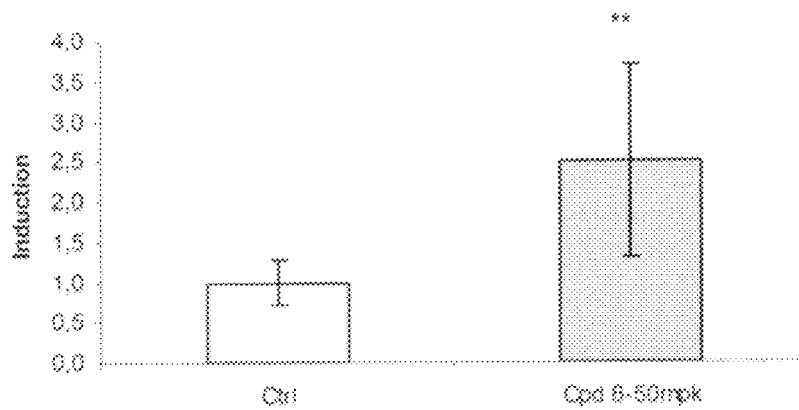
Figures 1, 4:
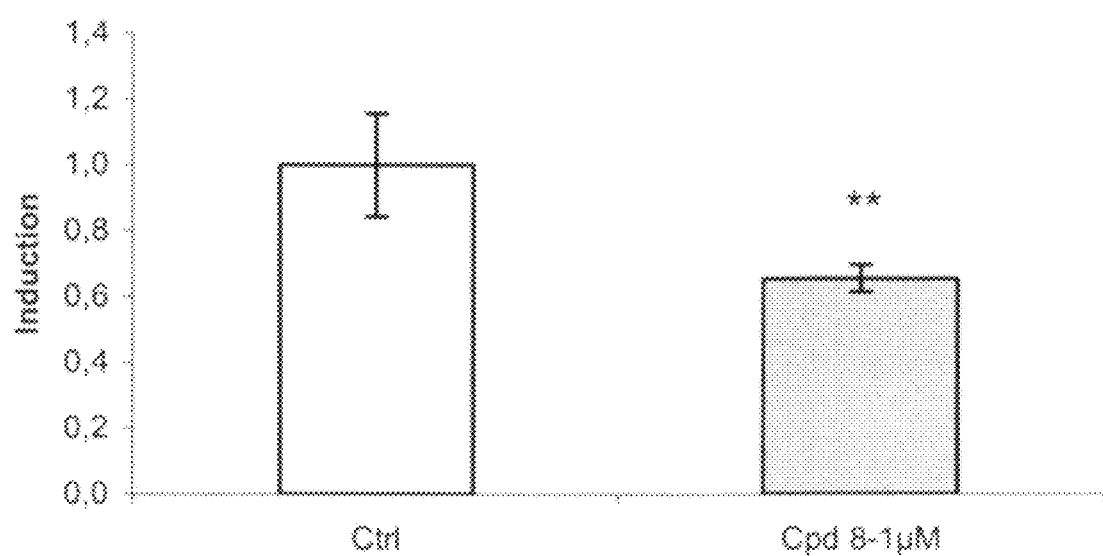

FIG. 2-4: Expression of PDK4 (Pyruvate Deshydrogenase Kinase, isoform 4) in the hepatic tissue of the E2/E2 mouse, after 8 days of treatment with compound 1, administered at 50 mpk
FIG. 2-5: Expression of ApoCIII (Apolipoprotein C3) in the hepatic tissue of the E2/E2 mouse, after 8 days of treatment with compound 1, administered at 50 mpk
FIG. 2-6: Expression of ACO (acyl-Coenzyme A oxidase 1, palmitoyl) in the hepatic tissue of the E2/E2 mouse, after 8 days of treatment with compound 1, administered at 50 mpk
FIG. 2-7: Expression of PDK4 in the hepatic tissue of the E2/E2 mouse, after 14 days of treatment with compound 8, administered at 3 to 10 mpk
FIG. 2-8: Expression of ApoCIII in the hepatic tissue of the E2/E2 mouse, after 14 days of treatment with compound 8, administered at 3 to 10 mpk
FIG. 2-9: Expression of ACO in the hepatic tissue of the E2/E2 mouse, after 14 days of treatment with compound 8, administered at 3 to 10 mpk
FIGS. 3-1 to 3-6: In vivo Evaluation, in the db/db Mice, of hypolipidemic properties and stimulative properties of the synthesis of HDL-cholesterol of the compounds according to the invention The effect of the compounds according to the invention is evaluated in vivo on the db/db mice by measuring the levels of HDL-cholesterol, triglycerides, and plasma free fatty acids after 28 days of a per os treatment with the compounds according to the invention. These parameters are compared to those obtained from the control animals (animals not treated with the compounds according to the invention): the measured difference shows the hypolipidemic effect of the compounds according to the invention.

FIG. 3-1: Plasma HDL-cholesterol levels after 28 days of treatment with compound 8, administrated at 50 mpk
FIG. 3-2: Plasma triglyceride levels after 28 days of treatment with compound 8, administered at 50 mpk;
FIG. 3-3: Plasma free fatty acid levels after 28 days of treatment with compound 8, administered at 50 mpk.

The effectiveness of the compounds according to the invention is also evaluated by measuring, in hepatic and muscular (skeletal) tissue, the expression of the genes involve in lipid and/or carbohydrate metabolism and in energy dissipation. Each level of gene expression is normalized in regarding the expression level of reference gene 36B4 in the hepatic tissue, or regarding the expression level of reference gene 18S in the gastrocnemius skeletal muscle. The induction factor, i.e. the ratio between the relative signal (induced by the compound according to the invention) and the average of relative values relating to the control group, is then calculated. The higher the induction factor is, the more the compound promotes gene expression. The final result is expressed as an average of the induction values obtained with each experimental group.

FIG. 3-4: Expression of PDK4 in the hepatic tissue of the db/db mouse, after 28 days of treatment with compound 8, administered at 50 mpk FIG. 3-5: Expression of ACO (acyl-Coenzyme A oxidase 1, palmitoyl) in the hepatic tissue of the db/db mouse, after 28 days of treatment with compound 8, administered at 50 mpk FIG. 3-6: Expression of UCP2 in the skeletal muscle tissue of the db/db mouse, after 28 days of treatment with compound 8, administered at 50 mpk FIGS. 4-1: In vitro evaluation of the anti-inflammatory properties of the compounds according to the invention by measuring the secretion of MCP1 by monocytes, treated with compounds according to the invention and stimulated with PMA The anti-inflammatory effects of the compounds according to the invention were evaluated by measuring the secretion of MCP1 (Monocyte chemotactic protein-1) by THP1 monocytes treated for 24 hours with the compounds according to the invention and stimulated simultaneously with PMA (Phorbol 12-myristate 13-acetate, which promotes an inflammatory response in cells and their differentiation into macrophages). The less MCP-1 is secreted, the more the compound according to the invention inhibits the inflammatory reaction.

FIG. 4-1: The secretion of MCP1 (Monocyte chemotactic protein-1) in THP1 monocytes, after 24 hours of treatment with compound 8, administered at 1 µM

STATISTICAL ANALYSES

The statistical studies consist of a Student's t-test)(°/°°/°°°) and/or a univariate ANOVA analysis of variance, followed by a Tukey test (*//*). The results are compared to a control group according to the value of parameter p: °/*: $p<0.05$; °°/: $p<0.01$; °°°/*: $p<0.001$.

EXAMPLES

Classical reagents and catalysts are commercially available (Aldrich, Alfa Aesar, Acros, Fluka or Lancaster).

Nuclear magnetic resonance spectrums of proton (NMR $^1$H) were measered on a Bruker AC300P spectrometer. Chemical shifts were expressed in ppm (parts per million) and the splitting of the NMR signals were described by with the usual abbreviations.

Example 1

General Procedure for the Synthesis of the Compounds According to the Invention Compounds according to the invention were obtained by reduction, following one of the procedures mentioned below, using the compounds claimed or described in US2005176808 patent.

General Procedure A: Reduction of Diphenylpropanones with Triethylsilane

To a solution of diphenylpropan-2-one in dichloromethane were added triethylsilane then trifluoroacetic acid drop by drop (7.5 equivalents). The reaction mixture was stirred at room temperature and the reaction follow-up was performed by thin layer chromatography. The reaction mixture was washed with water. The aqueous layer was extracted with dichloromethane. The combined organic layers were dried over magnesium sulfate, and concentrated under reduced pressure. The residue was column chromatographed (preparative HPLC, lichrospher (Merck) RP18 12 µm 100 Å, column: 25*250 mm).

General Procedure B: Reduction of Diphenylpropenones with Tetrachlorosilane

To a solution of diphenylpropan-2-one in acetonitrile were added sodium iodide, then tetrachlorosilane drop by drop. The reaction mixture was stirred at room temperature and the reaction follow-up was performed by thin layer chromatography. After 30 minutes to 2 hours, the mixture was partitioned between chloroform and water. The aqueous layer was extracted with chloroform. The combined organic layers were dried over sodium sulfite, then dried over magnesium sulfate and concentrated under reduced pressure. The residue was columns chromatographed (preparative HPLC, lichrospher (Merck) RP18 12 µm 100 Å, column: 25*250 mm).

General Procedure C: Synthesis of Oximes and Oxime Ethers

To a solution of diphenylpropan-3-one in pyridine was added O-alkylhydroxylamine hydrochloride. After 16 hours of reflux, the mixture was concentrated under reduced pressure. The residue was column chromatographed.

General Procedure D: Alcohol Synthesis

To a solution of diphenylpropan-3-one in ethanol was added sodium borohydride. The reaction mixture was stirred for 16 hours at 50° C. (122° F.). After cooling down, the reaction mixture was hydrolysed and concentrated under reduced pressure. The residue was partitioned between diluted hydrochloric acid solution and dichloromethane.

The organic layer was washed with water, dried over magnesium sulfate and concentrated under reduced pressure. The residue was column chromatographed (Preparative HPLC, lichrospher (Merck) RP18 12 µm 100 Å, column: 25*250 mm).

General Procedure E: Ether Synthesis

A solution of diphenylpropan-3-ol in a water/alcohol mixture in presence of a catalytic amount of trifluoroacetic acid was stirred vigorously at the appropriate temperature, then concentrated under reduced pressure. The residue was extracted with dichloromethane. The combined organic layers were dried over magnesium sulfate, filtered then concentrated under reduced pressure. The residue was column chromatographed (preparative HPLC, lichrospher (Merck) RP18 12 µm 100 Å, column: 25*250 mm).

Example 2

Synthesis of the Compounds According to the Invention

Compound 1: 2-[2,6-dimethyl-4-[3-[4-(methylthio)phenyl]-3-oxo-propyl]phenoxyl]-2-methylpropanoic acid

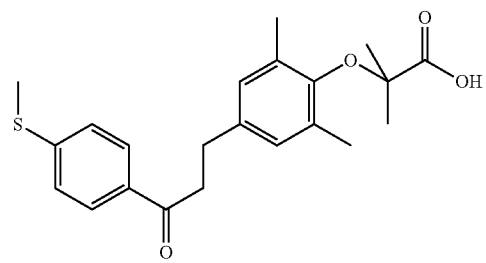

This compound was prepared following the general procedure A, using 2-[2,6-dimethyl-4-[3-[4-(methylthio)phenyl]-3-oxo-prop-2-enyl]phenoxy]-2-methylpropanoic acid, and 1.3 equivalent amounts of triethylsilane;

Appearance: white solid; F=109-110° C.
NMR ¹H (300 MHz, CDCl₃, δ in ppm): 1.42 (s, 6H), 2.19 (s, 6H), 2.53 (s, 3H), 2.89 (t, 2H, J=7.59 Hz), 3.25 (t, 2H, J=7.59 Hz), 6.89 (s, 2H), 7.31 (d, 2H, J=8.17 Hz), 7.88 (d, 2H, J=8.17 Hz).
MS(ES-MS): 385.3 (M−1).

Compound 2: 2-[2,6-dimethyl-4-[3-[2-(hexyloxy) phenyl]-3-oxo-propyl]phenoxy]-2-methylpropanoic acid

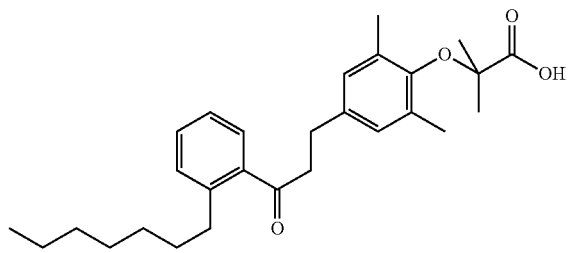

This compound was prepared following the general procedure A, using 2-[2,6-dimethyl-4-[3-[2-(hexyloxy)phenyl]-3-oxo-prop-2-enyl]phenoxy]-2-methylpropanoic acid, and 1 equivalent amount of triethylsilane;
Appearance: white solid; F=73-75° C.
NMR ¹H (300 MHz, CDCl₃, δ in ppm): 0.89 (t, 3H, J=6.72 Hz), 1.32 (m, 4H), 1.45 (m, 2H), 1.52 (s, 6H), 1.82 (m, 2H), 2.21 (s, 6H), 2.93 (t, 2H, J=8.19 Hz), 3.33 (t, 2H, J=8.19 Hz), 4.05 (t, 2H, J=6.42 Hz), 6.87 (s, 2H), 6.95 (m, 1H), 7.01 (m, 1H), 7.44 (m, 1H), 7.68 (dd, 1H, J=1.77 Hz, J=7.89 Hz).
MS(ES-MS): 439.4 (M−1).

Compound 3: 2-[2,6-dimethyl-4-[3-[4-(methylthio) phenyl]-3-benzyloxypropyl]phenoxy]-2-methylpropanoic acid

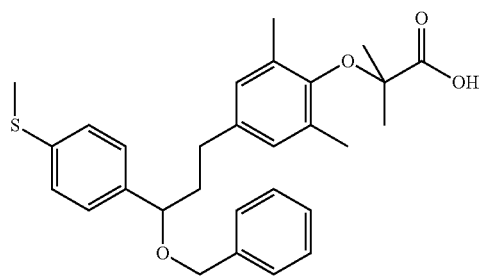

To a solution of 2-[2,6-dimethyl-4-[3-[4-(methylthio)phenyl]-3-hydroxypropyl]phenoxy]-2-methylpropanoic acid in N,N-dimethylformamide at 0° C. was added sodium hydride (2.2 equivalents) for 15 minutes. Benzyle bromide (2.2 equivalents) is then added and the mixture was stirred for 16 hours at room temperature. The mixture was partitioned between a saturated ammonium chloride solution and ethyl acetate. The combined organic layers were dried over magnesium sulfate, filtered then concentrated under reduced pressure.
The residue was diluted in ethanol in presence of 2N sodium hydroxide solution (20 eq.). The reaction mixture was stirred for 6 hours and concentrated under reduced pressure. The residue was acidified with a diluted hydrochloric acid solution, then extracted with dichloromethane. The combined organic layers were dried over magnesium sulfate, filtered then concentrated under reduced pressure. The residue was column chromatographed (preparative HPLC, lichrospher (Merck) RP18 12 μm 100 Å, column: 25*250 mm).
Appearance: off-white solid; F=69-71° C.
NMR ¹H (300 MHz, CDCl₃, δ in ppm): 1.49 (s, 6H), 1.90 (m, 1H), 2.14 (m, 1H), 2.19 (s, 6H), 2.52 (m, 1H), 2.52 (s, 3H), 2.68 (m, 1H), 4.24 (d, 1H, J=11.8 Hz), 4.28 (t, 1H, J=5.25 Hz), 4.47 (d, 1H, J=11.8 Hz), 6.77 (s, 2H), 7.31 (m, 9H).
MS(ES-MS): 477.3 (M−1).

Compound 4: 2-[2,6-dimethyl-4-[3-[4-(methylthio) phenyl]-3-hydroxypropyl]phenoxyl]-2-methylpropanoic acid

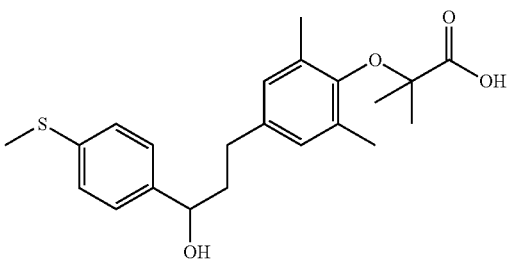

This compound was prepared following the general procedure D, using 2-[2,6-dimethyl-4-[3-[4-(methylthio)phenyl]-3-oxo-propyl]phenoxy]-2-methylpropanoic acid, and 3 equivalent amounts of sodium borohydride;
Appearance: yellowish solid; F=49-51° C.
NMR ¹H (300 MHz, CDCl₃, δ in ppm): 1.52 (s, 6H), 2.04 (m, 2H), 2.22 (s, 6H), 2.5 (s, 3H), 2.63 (m, 2H), 4.66 (dd, 1H, J=5.7 Hz, J=7.5 Hz), 6.84 (s, 2H), 7.27 (m, 4H).
MS(ES-MS): 389.3 (M+1).

Compound 5: 2-[2,6-dimethyl-4-[3-[4-(methylthio) phenyl]-3-methoxyimino-propyl]phenoxyl]-2-methylpropanoic acid

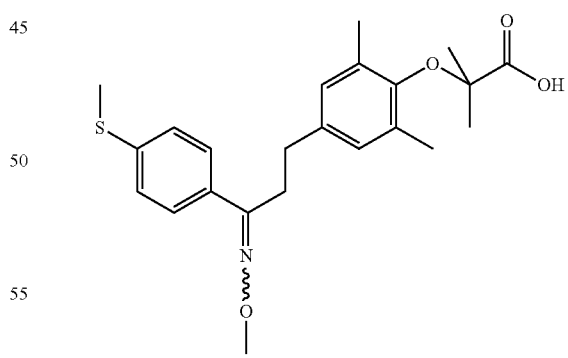

This compound was prepared following the general procedure C, using 2-[2,6-dimethyl-4-[3-[4-(methylthio)phenyl]-3-oxo-propyl]phenoxy]-2-methyl propanoic acid;
Appearance: yellowish viscous oil.
NMR ¹H (300 MHz, CDCl₃, δ in ppm): 1.50 (s, 6H), 2.21 (s, 6H), 2.49 (s, 3H), 2.73 (m, 2H), 2.96 (m, 2H), 3.99 (s, 3H), 6.84 (s, 2H), 7.20 (d, 2H, J=8.47 Hz), 7.51 (d, 2H, J=8.47 Hz).
MS(MALDI TOF): 416.4 (M+1).

Compound 6: 2-[2,6-dimethyl-4-[3-[4-(methoxy) phenyl]-3-oxo-propyl]phenoxyl]-2-methylpropanoic acid

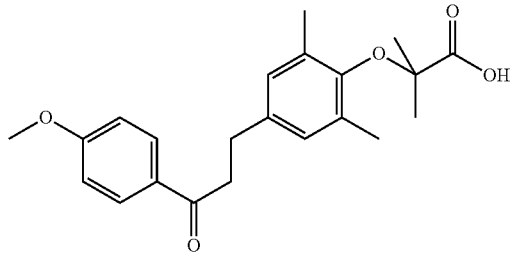

This compound was prepared floowing the general procedure B, using 2-[2,6-dimethyl-4-[3-[4-(methoxy)phenyl]-3-oxo-prop-2-enyl]phenoxy]-2-methylpropanoic acid, and 5 equivalent amounts of sodium iodide and 5 equivalent amounts of tetrachlorosilane;

Appearance: white solid; F=279-281° C.

NMR $^1$H (300 MHz, CDCl$_3$, δ ppm): 1.52 (s, 6H), 2.22 (s, 6H), 2.94 (t, 2H, J=7.59 Hz), 3.20 (t, 2H, J=7.59 Hz), 3.87 (s, 3H), 6.88 (s, 2H), 6.93 (d, 2H, J=8.76 Hz), 7.95 (d, 2H, J=8.76 Hz).

MS(ES-MS): 369.3 (M−1).

Compound 7: 2-[2,6-dimethyl-4-[3-[4-(methylthio) phenyl]-3-oxo-propyl]phenoxy]-2-methylethanoic acid

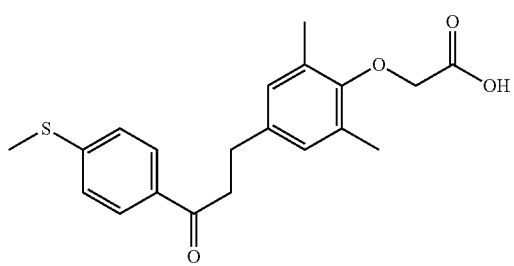

This compound was prepared following the general procedure B, using 2,6-dimethyl-4-[3-[4-(methoxy)phenyl]-3-oxo-prop-2-enyl]phenoxyethanoic acid, and 5 equivalent amounts of sodium iodide and 5 equivalent amounts of tetrachlorosilane;

Appearance: white solid; F=138-139° C.

NMR $^1$H (300 MHz, CDCl$_3$, δ ppm): 2.28 (s, 6H), 2.54 (s, 3H), 2.96 (t, 2H, J=7.60 Hz), 3.24 (t, 2H, J=7.60 Hz), 4.45 (s, 2H), 6.92 (s, 2H), 7.27 (d, 2H, J=8.47 Hz), 7.88 (d, 2H, J=8.47 Hz).

MS(ES-MS): 357.2 (M−1).

Compound 8: 2-[2,6-dimethyl-4-[3-[4-(propyloxy) phenyl]-3-oxo-propyl]phenoxyl]-2-methylpropanoic acid

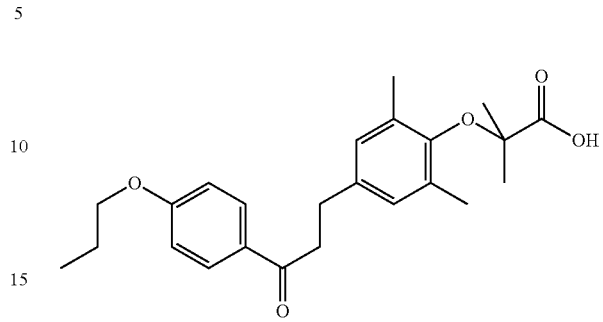

This compound was prepared following the general procedure B, using 2-[2,6-dimethyl-4-[3-[4-(propyloxy)phenyl]-3-oxo-prop-2-enyl]phenoxy]-2-methylpropanoic acid, and 5 equivalent amounts of sodium iodide and 5 equivalent amounts of tetrachlorosilane;

Appearance: white solid; F=89-92° C.

NMR $^1$H (300 MHz, CDCl$_3$, δ ppm): 1.06 (t, 3H, J=7.30 Hz), 1.54 (s, 6H), 1.85 (m, 2H), 2.23 (s, 6H), 2.95 (t, 2H, J=7.75 Hz), 3.22 (t, 2H, J=7.75 Hz), 3.99 (t, 2H, J=6.57 Hz), 6.89 (s, 2H), 6.93 (d, 2H, J=8.91 Hz), 7.95 (d, 2H, J=8.91 Hz).

MS(ES-MS): 397.3 (M−1).

Compound 9: 2-[2-methyl-4-[3-[4-(heptyl)phenyl]-3-oxo-propyl]phenoxy]-2-methylpropanoic acid

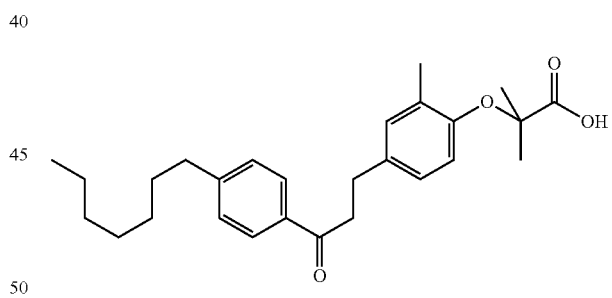

This compound was prepared following the general procedure B, using 2-[2-methyl-4-[3-[4-(heptyl)phenyl]-3-oxo-prop-2-enyl]phenoxy]-2-methylpropanoic acid, and 5 equivalent amounts of sodium iodide and 5 equivalent amounts of tetrachlorosilane;

Appearance: white solid; F=53-54° C.

NMR $^1$H (300 MHz, CDCl$_3$, δ ppm): 0.89 (t, 3H, J=6.72 Hz), 1.29 (m, 8H), 1.61 (s, 6H), 1.62 (m, 2H), 2.24 (s, 3H), 2.66 (t, 2H, J=7.74 Hz), 2.99 (t, 2H, J=7.59 Hz), 3.26 (t, 2H, J=7.59 Hz), 6.78 (d, 1H, J=8.46 Hz), 7.01 (d, 1H, J=8.46 Hz), 7.08 (s, 1H), 7.26 (d, 2H, J=8.16 Hz), 7.89 (d, 2H, J=8.16 Hz).

MS(ES-MS): 423.3 (M−1).

Compound 10: 2-[2,6-dimethyl-4-[3-[4-(methylthio)phenyl]-3-ethyloxypropyl]phenoxy]-2-methylpropanoic acid

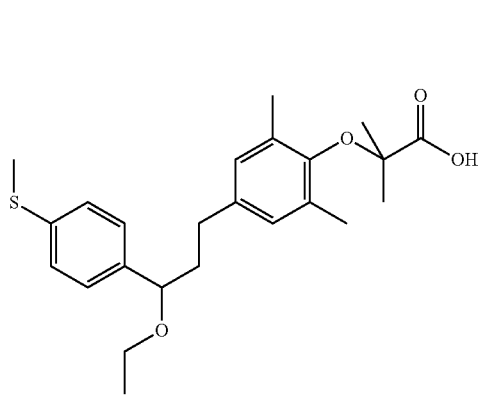

This compound was prepared following the general procedure E, using 2-[2,6-dimethyl-4-[3-[4-(methylthio)phenyl]-3-hydroxypropyl]phenoxy]-2-methylpropanoic acid at reflux in a 2/3:1/3 ethanol/water mixture for 72 hours;

Appearance: viscous oil.

NMR $^1$H (300 MHz, CDCl$_3$, δ in ppm): 1.19 (t, 3H, J=7.02 Hz), 1.48 (s, 6H), 1.87 (m, 1H), 2.07 (m, 1H), 2.19 (s, 6H), 2.5 (s, 3H), 2.53 (m, 1H), 2.64 (m, 1H), 3.34 (m, 2H), 4.14 (dd, 1H, J=2.34 Hz, J=5.55 Hz), 6.8 (s, 2H), 7.24 (m, 4H).

MS(ES-MS): 417.4 (M+1).

Compound 11: 2-[2,6-dimethyl-4-[3-[2-(trifluoromethyl)phenyl]-3-oxo-propyl]phenoxy]-2-methylpropanoic acid

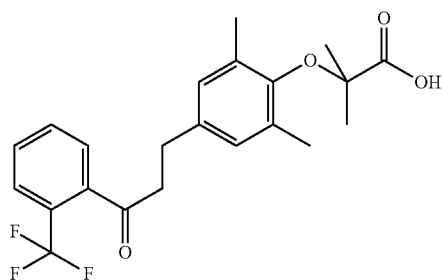

This compound was prepared following the general procedure A, using 2-[2,6-dimethyl-4-[3-[2-(trifluoromethyl)phenyl]-3-oxo-prop-2-enyl]phenoxy]-2-methylpropanoic acid, and 1 equivalent amount of triethylsilane;

Appearance: yellowish viscous oil.

NMR $^1$H (300 MHz, CDCl$_3$, δ ppm): 1.53 (s, 6H), 2.22 (s, 6H), 2.95 (t, 2H, J=7.30 Hz), 3.15 (t, 2H, J=7.30 Hz), 6.86 (s, 2H), 7.32 (m, 1H), 7.56 (m, 2H), 7.71 (m, 1H).

MS(ES-MS): 407.3 (M−1).

Compound 12: 2-[2,6-dimethyl-4-[3-[4-(methylthio)phenyl]propyl]phenoxyl]-2-methylpropanoic acid

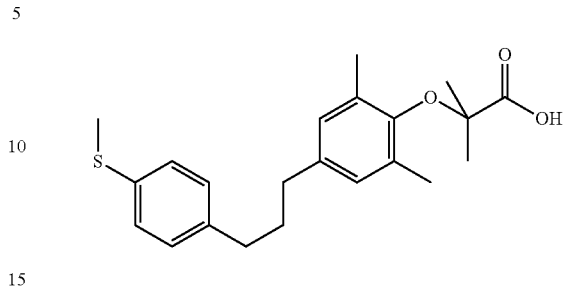

To a solution of 2-[2,6-dimethyl-4-[3-[4-(methylthio)phenyl]-3-oxo-prop-2-enyl]phenoxy]-2-methylpropanoic acid in trifluoroacetic acid was added triethylsilane (2.7 equivalents) drop by drop. The reaction mixture was stirred at room temperature for 16 hours. The reaction follow-up was performed by thin layer chromatography. The mixture was washed with water. The aqueous layer was extracted with dichloromethane. The combined organic layers were dried over magnesium sulfate, then concentrated under reduced pressure. The residue was column chromatographed (Eluant: dichloromethane 95, methanol 5). Appearance: white solid; F=181-182° C.

NMR $^1$H (300 MHz, DMSO-d$_6$, δ ppm): 1.24 (s, 6H), 1.81 (m, 2H), 2.16 (s, 6H), 2.42 (m, 2H), 2.44 (s, 3H), 2.54 (m, 2H), 6.73 (s, 2H), 7.15 (m, 4H).

MS(ES-MS): 371.4 (M−1).

Compound 13: 2-[2,6-dimethyl-4-[3-[4-(methylthio)phenyl]-3-oxo-propyl]phenoxy]-2-methylpropanoic acid isopropyl ester

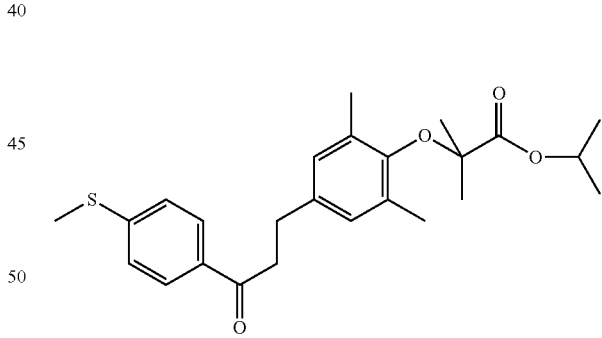

This compound was prepared following the general procedure A, using 2-[2,6-dimethyl-4-[3-[4-(methylthio)phenyl]-3-oxo-prop-2-enyl]phenoxy]-2-methylpropanoic acid isopropyl ester, and 1 equivalent amount of triethylsilane;

Appearance: white solid; F=64-65° C.

NMR $^1$H (300 MHz, CDCl$_3$, δ ppm): 1.34 (d, 6H, J=6.5 Hz), 1.45 (s, 6H), 2.19 (s, 6H), 2.54 (s, 3H), 2.93 (t, 2H, J=7.89 Hz), 3.21 (t, 2H, J=7.89 Hz), 5.14 (sep, 1H, J=6.15 Hz), 6.84 (s, 2H), 7.26 (d, 2H, J=8.49 Hz), 7.89 (d, 2H, J=8.49 Hz).

MS(MALDI-TOF): 429.3 (M+1).

Compound 14: 2-[2,6-dimethyl-4-[3-[4-(methylthio)phenyl]-3-hydroxyimino-propyl]phenoxy]-2-methylpropanoic acid

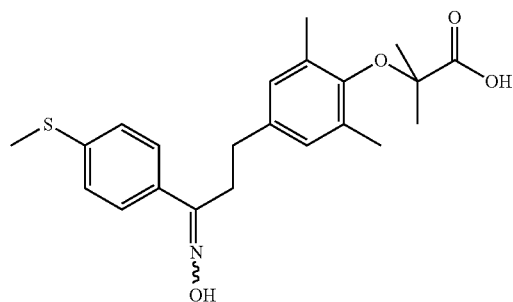

This compound was prepared following the general procedure C, using 2-[2,6-dimethyl-4-[3-[4-(methylthio)phenyl]-3-oxo-propyl]phenoxy]-2-methylpropanoic acid;

Appearance: white solid; F=144-147° C.

NMR $^1$H (300 MHz, DMSO-$d_6$, δ ppm): 1.31 (s, 6H), 2.11 (s, 6H), 2.49 (s, 3H), 2.61 (dd, 2H, J=7,17 Hz, J=8.76 Hz), 2.91 (t, 2H, J=8.47 Hz), 6.85 (s, 2H), 7.23 (d, 2H, J=8.47 Hz), 7.54 (d, 2H, J=8.47 Hz), 11.21 (s, 1H), 12.81 (s, 1H).

MS(ES-MS): 400.3 (M−1).

Compound 15: 2-[2,6-dimethyl-4-[3-[4-(propyloxy)phenyl]-3-hydroxy-propyl]phenoxy]-2-methylpropanoic acid

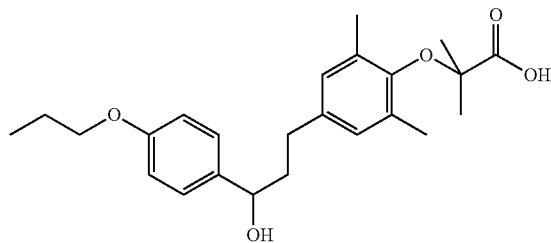

This compound was prepared following the general procedure D, using 2-[2,6-dimethyl-4-[3-[4-(propyloxy)phenyl]-3-oxo-propyl]phenoxy]-2-methylpropanoic acid;

Appearance: yellowish viscous oil.

NMR $^1$H (300 MHz, CDCl$_3$, δ ppm): 1.05 (t, 3H, J=7.46 Hz), 1.50 (s, 6H), 1.82 (m, 2H), 2.04 (m, 2H), 2.20 (s, 6H), 2.56 (m, 2H), 3.93 (t, 2H, J=6.57 Hz), 4.63 (t, 1H, J=6.57 Hz), 6.81 (s, 2H), 6.88 (d, 2H, J=8.61 Hz), 7.25 (d, 2H, J=8.61 Hz).

MS(ES-MS): 399.4 (M−1).

Compound 16: 2-[2,6-dimethyl-4-[3-[2-(trifluoromethoxy)phenyl]-3-oxo-propyl]phenoxy]-2-methylpropanoic acid

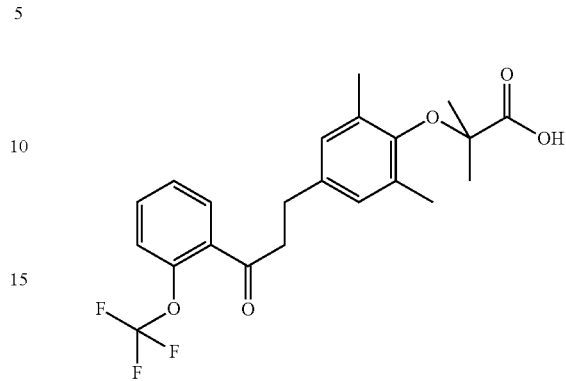

This compound was prepared following the general procedure B, using 2-[2,6-dimethyl-4-[3-[2-(trifluoromethoxy)phenyl]-3-oxo-prop-2-enyl]phenoxy]-2-methylpropanoic acid, and 5 equivalent amounts of sodium iodide and 5 equivalent amounts of tetrachlorosilane;

Appearance: yellowish viscous oil.

NMR $^1$H (300 MHz, CDCl$_3$, δ ppm): 1.53 (s, 6H), 2.21 (s, 6H), 2.94 (t, 2H, J=7.46 Hz), 3.23 (t, 2H, J=7.46 Hz), 6.85 (s, 2H), 7.36 (m, 2H), 7.54 (m, 1H), 7.63 (dd,1H, J=1.74 Hz, J=7.59 Hz).

MS(ES-MS): 423.0 (M−1).

Compound 17: 2-[2,6-dimethyl-4-[3-[4-(methylthio)phenyl]-3-methoxypropyl]phenoxy]-2-methylpropanoic acid

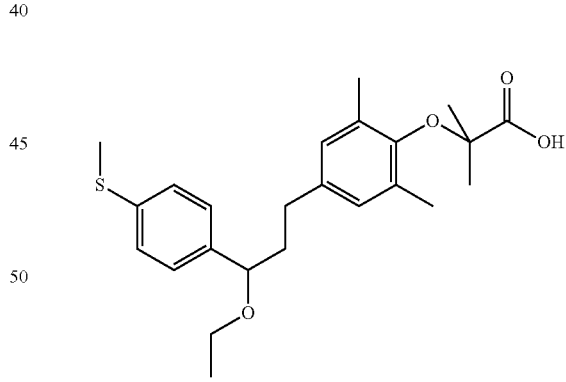

This compound was prepared following the general procedure E, using 2-[2,6-dimethyl-4-[3-[4-(methylthio)phenyl]-3-hydroxy-propyl]phenoxy]-2-methylpropanoic acid at reflux in a 2/3:1/3 ethanol/water mixture for 16 hours;

Appearance: viscous oil.

NMR $^1$H (300 MHz, CDCl$_3$, δ in ppm): 1.51 (s, 6H), 1.89 (m, 1H), 2.08 (m, 1H), 2.21 (s, 6H), 2.5 (s, 3H), 1.56 (m, 2H), 3.22 (s, 3H), 4.05 (dd, 1H, J=5.82 Hz, J=7.32 Hz), 6.79 (s, 2H), 7.26 (d, 2H, J=8.46 Hz), 7.21 (d, 2H, J=8.46 Hz).

MS(ES-MS): 401.3 (M−1).

Compound 18: 2-[2,6-dimethyl-4-[2,3-dihydro-4H-1-benzothiopyran-4-one-2-yl]phenoxyl]-2-methylpropanoic acid

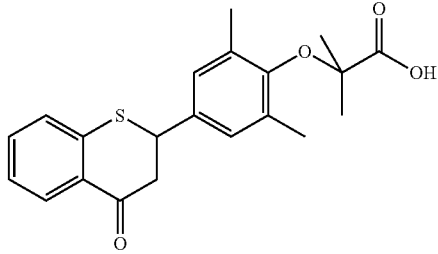

This compound was prepared following the general procedure B, using 2-[2,6-dimethyl-4-[3-[2-(methylthio)phenyl]-3-oxo-prop-2-enyl]phenoxy]-2-methylpropanoic acid, and 6 equivalent amounts of sodium iodide and 6 equivalent amounts of tetrachlorosilane;

Appearance: yellowish solid; F=60-63° C.

NMR $^1$H (300 MHz, CDCl$_3$, δ ppm): 1.53 (s, 6H), 2.26 (s, 6H), 3.18 (dd, 1H, J=3.35 Hz, J=16.37 Hz), 3.28 (dd, 1H, J=12.87 Hz, J=16.37 Hz), 4.62 (dd, 1H, J=3.35 Hz, J=12.87 Hz), 7.06 (s, 2H), 7.22 (d, 1H, J=7.02 Hz), 7.29 (m, 1H), 7.43 (m, 1H), 8.15 (d, 1H, J=7.89 Hz).

MS(ES-MS): 369.1 (M−1).

Compound 19: 2-[2-methyl-4-[3-[4-(propylthio)phenyl]-3-oxo-propyl]phenoxy]-2-methylpropanoic acid

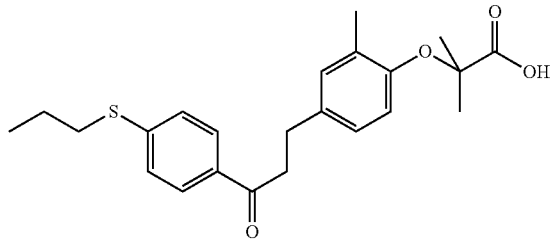

This compound was prepared following the general procedure B, using 2-methyl-2-(2-methyl-4-(3-oxo-3-(4-(propylthio)phenyl)prop-1-enyl)phenoxy)propanoic acid tertiobutyl ester, and 3 equivalents amounts of sodium iodide and 3 equivalent amounts of tetrachlorosilane;

Appearance: viscous oil.

NMR $^1$H (300 MHz, CDCl$_3$, δ in ppm): 1.07 (t, 3H, J=7.3 Hz), 1.61 (s, 6H), 1.73 (m, 2H), 2.24 (s, 3H), 2.98 (m, 4H), 3.23 (t, 2H, J=7.32 Hz), 6.76 (d, 1H, J=8.19 Hz), 6.97 (d, 1H, J=8.19 Hz), 7.06 (s, 1H), 7.29 (d, 2H, J=8.76 Hz), 7.86 (d, 2H, J=8.76 Hz).

MS(ES-MS): 392.2 (M−1).

Compound 20: 2-[3-[3-[4-methylthiophenyl]-3-oxo-propyl]phenoxy]-2-methylpropanoic acid

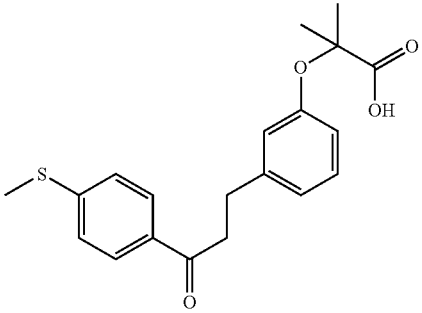

This compound was prepared following the general procedure B, using 2-[3-[3-[4-(methylthio)pheny]-3-oxo-prop-2-enyl]phenoxy]-2-methylpropanoic acid, and 7 equivalent amounts of sodium iodide and 7 equivalent amounts of tetrachlorosilane;

Appearance: white solid; F=67-68° C.

NMR $^1$H (300 MHz, CDCl$_3$, δ ppm): 1.62 (s, 6H), 2.51 (s, 3H), 3.01 (t, 2H, J=7.60 Hz), 3.23 (t, 2H, J=7.60 Hz), 6.76 (d, 1H, J=8.16 Hz), 6.86 (s, 1H), 6.93 (d, 1H, J=7.62 Hz), 7.16 (t, 1H, J=7.89 Hz), 7.25 (d, 2H, J=8.48 Hz), 7.85 (d, 2H, J=8.48 Hz).

MS(ES-MS): 357.3 (M−1).

Compound 21: 2-[4-[3-[4-(methylphenyl]-3-oxo-propyl]phenoxy]-2-methylpropanoic acid

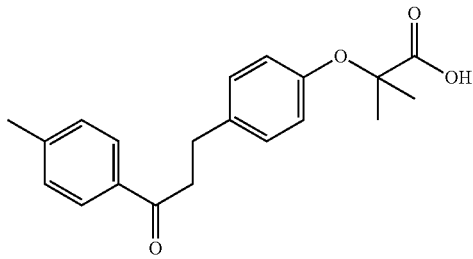

This compound was prepared following the general procedure B, using 2-[4-[3-[4-(methylphenyl]-3-oxo-prop-2-enyl]phenoxy]-2-methylpropanoic acid, and 5 equivalent amounts of sodium iodide and 5 equivalent amounts of tetrachlorosilane;

Appearance: white solid; F=124-125° C.

NMR $^1$H (300 MHz, CDCl$_3$, δ ppm): 1.56 (s, 6H), 2.43 (s, 3H), 3.04 (t, 2H, J=7.52 Hz), 3.27 (t, 2H, J=7.52 Hz), 6.9 (d, 2H, J=8.34 Hz), 7.19 (d, 2H, J=8.34 Hz), 7.24 (d, 2H, J=8.19 Hz), 7.87 (d, 2H, J=8.19 Hz).

MS(ES-MS): 325.3 (M−1).

Compound 23: 2-[2,6-dimethyl-4-[3-[4-(methylthio) phenyl]-3-butyloxypropyl]phenoxyl]-2-methylpropanoic acid

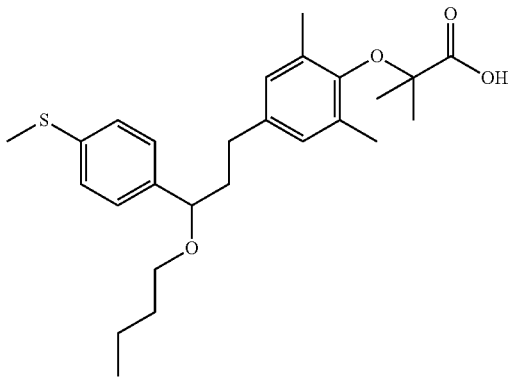

This compound was prepared following the general procedure E, using 2-[2,6-dimethyl-4-[3-[4-(methylthio)phenyl]-3-hydroxypropyl]phenoxy]-2-methylpropanoic acid in 50/50 butanol/water at 70° C. for 32 hours;

Appearance: viscous oil.

NMR $^1$H (300 MHz, CDCl$_3$, δ in ppm): 0.81 (t, 3H, J=8.72 Hz), 1.38 (m, 2H), 1.52 (m, 2H), 1.51 (s, 6H), 1.86 (m, 1H), 2.05 (m, 1H), 2.21 (s, 6H), 2.5 (s, 3H), 2.55 (m, 1H), 2.63 (m, 1H), 3.26 (m, 2H), 4.13 (m, 1H), 6.81 (s, 2H), 7.24 (m, 4H).

MS(ES-MS): 443.5 (M−1).

Compound 24: 2-[2,6-dimethyl-4-[3-[4-(methylthio) phenyl]-3-isopropyloxypropyl]phenoxy]-2-methylpropanoic acid

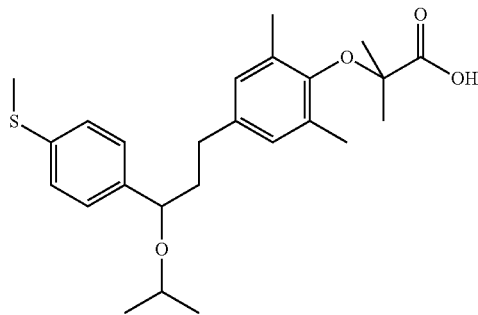

This compound was prepared according to general procedure E, from 2-[2,6-dimethyl-4-[3-[4-(methylthio)phenyl]-3-hydroxy-propyl]phenoxy]-2-methylpropanoic acid in 50/50 isopropyl alcohol/water at 70° C. for 32 hours;

Appearance: viscous oil.

NMR $^1$H (300 MHz, CDCl$_3$, δ in ppm): 1.09 (d, 3H, J=6.12 Hz), 1.14 (d, 3H, J=6.12 Hz), 1.5 (s, 6H), 1.79-1.90 (m, 1H), 1.97-2.09 (m, 1H), 2.2 (s, 6H), 2.44-2.54 (m, 1H), 2.5 (s, 3H), 2.67 (m, 1H), 3.47 (m, 1H), 4.27 (dd, 1H, J=5.27 Hz, J=8.17 Hz), 6.82 (s, 2H), 7.24 (s, 4H).

MS(ES-MS): 429.3 (M−1).

Compounds 22 and 25 were synthesized following one of the procedures A to E, in the manner described for compounds 1-21 and 23-24.

Example 3

In vitro Evaluation of the PPAR Activating Properties of the Compounds According to the Invention The PPAR activating properties of the compounds according to the invention are evaluated in vitro.

Principle

The activation of PPARs is evaluated in vitro using a monkey kidney fibroblast line (COS-7), by measuring the transcriptional activity of chimeras made up of the DNA binding domain of the Gal4 transcription factor of yeast and the binding domain to the ligand of the different PPARs. The compounds are tested at doses of between $10^{-7}$ and 100 μM on Gal4-PPARα, γ, and δ chimeras.

Protocol

Cell Cultivation

COS-7 cells come from ATCC (American type culture collection) and are cultivated in a DMEM (Dulbecco's modified eagle's medium) medium supplemented with 10% (vol/vol) of fetal calf serum, 100 U/ml of penicillin (Gibco, Paisley, UK) and 2 mM of L-Glutamine (Gibco, Paisley, UK). Cells are incubated at 37° C. in a humid atmosphere containing 5% $CO_2$.

Description of the Plasmids Used in Transfection

The plasmids Gal4(RE)_TkpGL3, pGal4-hPPARα, pGal4-hPPARγ, pGal4-hPPARδ, and pGal4-φ have been described in the literature (Raspe E et al., 1999). The constructions pGal4-hPPARα, pGal4-hPPARγ, and pGal4-hPPARδ have been obtained by cloning in the pGal4-φ vector of DNA fragments amplified by PCR and corresponding to DEF domains of human PPARα, PPARγ, and PPARδ nuclear receptors.

Transfection

The COS-7 cells in suspension are transfected with 150 ng of DNA well by well, with a pGal4-PPAR/Gal4(RE)_Tk-pGL3 ratio of 1/10, in presence of 10% fetal calf serum. The cells are plated in 96-well plates ($4 \times 10^4$ cells/well), then are incubated for 24 hours at 37° C. Activation with the test compounds is performed for 24 hours at 37° C. in a medium without serum. At the end of the experiment, the cells are lysed and the luciferase activity is determined using Steady-Lite™ FITS (Perkin Elmer) or Steady Glow Luciferase (Promega) in accordance with the provider's recommendations.

Results

The compounds according to the invention were tested on 3 PPAR isoforms. The results obtained with compounds 1-12, 14, 16-25 are detailed in FIGS. 1-1 to (1-66).

The inventors highlight the significant and dose-dependant augmentation of luciferase activity in the cells transfected with the plasmids pGal4-hPPAR and treated with the compounds according to the invention.

Conclusion

Unexpectedly, the disclosed experimental data show that the compounds according to the invention bind to PPARs in vitro and induce an activation of the transcriptional activity.

Example 4

In vivo Evaluation, on the ApoE2/E2 Mice, of Hypolipidemic Properties and Stimulative Properties of the Synthesis of HDL-cholesterol of the Compounds According to the Invention Principle The hypolipidemic properties of the compounds according to the invention are evaluated in vivo by assaying plasma lipids and the analysis of the PPARs target genes expression in the liver after a treatment treating of the dyslipidemic E2/E2 mice with the compounds according to the invention.

The murine model used is the ApoE2/E2 mouse, a transgenic mouse having the human apolipoprotein E isoform E2 (Sullivan P M et al., 1998). In human, this apolipoprotein, a constituent of low and very low density lipoproteins (LDL-VLDL), is present in three isoforms E2, E3, and E4. The E2 form presents a mutation affecting the amino acid in position 158, which considerably weakens the affinity of this protein for LDL receptors. Accordingly, the VLDL clearance is nearly non-existent. An accumulation of low-density lipoproteins then occurs along with a mixed hyperlipidemia known as type III (elevated cholesterol and triglycerides).

PPARα regulates the expression of genes involved in the transport of lipids (apolipoproteins such as Apo AI, Apo AII, and Apo CIII, membrane transporters such as FAT) and the catabolism of lipids (ACO, CPT-I, or CPT-II, fatty acid β-oxidation enzymes). Accordingly, the treatment with PPARα activators, in human as well as rodents, leads to a reduction in the circulating triglyceride level. Measuring the plasmatic lipids rate after a treatment with the compounds according to the invention allows to evaluate the PPAR agonist properties and the hypolipidemic effect of the compounds according to the invention.

The treatment with PPARs activators, in human as well as in rodents, also leads sometimes in an elevation of the plasma HDL-cholesterol rate. Measuring the HDL-cholesterol allows the show the aptitude of compounds according to the invention to stimulate the HDL-cholesterol synthesis.

The PPARα agonist properties previously measured in vitro should, in the liver, lead to an overexpression of the target genes directly under the control of the PPARα: the genes we have studied in this experiment are PDK-4 (an enzyme involved in glucid metabolism), Apo CIII (an apolipoprotein involved in lipid metabolism), and Acox1 (in mice, Acox1 corresponds to the ACO gene in humans (Acyl Co-enzymeA Oxydase, an enzyme key to the fatty acid β-oxidation mechanism)). Measuring the transcriptional activity of PPARα target genes after a treatment with compounds according to the invention does therefore allow to evaluate the hypolipidemic properties of the compounds according to the invention.

Protocol

Treatment of the Animals

The ApoE2/E2 transgenic mice were kept on a 12 hour/12 hour light/dark cycle at a constant temperature of 20±3° C. After a one week acclimatization period, the mice were weighed and divided into groups of 6 animals selected so as to render uniform the distribution of their body weights and plasma lipid rates, determined before the experiment. The tested compounds were suspended in carboxymethylcellulose (Sigma C4888) and administered by intra-gastric tube feeding once a day for 8 days (for compound 1) or 14 days (for compound 8) with the chosen doses. The animals had free access to food and water (standard diet). Taking of food and weight gain are recorded throughout the experiment. At the end of the experiment, the animals were anesthetized after a 4 hour fast, and a blood sample was taken using (EDTA) anticoagulant, then the mice were weighed and euthanized. The plasma was separated by centrifugation at 3000 rotations/minute for 20 minutes. The samples were kept at +4° C.

Liver samples were removed, frozen in liquid nitrogen, and kept at −80° C. for later analyses.

Measurement of Plasma Lipids

Plasma lipid concentrations (total cholesterol and triglycerides) are measured by enzymatic doses (bioMérieux-Lyon-France) according to the provider's recommendations.

Plasma cholesterol and triglycerides rates are measured after 8 or 14 days of a per os treatment with the compounds according to the invention. These rates are compared with those obtained with control animals (not treated with compounds according to the invention). The measured difference shows the hypolipidemic effect of the compounds according to the invention.

Gene Expression Analysis by Quantitative RT-PCR

Total RNA is extracted from liver fragments by using the NucleoSpin® 96 RNA kit (Macherey Nagel, Hoerdt, France) according to the manufacturer's instructions.

1 µg of total RNA (quantified by using the Ribogreen RNA quantification kit (Molecular Probes)) is then reverse-transcripted into complementary DNA by means of a 1 hour reaction at 37° C. in a total volume of 20 µl containing a 1× buffer (Sigma), 1.5 mM of DTT, 0.18 mM of dNTPs (Promega), 200 ng of pdN6 (Amersham), 30U of RNase inhibitor (Sigma), and 1 µl of MMLV-RT (Sigma).

The PCR quantitative experiments were carried out using the MyiQ Single-Color Real-Time PCR Detection System (Biorad, Marnes-la-Coquette, France) and were performed using the iQ SYBR Green Supermix kit according to the manufacturer's recommendations, in 96-well trays in 5 µl of a diluted reverse transcription solution at a hybidation temperature of 55° C. The specific primer pairs of the genes studied were used:

PDK4: sense primer: 5'-TACTCCACTGCTCCAACAC-CTG-3' (SEQ ID NO: 1) and antisense primer 5'-GT-TCTTCGGTTCCCTGCTTG-3' (SEQ ID NO: 2))

ApoCIII: sense primer: 5'-CTCTTGGCTCTCCTG-GCATC-3' (SEQ ID NO: 3) and antisense primer 5'-GCATCCTGGACCGTCTTGGA-3' (SEQ ID NO: 4).

ACO: sense primer: 5'-GAAGCCAGCGTTACGAGGTG-3' (SEQ ID NO: 5) and antisense primer: 5'-TGGAGT-TCTTGGGACGGGTG-3' (SEQ ID NO: 6)

The quantity of fluorescencet emitted is directly proportional to the quantity of cDNA present at the beginning of the reaction and amplified during the PCR. For each target studied, a range of PCR solution is performed with successive dilutions of a mixture made up of a few µl of different reverse-transcription solutions. The relative expression levels of each target are thus determined by using efficiency curves obtained with the points relative to range of PCR solutions. The expression levels of the genes of interest are then normalized regarding the one of the reference gene 36B4 (whose specific primers are: sense primer: 5'-CATGCTCAACATCTCCCCCTTCTCC-3' (SEQ ID NO: 79) and antisense primer: 5'-GGGAAGGTGTAATC-CGTCTCCACAG-3' (SEQ ID NO: 10)).

The induction factor, i.e. the ratio between the relative signal (induced by the compound according to the invention) and the average of relative values obtained with the control group is then calculated for each sample. The higher the induction factor is, the more the compound promotes gene expression. The final result is represented as the average of the induction values obtained with each experimental group.

Results

Measurement of Plasma Lipids

FIG. 2-1 compares the plasma total cholesterol rates after 8 days of treatment with compound 1 administered at 50 mpk with the ones obtained with the control animals. Unexpectedly, the circulating total cholesterol rates were very significantly decreased by the treatment.

FIG. 2-2 compares the plasma total cholesterol rates after 8 days of treatment with compound 1 administered at 50 mpk with the ones obtained from the control animals. Unexpectedly, the circulating triglycerides rates were very significantly decreased with the treatment.

FIG. 2-3 compares the plasma total cholesterol rates after 14 days of treatment with compound 8 administered at 3 and 10 mpk with the ones obtained with the control animals. Unexpectedly, the circulating total cholesterol rates were very significantly decreased with the treatment.

Gene Expression Analysis by Quantitative RT-PCR

The inventors have also shown that the compounds according to the invention are, in vivo, regulators of the PPARs target gene expression. The results disclosed at FIGS. 2-4, 2-5, and 2-6 show that compound 1 administered at 50 mpk for 8 days to the E2/E2 mice, induces a significant increase in hepatic expression of the gene coding for PDK4 (FIG. 2-4), a reduction in hepatic expression of the gene coding for ApoCIII (FIG. 2-5), and a significant augmentation in hepatic expression of genes coding for ACO (FIG. 2-6).

The results presented in FIGS. 2-7, 2-8, and 2-9 show that compound 8 administered at 3 and 10 mpk for 14 day to E2/E2 mice induces a significant augmentation in the hepatic expression of the genes coding for PDK4 (FIG. 2-7), a reduction in the hepatic expression of the genes coding for ApoCIII (FIG. 2-8), and a significant augmentation in hepatic expression of the genes coding for ACO (FIG. 2-9).

All the genes coding for enzymes specifically involved in lipid and glucid metabolism and the fact that their expression is modulated by the compounds according to the invention reinforce the idea that compounds according to the invention present a great potential for the treatment of metabolic pathologies.

Conclusion

Unexpectedly, the presented experimental data show that the compounds according to the invention induce a hypolipidemic effect (reduction in plasma levels of total cholesterol and triglycerides). Additionally, the presented experimental data show that the compounds according to the invention modulate the expression of genes regulated by the activation of PPARs that code for enzymes especially involved in lipid and glucid metabolism.

Example 5

In vivo Evaluation, on the db/db Mice, of Hypolipidemic Properties and Stimulative Properties of the Synthesis of HDL-cholesterol of the Compounds According to the Invention Principle The hypolipidemic properties of the compounds according to the invention are evaluated in vivo by measuring the plasma levels of plasmatic lipids and by analyzing the genetic expression PPARs target genes, after treating the dyslipidemic db/db mice with the compounds according to the invention, administered by the oral route.

Protocol

Treatment of the Animals

Female db/db mice were kept on a 12 hour/12 hour light/dark cycle at a constant temperature of 20±3° C. After a one week acclimatization period, the mice were weighed and divided into groups of 8 animals selected such as the distribution of body weight and of plasma lipid rate, determined before the experiment, was uniform. The tested compounds were suspended in carboxymethylcellulose (Sigma C4888) and administered to the animals by intra-gastric gavage, once a day for 28 days at the chosen doses. The animals had free access to food and water (standard diet). Taking of food and weight gain are recorded throughout the experiment. At the end of the experiment, after a 4 hour fast, the animals were anesthetized and a blood sample was taken on anticoagulant (EDTA). Then the mice were weighed and euthanized. The plasma was separated by centrifugation at 3000 rotations/minute for 20 minutes. The samples were kept at +4° C. The hepatic tissue and skeletal muscle samples were taken and frozen immediately in liquid nitrogen then conserved at −80° C. for later analysis.

Measurement of Plasma Lipids

Plasma triglycerides concentrations are measured by enzymatic assays (bioMérieux-Lyon-France) according to the provider's recommendations.

Measurement of HDL Cholesterol

Low-density lipoproteins (VLDL and LDL) are precipitated by phosphotungstate. The precipitate is eliminated by centrifugation. HDL-cholesterol present in the supernatant is measured by enzymatic assay (bioMérieux-Lyon-France) in accordance with the provider's recommendations.

Gene Expression Analysis by Quantitative RT-PCR

Hepatic Tissue

Total RNA is extracted from liver fragments by using a NucleoSpin® 96 RNA kit (Macherey Nagel, Hoerdt, France) according to the manufacturer's instructions.

Skeletal Tissue

Total RNA is extracted from gastrocnemius skeletal muscle fragments by using a RNeasy® Fibrous Tissue kit (Qiagen) according to the manufacturers instructions.

1 µg of total RNA (quantified by spectrophotometry) was then reverse-transcripted into complementary DNA by means of a 1 hour reaction at 37° C. in a total volume of 20 µl containing a 1× buffer (Sigma), 1.5 mM of DTT, 0.18 mM of dNTPs (Promega), 200 ng of pdN6 (Amersham), 30U of RNase inhibitor (Sigma), and 1 µl of MMLV-RT (Sigma).

The PCR quantitative experiments were carried out using the MyiQ Single-Color Real-Time PCR Detection System (Biorad, Marnes-la-Coquette, France) and were performed using the iQ SYBR Green Supermix kit according to the provider's recommendations, in 96-well plates, with 5 µl of diluted reverse transcription solutions and at a hybridization temperature of 55° C. The specific primer pairs of the genes studied were used:

PDK4: sense primer: 5'-TACTCCACTGCTCCAACAC-CTG-3' (SEQ ID NO: 1) and antisense primer 5'-GT-TCTTCGGTTCCCTGCTTG-3' (SEQ ID NO: 2))

ACO: sense primer: 5'-GAAGCCAGCGTTACGAGGTG-3' (SEQ ID NO: 5) and antisense primer: 5'-TGGAGT-TCTTGGGACGGGTG-3' (SEQ ID NO: 6)

UCP2: sense primer: 5'-GTCGGAGATACCAGAGCACT-GTCG-3' (SEQ ID NO: 7) and antisense primer 5'-CA-CATCAACAGGGGAGGCGA-3' (SEQ ID NO: 8)

The fluorescent quantity emitted is directly proportional to the amount of cDNA present at the beginning of the reaction and amplified during the PCR. For each target studied, a range of solutions is performed with successive dilutions of a mixture made up of a few microliters of different reverse-transcription reactions solutions. The relative levels of expression of each target are thus determined by using efficiency curves obtained with the points relative to the range of PCR solution.

The levels of expression of the genes of interest are then normalized, in the hepatic tissue, regarding the expression level of the reference gene 36B4 (whose specific primers are: sense primer: 5'-CATGCTCAACATCTCCCCTTCTCC-3' (SEQ ID NO: 9) and antisense primer: 5'-GGGAAGGTG-TAATCCGTCTCCACAG-3' (SEQ ID NO: 10) and, in the skeletal muscular tissue, regarding the expression level of the reference gene 18S (whose specific primers are: sense primer: 5'-CGGACACGGACAGGATTGACAG-3' (SEQ ID NO: 11) and antisense primer: 5'-AATCTCGGGTGGCTGAACGC-3' (SEQ ID NO: 12). The induction factor of each sample was then calculated. The higher the induction factor is, the greater the compound promotes gene expression. The final result is represented as the average of the induction values within each experimental group.

Results
Measurement of Plasma Lipids

FIG. 3-1 compares the plasma HDL-cholesterol rates after 28 days of treatment with compound 8 administered at 50 mpk with the ones obtained from the control animals. Unexpectedly, the HDL-cholesterol rates were significantly increased.

FIGS. 3-2 and 3-3 compare plasma triglycerides and free fatty acids rates after 28 days of treatment with compound 8 at 50 mpk, with the ones obtained from the control animals. Unexpectedly, the circulating triglycerides and free fatty acids rates were very significantly decreased by the treatment.

Gene Expression Analysis by Quantitative RT-PCR

The inventors have also shown that, in vivo, the compounds according to the invention areregulators of PPARs target gene expression. The results presented in FIGS. 3-4, 3-5, and 3-6 show that compound 8 administered at 50 mpk for 28 days to the db/db mice induces a significant increase of hepatic expression of the genes coding for PDK4 (FIG. 3-4) and for ACO (FIG. 3-5), and an increase of the expression of the gene coding for UCP2 (FIG. 3-6), in the skeletal muscle. All the genes coding for enzymes specifically involved in lipid and glucidic metabolism and in energy dissipation, and the fact that their expression is modulated by the compounds according to the invention reinforce the idea that compounds according to the invention have a great potential for the treatment of metabolic pathologies.

Conclusion

Unexpectedly, the presented experimental data show that the compounds according to the invention stimulate, in vivo, HDL cholesterol synthesis and have a hypolipidemic effect (reduction of plasma levels of triglycerides and free fatty acids). Additionally, the disclosed experimental data show that the compounds according to the invention modulate the expression of genes regulated by the activation of PPARs and that code for enzymes especially involved in lipid and glucid metabolism and in energy dissipation.

Example 6

In vitro Evaluation of the Anti-inflammatory Properties of the Compounds According to the Invention Principle The anti-inflammatory effects of the compound according to the invention were evaluated by measuring the secretion of MCP1 (Monocyte chemotactic protein-1) by THP1 monocytes treated for 24 hours with the compounds according to the invention and stimulated simultaneously with PMA (Phorbol 12-myristate 13-acetate, which promotes an inflammatory response in cells and their differentiation into macrophages). The less MCP-1 is secreted, the more the compound according to the invention inhibits the inflammatory reaction.

Protocol
Culture and Treatment of THP-1 Cells.

The THP-1 human monocytes line (ATCC source) is cultured in a RPMI1640 medium with 25 mM Hepes (Gibco; 42401-018), 1% glutamine (Gibco; 25030-24) 1% penicillin/streptomycin (Biochrom AG; A 2213), and 10% decomplemented fetal calf serum (SVF. Gibco; 26050-088).

The cells are plated in 24-well plates (Primaria BD Falcon) at a density of 870,000 cells/well then are incubated at 37° C. and 5% $CO_2$ for 24 hours in a culture medium containing 0.2% fetal calf serum in the presence of 5 ng/ml of phorbol 12-myristate 13-acetate (PMA) and 1 µM of compound 8 according to the invention. The compound according to the invention is dissolved in dimethyl sulfoxide (DMSO, Fluka; 41640). The effect of the compounds according to the invention is compared to the effect of DMSO alone.

Measurement of the Secretion of MCP1

The treatment medium is recovered and the MCP1 concentration is measured using the ELISA kit<<Human MCP-1 ELISA Set>>(BD OptEIA; 555179) in accordance with the manufacturer's recommendation.

MCP1 is laid on a plate and is recognized by a anti-MCP1 specific antibody. This specific antibody is itself specifically recognized by a second antibody coupled with a peroxydase enzyme. The coloration resulting from the enzymating activity is proportional to the quantity of fixed MCP1 and can be measured by a spectrophotometry method. A range is performed from a point representative of a known concentration and from which the MCP1 concentration of each sample is calculated.

The induction factor, i.e. the ratio between the signal induced by the compound according to the invention and the signal induced by the control group was then calculated. The weaker this factor is, the more the compound inhibits the secretion of MCP1. The final result is represented as the average of the induction values obtained with each experimental group.

Results

The inventors have proven that, on in vitro monocytes, the compounds according to the invention have anti-inflammatory effects. The results presented in FIG. 4-1 show that compound 8 according to the invention, at 1 µM, induces a significant reduction in MCP1 secreted by monocytes.

Conclusion

Unexpectedly, the disclosed experimental data show that the compounds according to the invention have an anti-inflammatory action on monocytes stimulated by PMA.

General conclusion

The inventors have shown that the compounds according to the invention have hypolipidemic properties, lead to an decrease of the plasma cholesterol and triglycerides rates, and also stimulate HDL-cholesterol synthesis. Additionally, the inventors have shown that the compounds according to the invention allow a regulation of the expression of genes coding for enzymes specifically involved in lipid and glucid metabolism and in energy dissipation.

The inventors have also shown that the compounds according to the invention have anti-inflammatory properties.

These results, obtained in vivo and in vitro, demonstrate the therapeutic potential of the compounds according to the invention for major pathologies such as dyslipidemias, type-2 diabetes, and obesity.

Bibliography

Fox-Tucker J, The Cardiovascular Market Outlook to 2010, BUSINESS INSIGHTS REPORTS, 2005, 1-174

Gross B, et al., Peroxisome Proliferator-Activated Receptor b/d: A novel target for the reduction of atherosclerosis, DRUG DISCOVERY TODAY: THERAPEUTIC STRATEGIES, 2005, 2 (3), 237-243

International Atherosclerosis Society, Harmonised Clinical. Guidelines on Prevention of Atherosclerotic Vascular Disease, 2003, Kota B P, et al., An overview on biological mechanisms of PPAR, Pharmacol Res, 2005, 51 (2), 85-94

Lefebvre P, et al., Sorting out the roles of PPARalpha in energy metabolism and vascular homeostasis, J Clin Invest, 2006, 116 (3), 571-580

Lehrke M and Lazar M A, The many faces of PPARgamma, Cell, 2005, 123 (6), 993-9

Liu Y and Miller A, Ligands to peroxisome proliferator-activated receptors as therapeutic options for metabolic syndrome, DRUG DISCOVERY TODAY: THERAPEUTIC STRATEGIES, 2005, 2 (3), 165-169

Mensah M, *The Atlas of Heart Disease and Stroke*, 2004,

Raspe E, et al., Modulation of rat liver apolipoprotein gene expression and serum lipid levels by tetradecylthioacetic acid (TTA) via PPAR(alpha) activation, J. Lipid Res., 1999, 40 (11), 2099-2110

Sullivan P M, et al., Type III hyperlipoproteinemia and spontaneous atherosclerosis in mice resulting from gene replacement of mouse Apoe with human Apoe*2, J Clin Invest, 1998, 102 (1), 130-5.

---

The invention claimed is:

1. A compound, derived from substituted 1,3-diphenylpropane, having general formula (I):

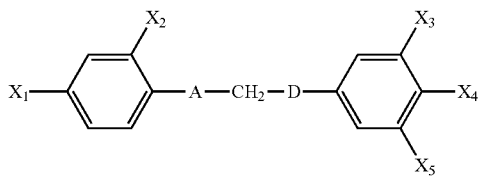

in which:
X1 represents a G1-R1 group;
X2 represents a halogen atom;
X3 represents a R3 group;
X4 represents a G4-R4 group;
X5 represents a R5 group;
R1 representing a non-halogenated alkyl group;
R4 representing an alkyl group substituted by a —COOR9 group;
R3 and R5 representing an unsubstituted alkyl group;
G1 represents an atom of sulfur and G4 represents an atom of oxygen or sulfur;
A represents
(i) a CR6R7 group, in which R6 represents a hydrogen atom, and R7 represents a hydroxyl group or a —OR8 group, R8 is as defined below,
(ii) a carbonyl group (CO),
(iii) an oxime group (C=N—O—H) or oxime ether (C=N—O—R8), R8, identical or different, representing an alkyl group, substituted or not by an aryl or cycloalkyl group;
D represents
a carbon atom linked to two hydrogen atoms (CH$_2$)
R9 representing an atom of hydrogen or an unsubstituted alkyl radical
its stereoisomers (diastereoisomers, enantiomers), pure or mixed, racemic mixtures, geometrical isomers, tautomers, salts, solid forms and mixtures thereof.

2. The compound according to claim 1, wherein A represents a carbonyl group (CO).

3. The compound according to claim 1, wherein represents a G4R4 group, wherein
R4 represents an alkyl group comprising from 1 to 10 carbon atoms, substituent by a —COOR9, as defined in claim 1.

4. The compound according to claim 1, wherein G4 represents an oxygen atom.

5. The compound according to claim 1, wherein the X4 group corresponds to the formula —OC(CH$_3$)$_2$COOR9, R9 being such as defined in claim 1.

6. The compound according to claim 1, wherein X3 and X5, identical or different, represent respectively a R3 and R5 group, R3 and R5 representing an unsubstituted alkyl group comprising from 1 to 4 carbon atoms.

7. The compound according to claim 1, wherein X1 represents a G1R1 group, G1 being such as defined in claim 1 and R1 representing a non-halogenated alkyl group comprising from 1 to 3 carbon atoms.

8. The compound according to claim 1, wherein said compound is selected from:
2,6-dimethyl-4-[3-[4-(methylthio)phenyl]-3-oxo-propyl]phenoxy]-ethanoic acid
2-[2,6-dimethyl-4-[3-[4-(propyloxy)phenyl]-3-oxo-propyl]phenoxy]-2-methyl-propanoic acid;
2-[2,6-dimethyl-4-[3-[4-(methylthio)phenyl]-3-oxo-propyl]phenoxy]-2-methyl-isopropyl propanoate;
2-[2,6-dimethyl-4-[3-[4-(methylthio)phenyl]-3- hydroxy-imino-propyl]phenoxy]-2-methyl-propanoic acid;
2-[2,6-dimethyl-4-[3-[4-(propyloxy)phenyl]-3- hydroxy-propyl]phenoxy]-2-methyl-propanoic acid;
2-[2,6-dimethyl-4-[3-[4-(methylthio)phenyl]-3-cyclohexylmethoxy-propyl]phenoxy]-2-methyl-propanoic acid;
2-[2,6-dimethyl-4-[3-[4-(methylthio)phenyl]-3-butyloxy-propyl]phenoxy]-2-methyl-propanoic acid;
2-[2,6-dimethyl-4-[3-[4-(methylthio)phenyl]-3-isopropyloxy-propyl]phenoxy]-2-methyl-propanoic acid;
2-[2,6-dimethyl-4-[3-[4-(methylthio)phenyl]-3-cyclohexylethyloxy-propyl]phenoxy]-2-methyl-propanoic acid;
2-[2,6-dimethyl-4-[3-[4-(methylthio)phenyl]-3-benzyloxy-propyl]phenoxy]-2-methyl-propanoic acid;
2-[2,6-dimethyl-4-[3-[4-(methylthio)phenyl]-3-hydroxy-propyl]phenoxy]-2-methyl-propanoic acid;
2-[2,6-dimethyl-4-[3-[4-(methylthio)phenyl]-3-ethyloxy-propyl]phenoxy]-2-methyl-propanoic acid;
2-[2,6-dimethyl-4-[3-[4-(methylthio)phenyl]-3-methoxy-propyl]phenoxy]-2-methyl-propanoic acid;

9. A pharmaceutical composition comprising, in a pharmaceutically acceptable support, at least one compound as defined in claim 1.

* * * * *